(12) United States Patent
Johnson et al.

(10) Patent No.: US 11,155,674 B2
(45) Date of Patent: Oct. 26, 2021

(54) POLYMERIZABLE SULFONAMIDE COMPOUNDS AND POLYMERS THEREOF

(71) Applicant: Massachusetts Institute of Technology, Cambridge, MA (US)

(72) Inventors: Jeremiah A. Johnson, Boston, MA (US); Mao Chen, Boston, MA (US); Mingjun Huang, Everett, MA (US); Wenxu Zhang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 370 days.

(21) Appl. No.: 15/876,106

(22) Filed: Jan. 19, 2018

(65) Prior Publication Data

US 2018/0208712 A1    Jul. 26, 2018

Related U.S. Application Data

(60) Provisional application No. 62/448,456, filed on Jan. 20, 2017.

(51) Int. Cl.
   *C07C 311/48* (2006.01)
   *C08G 61/08* (2006.01)
   (Continued)

(52) U.S. Cl.
   CPC ............ *C08G 61/06* (2013.01); *A61K 47/585* (2017.08); *C07C 13/263* (2013.01); *C07C 311/48* (2013.01); *C07D 225/02* (2013.01); *C07D 295/096* (2013.01); *C08F 4/82* (2013.01); *C08F 8/04* (2013.01); *C08F 12/30* (2013.01); *C08F 28/02* (2013.01); *C08F 34/00* (2013.01); *C08G 61/08* (2013.01); *C08J 5/2262* (2013.01); *C09J 165/00* (2013.01); *H01B 1/122* (2013.01);
   (Continued)

(58) Field of Classification Search
   CPC ...... C07C 311/48; C07C 311/37; C08F 12/30; C08F 28/02; C08F 128/02; C08F 112/30; C08F 212/30; C08F 228/02; C08G 61/06
   See application file for complete search history.

(56) References Cited

U.S. PATENT DOCUMENTS

| | | | |
|---|---|---|---|
| 5,811,515 A | 9/1998 | Grubbs et al. | |
| 6,063,522 A * | 5/2000 | Hamrock | H01M 6/183 429/200 |

(Continued)

FOREIGN PATENT DOCUMENTS

WO    WO 2013/169739 A1    11/2013

OTHER PUBLICATIONS

U.S. Appl. No. 15/875,907, filed Jan. 19, 2018, Johnson et al.

(Continued)

*Primary Examiner* — Ling Siu Choi
*Assistant Examiner* — David L Miller
(74) *Attorney, Agent, or Firm* — Wolf, Greenfield & Sacks, P.C.

(57) ABSTRACT

Methods, compositions, reagents, and systems that allow for the preparation and utilization of sulfonamide salt polymer electrolytes are disclosed herein. Methods and reagents to prepare sulfonamide salt monomers are also disclosed herein. The sulfonamide salt polymer electrolytes can be used as components in energy storage devices, conductive materials, electrochemical cells, gels, adhesives, and drug delivery vehicles.

22 Claims, 27 Drawing Sheets

(51) Int. Cl.

| | |
|---|---|
| C08G 61/06 | (2006.01) |
| C08F 12/30 | (2006.01) |
| C08F 34/00 | (2006.01) |
| C08F 28/02 | (2006.01) |
| C08F 8/04 | (2006.01) |
| C08F 4/82 | (2006.01) |
| C07C 13/263 | (2006.01) |
| H01B 1/12 | (2006.01) |
| H01M 10/0565 | (2010.01) |
| H01M 8/1027 | (2016.01) |
| A61K 47/58 | (2017.01) |
| C09J 165/00 | (2006.01) |
| C07D 225/02 | (2006.01) |
| C08J 5/22 | (2006.01) |
| C07D 295/096 | (2006.01) |
| H01M 10/052 | (2010.01) |
| C08F 228/04 | (2006.01) |
| C08F 128/02 | (2006.01) |
| C08F 112/14 | (2006.01) |
| C08F 212/14 | (2006.01) |
| C07C 311/37 | (2006.01) |
| C08F 228/02 | (2006.01) |

(52) U.S. Cl.
CPC ....... *H01M 8/1027* (2013.01); *H01M 10/052* (2013.01); *H01M 10/0565* (2013.01); *C07C 311/37* (2013.01); *C08F 112/30* (2020.02); *C08F 128/02* (2013.01); *C08F 212/30* (2020.02); *C08F 228/02* (2013.01); *C08F 228/04* (2013.01); *C08F 2438/01* (2013.01); *C08F 2438/03* (2013.01); *C08G 2261/143* (2013.01); *C08G 2261/146* (2013.01); *C08G 2261/148* (2013.01); *C08G 2261/1452* (2013.01); *C08G 2261/3322* (2013.01); *C08G 2261/418* (2013.01); *C08J 2365/00* (2013.01); *H01M 2300/0082* (2013.01)

(56) References Cited

U.S. PATENT DOCUMENTS

| | | | |
|---|---|---|---|
| 9,381,253 B2 | 7/2016 | Johnson et al. | |
| 2008/0286626 A1* | 11/2008 | Olmeijer | C08G 65/4012 429/483 |
| 2011/0218255 A1* | 9/2011 | Teasley | C08G 61/10 521/27 |
| 2016/0190641 A1* | 6/2016 | Lee | H01M 10/0565 429/303 |
| 2018/0208699 A1 | 7/2018 | Johnson et al. | |

OTHER PUBLICATIONS

Almdal et al., Gaussian- to stretched-coil transition in block copolymer melts. Phys. Rev. Lett. 1990;65:1112.
Anderson et al., Surface morphology of PS-PDMS diblock copolymer films. J Electron Spectrosc Relat Ph. 2001;121:93-110. 10.1016/S0368-2048(01)00329-2.
Bates et al., Block Copolymer Lithography. Macromolecules, 2014, 47 (1), pp. 2-12. DOI: 10.1021/ma401762n.
Bates et al., Block Copolymer Thermodynamics: Theory and Experiment. Annual Review of Physical Chemistry 1990;41(1):525-557.
Bates et al., Block Copolymers—Designer Soft Materials. Physics Today 1999;52(2):32 https://doi.org/10.1063/1.882522.
Berthier et al., Microscopic investigation of ionic conductivity in alkali metal salts-poly(ethylene oxide) adducts. Solid State Ionics, Sep. 1983;11(1):91-95.
Bouchet et al., Single-ion BAB triblock copolymers as highly efficient electrolytes for lithium-metal batteries. Nat Mater. May 2013;12(5):452-7. doi: 10.1038/nmat3602. Epub Mar. 31, 2013.

Chen et al., Thiocarbonylthio end group removal from RAFT-synthesized polymers by a radical-induced process.. J. Polym. Sci. A Polym. Chem., 2009;47:6704-6714. doi:10.1002/pola.23711.
Cushen et al., Thin Film Self-Assembly of Poly(trimethylsilylstyrene-b-d,l-lactide) with Sub-10 nm Domains. Macromolecules, 2012;45(21):8722-8728. DOI: 10.1021/ma301238j.
Epps et al., Phase Behavior of Lithium Perchlorate-Doped Poly(styrene-b-isoprene-b-ethylene oxide) Triblock Copolymers. Chem. Mater., 2002;14(4):1706-1714. DOI: 10.1021/cm010971t.
Furstner et al., Alkyne Metathesis: Development of a Novel Molybdenum-Based Catalyst System and Its Application to the Total Synthesis of Epothilone A and C. Chem. Eur. J. 2001;7:5299.
Furstner et al., Mo[N(t—Bu)(Ar)]3 Complexes as Catalyst Precursors: In Situ Activation and Application to Metathesis Reactions of Alkynes and Diynes. J. Am. Chem. Soc., 1999;121(40):9453-9454. DOI: 10.1021/ja991340r.
Gallivan et al., A neutral, water-soluble olefin metathesis catalyst based on an N-heterocyclic carbene ligand. Tetrahedron Letters 2005;46(15):2577-2580.
Grubbs et al., Ring-Closing Metathesis and Related Processes in Organic Synthesis. Acc. Chem. Res., 1995, 28 (11), pp. 446-452. DOI: 10.1021/ar00059a002.
Hashimoto et al., Domain-Boundary Structure of Styrene-Isoprene Block Copolymer Films Cast from Solution. 4. Molecular-Weight Dependence of Lamellar Microdomains. Macromolecules, 1980, 13 (5), pp. 1237-1247. DOI: 10.1021/ma60077a040.
Isono et al., Sub-10 nm Nano-Organization in AB2- and AB3-Type Miktoarm Star Copolymers Consisting of Maltoheptaose and Polycaprolactone. Macromolecules, 2013;46(4):1461-1469. DOI: 10.1021/ma3026578.
Jackson et al., Nanoporous membranes derived from block copolymers: from drug delivery to water filtration. ACS Nano. Jul. 27, 2010;4(7):3548-53. doi: 10.1021/nn1014006.
Jeong et al., Realizing 5.4 nm Full Pitch Lamellar Microdomains by a Solid-State Transformation. Macromolecules, 2017;50(18):7148-7154. DOI: 10.1021/acs.macromol.7b01443.
Kennemur et al., Sub-5 nm Domains in Ordered Poly(cyclohexylethylene)-block-poly(methyl methacrylate) Block Polymers for Lithography. Macromolecules, 2014;47(4):1411-1418. DOI: 10.1021/ma4020164.
Kim et al., Mussel-inspired block copolymer lithography for low surface energy materials of teflon, graphene, and gold. Adv Mater. Dec. 15, 2011;23(47):5618-22. doi: 10.1002/adma.201103650. Epub Oct. 21, 2011.
Kim et al., Salt Complexation in Block Copolymer Thin Films. Macromolecules, 2006;39(24):8473-8479. DOI: 10.1021/ma061170k.
Koo et al., Directed self-assembly of block copolymers in the extreme: guiding microdomains from the small to the large. Soft Matter, 2013;9:9059-9071. DOI: 10.1039/C3SM51083B.
Kwak et al., Fabrication of Sub-3 nm Feature Size Based on Block Copolymer Self-Assembly for Next-Generation Nanolithography. Macromolecules, 2017;50(17):6813-6818. DOI: 10.1021/acs.macromol. 7b00945.
Leibler et al., Theory of Microphase Separation in Block Copolymers. Macromolecules, 1980;13(6):602-1617. DOI: 10.1021/ma60078a047.
Liu et al., "Brush-First" Method for the Parallel Synthesis of Photocleavable, Nitroxide-Labeled Poly(ethylene glycol) Star Polymers. J. Am. Chem. Soc., 2012, 134 (39), pp. 16337-16344. DOI: 10.1021/ja3067176.
Liu et al., Particles without a box: brush-first synthesis of photodegradable PEG star polymers under ambient conditions. J Vis Exp. Oct. 10, 2013;(80). doi: 10.3791/50874.
Lo et al., Silicon-Containing Block Copolymers for Lithographic Applications. 2017. 10.1016/j.progpolymsci.2017.10.002.
Luo et al., Poly(dimethylsiloxane-b-methyl methacrylate): A Promising Candidate for Sub-10 nm Patterning. Macromolecules, 2015;48(11):3422-3430. DOI: 10.1021/acs.macromol.5b00518.
Ma et al., Single Lithium-Ion Conducting Polymer Electrolytes Based on a Super-Delocalized Polyanion. Angew Chem Int Ed Engl. Feb. 12, 2016;55(7):2521-5. doi: 10.1002/anie.201509299. Epub Jan. 14, 2016.

(56) References Cited

OTHER PUBLICATIONS

Minier et al., Thermal analysis and NMR study of a poly(ethylene oxide) complex electrolyte : PEO(LiCF3SO3)x. J. Phys. France 1984;45:739-744. DOI: 10.1051/jphys:01984004504073900.

Olvera de la Cruz et al., Theory of microphase separation in graft and star copolymers. Macromolecules, 1986;19(10):2501-2508. DOI: 10.1021/ma00164a008.

Papadakis et al., Identification of an intermediate-segregation regime in a diblock copolymer system. Europhys. Lett., 1996;36(4):289-294.

Park et al., Macroscopic 10-terabit-per-square-inch arrays from block copolymers with lateral order. Science. Feb. 20, 2009;323(5917):1030-3. doi: 10.1126/science.1168108.

Peinemann et al., Asymmetric superstructure formed in a block copolymer via phase separation. Nat Mater. Dec. 2007;6(12):992-6. Epub Nov. 4, 2007.

Poelma et al., Cyclic Block Copolymers for Controlling Feature Sizes in Block Copolymer Lithography. ACS Nano, 2012;6(12):10845-10854. DOI: 10.1021/nn304217y.

Rodwogin et al., Polylactide-poly(dimethylsiloxane)-polylactide triblock copolymers as multifunctional materials for nanolithographic applications. ACS Nano. Feb. 23, 2010;4(2):725-32. doi: 10.1021/nn901190a.

Ruiz et al., Density multiplication and improved lithography by directed block copolymer assembly. Science. Aug. 15, 2008;321(5891):936-9. doi: 10.1126/science.1157626.

Russell et al., Temperature dependence of the interaction parameter of polystyrene and poly(methyl methacrylate). Macromolecules, 1990;23(3):890-893. DOI: 10.1021/ma00205a033.

Schrock et al., Tungsten(VI) neopentylidyne complexes. Organometallics, 1982, 1 (12), pp. 1645-1651. DOI: 10.1021/om00072a018.

Schulze et al., Poly(cyclohexylethylene)-block-poly(ethylene oxide) Block Polymers for Metal Oxide Templating. ACS Macro Lett., 2015;4(9):1027-1032. DOI: 10.1021/acsmacrolett.5b00458.

Shi et al., Producing Small Domain Features Using Miktoarm Block Copolymers with Large Interaction Parameters. ACS Macro Lett., 2015;4(11):1287-1292. DOI: 10.1021/acsmacrolett.5b00712.

Sinturel et al., High χ—Low N Block Polymers: How Far Can We Go? ACS Macro Lett., 2015, 4 (9), pp. 1044-1050. DOI: 10.1021/acsmacrolett.5b00472.

Smith et al., Batteries. Opening the window for aqueous electrolytes. Science. Nov. 20, 2015;350(6263):918. doi: 10.1126/science.aad5575.

Sun et al., Directed Self-Assembly of Poly(2-vinylpyridine)-b-polystyrene-b-poly(2-vinylpyridine) Triblock Copolymer with Sub-15 nm Spacing Line Patterns Using a Nanoimprinted Photoresist Template. Adv Mater. Aug. 5, 2015;27(29):4364-70. doi: 10.1002/adma.201501585. Epub Jun. 18, 2015.

Sun et al., Using Block Copolymer Architecture to Achieve Sub-10 nm Periods. Polymer, 2017;121:297-303 DOI: 10.1016/j.polymer.2017.

Sunday et al., Characterizing the Interface Scaling of High χ Block Copolymers near the Order-Disorder Transition. Macromolecules, 2018, 51 (1), pp. 173-180. DOI: 10.1021/acs.macromol.7b01982.

Suo et al., "Water-in-salt" electrolyte enables high-voltage aqueous lithium-ion chemistries. Science. Nov. 20, 2015;350(6263):938-43. doi: 10.1126/science.aab1595.

Sweat et al., Rational Design of a Block Copolymer with a High Interaction Parameter. Macromolecules, 2014;47(19):6687-6696. DOI: 10.1021/ma501597g.

Teran et al., Thermodynamics of Block Copolymers with and without Salt. J. Phys. Chem. B, 2014;118(1):4-17. DOI: 10.1021/jp408079z.

Thurn-Albrecht et al., Ultrahigh-density nanowire arrays grown in self-assembled diblock copolymer templates. Science. Dec. 15, 2000;290(5499):2126-9.

Tirumala et al., Well Ordered Polymer Melts from Blends of Disordered Triblock Copolymer Surfactants and Functional Homopolymers. Adv. Mater., 2008;20:1603-1608. doi:10.1002/adma.200701577.

Van Genabeek et al., Synthesis and Self-Assembly of Discrete Dimethylsiloxane-Lactic Acid Diblock Co-oligomers: The Dononacontamer and Its Shorter Homologues. J. Am. Chem. Soc., 2016;138(12):4210-4218. DOI: 10.1021/jacs.6b00629.

Wang et al., Block Co-PolyMOCs by Stepwise Self-Assembly. J. Am. Chem. Soc., 2016;138(33):10708-10715. DOI: 10.1021/jacs.6b06712.

Wright et al., Electrical conductivity in ionic complexes of poly-(ethylene oxide). Brit. Poly. J., 1975;7:319-327. doi:10.1002/pi.4980070505.

Yang et al., Virus Filtration Membranes Prepared from Nanoporous Block Copolymers with Good Dimensional Stability under High Pressures and Excellent Solvent Resistance. Adv. Funct. Mater., 18: 1371-1377. doi:10.1002/adfm.200700832.

Young et al., Salt Doping in PEO-Containing Block Copolymers: Counterion and Concentration Effects. Macromolecules, 2009;42(7):2672-2678. DOI: 10.1021/ma802799p.

Zha et al., Origin of the Difference in Order-Disorder Transition Temperature between Polystyrene-block-poly(2-vinylpyridine) and Polystyrene-block-poly(4-vinylpyridine) Copolymers. Macromolecules, 2007;40(6):2109-2119. DOI: 10.1021/ma062516u.

Huang et al., Fluorinated Aryl Sulfonimide Tagged (FAST) salts: modular synthesis and structure-property relationships for battery applications. Energy Environ. Sci., 2018, Advance Article DOI: 10.1039/C7EE03509H.

Xu et al., Polymer encapsulated upconversion nanoparticle/iron oxide nanocomposites for multimodal imaging and magnetic targeted drug delivery. Biomaterials. Dec. 2011;32(35):9364-73. doi:10.1016/j.biomaterials.2011.08.053. Epub Aug. 30, 2011.

Fuchs et al, Induction of Amphiphilicity in Polymer Silica Particles: Ceramic Surfactants, Langmuir. 2013;29(9):2835-2842.

Hu et al, Nanocomposites with Spatially Separated Functionalities for Combined Imaging and Magnetolytic Therapy, J American Chemical Society. 2010;132(21):7234-7237.

O'Malley et al, Synthesis of mesoporous aluminophosphates-based materials using various copolymers as templates, Microporous and Mesoporous Materials. 2014;191:48-58.

Ozkan et al, Mesoporous sol-gel W03 thin films via poly(styrene-co-allyl-alcohol) copolymer templates, Solid State Ionics. 2003;165(1-4), 65-72.

\* cited by examiner

Modular sequential installation of side groups facilitates the tuning of material properties.

$^{19}$F NMR
a) After chemical stability test (in d$_6$-DMSO)
b) Before chemical stability test (in d$_3$-MeOH)

Conditions:
Li$_2$O$_2$ and KO$_3$ in DMF at 80 °C 3 days

Synthesis of a monomer

Synthesis of a monomer

Synthesis of a monomer

Synthesis of a monomer

Synthesis of a monomer

Polymer synthesis

Polymer synthesis

Synthesis of a Cyclooctene Based Monomer

Synthesis of a Monomer by-products:

Synthesis of a Monomer

Synthesis of polymers

Synthesis of cAA Monomer

Synthesis of cAA Monomer

Synthesis of polymers

Hydrogenation

Hydrogenation

Synthesis of a COE Monomer

Synthesis of COE Monomer

*Introducing spacers to reduce the $T_g$ of poly(sulfonimide)*

Can be achieved using modular stepwise synthesis
Methods to Enhance Ionic Conductivities

Synthesis of Polymers

Synthesis of cAA Polymers

Synthesis of COE Polymers

- Modular sequential installation of side groups facilitates the tuning of material properties.

Exemplary monomers

POLYMERIZABLE SULFONAMIDE COMPOUNDS AND POLYMERS THEREOF

RELATED APPLICATIONS

This application claims priority under 35 U.S.C. 119(e) to U.S. Provisional Application, U.S. Ser. No. 62/448,456, filed Jan. 20, 2017, which is incorporated herein by reference.

BACKGROUND OF THE INVENTION

Synthetic polymers are typically used as structural materials or as electric insulators. However, synthetic polymers have more recently been tailored as electron or ion conductors; when combined with appropriate salts their ionic conductivity can be put to use as an electrolyte. In 1975, it was shown that polyethylene oxide (PEO) can act as a host for sodium and potassium salts, thus producing a solid electrical conductor polymer/salt complex.[1] Armand suggested that lithium/PEO complexes could be utilized as solid electrolytes because they matched well with intercalation electrodes. A lithium salt could be dissolved in a solvating polymer matrix through direct interaction of the cation and electron pairs. The complex formed, as a result of the favorable competition between the solvation energy of the salt, becomes a good conductor at 60 to 80° C.[2] Experiments performed to understand the formation of a salt complex and the nature of the charge transport mechanism of lithium/PEO complexes revealed that ionic motion in salt-polymer complexes is due to continuous motion occurring in the amorphous region of the polymeric material.[3] The intrinsic phenomenon of a solid material exhibiting liquid-like conductivity without motion of the solvent itself was a fascinating from a theoretical point of view and the applications to electrochemical devices seemed promising. In addition, a polymer electrolyte can be easily manufactured into shapes not available to liquid containing systems, and it is safer than liquid electrolytes.

From a practical standpoint, lithium/PEO complexes are not themselves ideal electrolytes. Several manipulations are required to prevent crystallization and to extend the domain of existence of the elastomeric phase favorable to high ionic conductivity: plasticizing the matrix by addition of a low molecular weight polar molecule or forming a block of comb copolymers. Meanwhile, other structurally similar polymers were extensively studied, such as polypropylene oxide (PPO); and other classes of conductive polymers have been prepared. As electronically conductive polymers have captured the attention of many scientists, the interest of the solid-state ionics community shifted toward mixed conductors (backbone polymers or redox polymers).

Beyond polymer electrolytes, molecular electrolytes remain the most utilized electrolytes utilized in modern electronics. The increasing demands of modern electronics necessitate the development of energy storage devices that feature greater power and energy densities without compromising affordability and safety. With the advantages of broad electrochemical stability window, high thermal stability, and low vulnerability towards moisture hydrolysis, lithium bis(trifluoromethanesulfonyl)imide (LiTFSI) is widely used as a lithium source in new battery chemistries with higher theoretical energy densities beyond lithium-ion battery, such as lithium-air and lithium-sulfur batteries. Moreover, LiTFSI is also the most studied lithium salt especially in solid-state polymer electrolytes, due to its desirable solubility and excellent stability.[4] However, chemically inert LiTFSI cannot be easily modified to optimize its properties or to conjugate it to other molecules, polymers, or substrates to prepare single-ion conducting polymer electrolytes.

SUMMARY OF THE INVENTION

Described herein are a class of sulfonamide compounds, including salts thereof, with polymerizable groups that undergo polymerization reactions to produce salt polymers or polymer electrolytes that bear sulfonamide sidechains and carbon backbones. These polymers, including salts thereof, are designed to be stable towards chemical reactions such as radical abstraction, deprotonation, electrochemical oxidation, and nucleophilic attack. These polymers have potential applications as components of batteries and other devices that require ion conductivity in harsh chemical and electrochemical environments. Furthermore, the use of fluorinated aryl groups allows for modular introduction of functionality onto the polymer sidechains through nucleophilic aromatic substitution processes, thus enabling access to a wide range of novel polysulfonamides with variable structures for tuning the glass transition temperature, stability, and other material properties.

Methods, compositions, reagents, kits, and systems that allow for the preparation and utilization of sulfonamide salt polymer electrolytes are disclosed herein. Methods and reagents to prepare sulfonamide salt monomers are also disclosed herein.

The sulfonamide salt monomers described herein contain a polymerizable group for polymerization for the preparation of polymer electrolytes. In certain embodiments, the sulfonamide salt monomers are compounds of Formula (I):

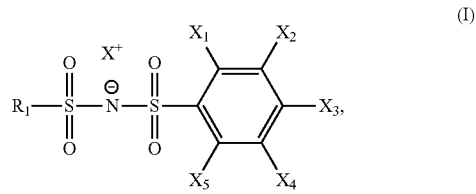

or a salt thereof,
wherein:
R₁ is optionally substituted alkyl or optionally substituted phenyl;
X⁺ is a counterion;
X₁, X₂, X₃, X₄ and X₅ independently is hydrogen; halogen; optionally substituted, cyclic or acyclic alkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; —OR₂; —N(R₃)₂; or —SR₂;

each R₂ independently is hydrogen; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; optionally substituted heteroaryl; an oxygen protecting group; or a sulfur protecting group; and each R₃ is hydrogen; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; or optionally substituted heteroaryl; a nitrogen protecting group; or two $R_3$ are taken together to form an optionally substituted heterocyclic moiety;

provided that at least one of $X_1$, $X_2$, $X_3$, $X_4$ and $X_5$ comprises optionally substituted, cyclic or acyclic alkenyl; optionally substituted, cyclic or acyclic heteroalkenyl; optionally substituted, cyclic or acyclic alkynyl, or optionally substituted, cyclic or acyclic heteroalkynyl; and at least one of $X_1$, $X_2$, $X_3$, $X_4$ and $X_5$ is halogen; or optionally substituted, cyclic or acyclic alkyl.

The sulfonamide salt monomers described herein are prepared by one or more nucleophilic aromatic substitution reactions. In certain embodiments, the present disclosure provides methods of preparing a sulfonamide salt monomer compound of Formula (I) comprising reacting a compound of Formula (I-b):

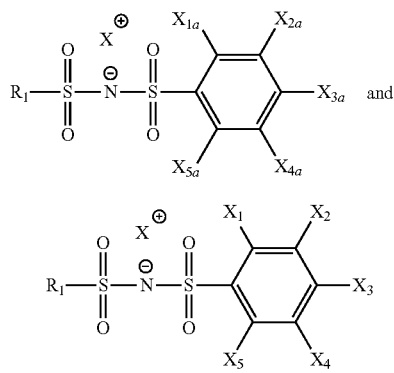

with one or more nucleophiles selected from $HOR_2$, $HN(R_3)_2$, $HSR_2$, and $HC(R_3)_3$ to obtain a compound of Formula (I);

wherein:

$X_{1a}$, $X_{2a}$, $X_{3a}$, $X_{4a}$, and $X_{5a}$ independently is independently is hydrogen; halogen; optionally substituted, cyclic or acyclic alkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted carbonyl; $-OR_2$; $-N(R_3)_2$; or $-SR_2$;

each $R_2$ independently is hydrogen; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; optionally substituted heteroaryl; an oxygen protecting group; or sulfur protecting group;

each $R_3$ independently is hydrogen; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; optionally substituted heteroaryl; a nitrogen protecting group; or two $R_3$ are taken together to form an optionally substituted cyclic alkenyl or an optionally substituted cyclic alkynyl;

provided that at least one of $X_1$, $X_2$, $X_3$, $X_4$ and $X_5$ is optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; and at least one of $X_1$, $X_2$, $X_3$, $X_4$ and $X_5$ is halogen; optionally substituted cyclic or acyclic alkyl; and provided that at least one of $X_{1a}$, $X_{2a}$, $X_{3a}$, $X_{4a}$, and $X_{5a}$ is halogen or optionally substituted alkyl.

The polymerization of the compounds of Formula (I) via a polymerization reaction produces polymers of Formula (II):

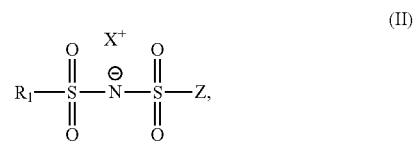

or a salt thereof, wherein Z is:

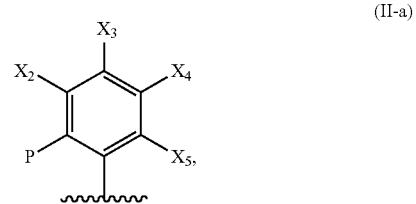

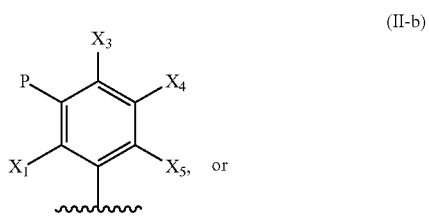

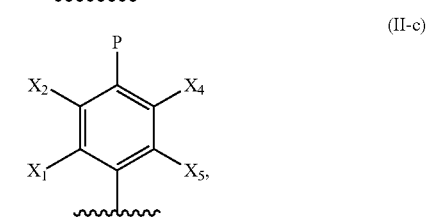

wherein P is:

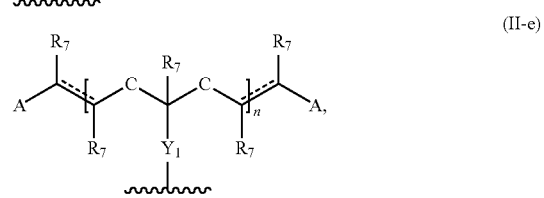

-continued

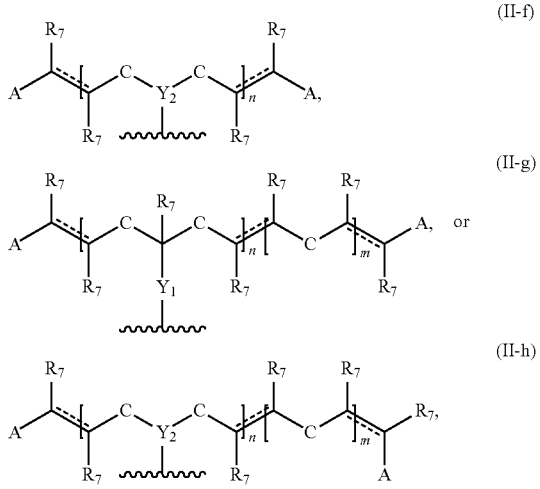

wherein:

=== is a single bond or a double bond $R_1$ is optionally substituted alkyl or optionally substituted phenyl;

$X^+$ is a counterion;

$X_1$, $X_2$, $X_3$, $X_4$, and $X_5$ independently is hydrogen; halogen; optionally substituted, cyclic or acyclic alkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted carbonyl; —$OR_2$; —$N(R_3)_2$; or —$SR_2$;

each $R_2$ independently is hydrogen; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; optionally substituted heteroaryl; an oxygen protecting group; or sulfur protecting group;

each $R_3$ independently is hydrogen; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; optionally substituted heteroaryl; a nitrogen protecting group; or two $R_3$ are taken together to form an optionally substituted heterocyclic moiety;

each $R_7$ independently is halogen; hydrogen; optionally substituted, cyclic or acyclic alkyl; optionally substituted, cyclic or acyclic heteroalkyl; optionally substituted aryl; or optionally substituted heteroaryl;

$Y_1$ is O, S, $NR_4$, $C(R_4)_2$, $OC(R_4)_2$, $(R_4)_2CO$, optionally substituted acyl, optionally substituted aryl, or optionally substituted heteroaryl;

$Y_2$ is N, $CR_4$, optionally substituted aryl, or optionally substituted heteroaryl;

A is optionally substituted, cyclic or acyclic alkyl; optionally substituted, cyclic or acyclic heteroalkyl; optionally substituted aryl; optionally substituted heteroaryl, optionally substituted acyl; —$OR_2$; —$N(R_3)_2$; or —$SR_2$;

each C independently is optionally substituted, cyclic or acyclic alkyl; optionally substituted, cyclic or acyclic heteroalkyl; optionally substituted aryl; optionally substituted heteroaryl; optionally substituted acyl; or polymer;

each n and m independently is an integer between 1 and 100, inclusive.

In yet another aspect, the present disclosure provides methods of preparing a polymer of Formula (II), comprising polymerizing a compound of Formula (I) to produce a polymer of a Formula (II). In certain embodiments, the preparation of a polymer of Formula (II) further comprises a step of hydrogenating the polymer.

In some embodiments, the present disclosure provides compositions comprising a polymer described herein. In certain embodiments, the composition is a polymer electrolyte. In certain embodiments, the polymer electrolyte is a component of an energy storage device. In certain embodiments, the polymer electrolyte is a component of a conductive material. In certain embodiments, the polymer electrolyte is a component of an electrochemical cell. In certain embodiments, the polymer electrolyte is a component of a gel. In certain embodiments, the polymer electrolyte is a component of an adhesive. In certain embodiments, the polymer electrolyte is a component of a coating. In certain embodiments, the polymer electrolyte is a component of a delivery vehicle.

The present disclosure also provides methods of performing ion exchange reactions to prepare a second salt of a polymer of Formula (II) from a first salt of a polymer of Formula (II) utilizing an ionic compound. In certain embodiments, lithium salts of a polymer of Formula (II) are prepared from the sodium salt of a polymer of Formula (II), comprising an ion exchange reaction of the sodium salt of a polymer of Formula (II) with an inorganic lithium salt.

The details of certain embodiments of the invention are set forth in the Detailed Description of Certain Embodiments, as described below. Other features, objects, and advantages of the invention will be apparent from the Definitions, Figures, Examples, and Claims.

DEFINITIONS

Figure 1:
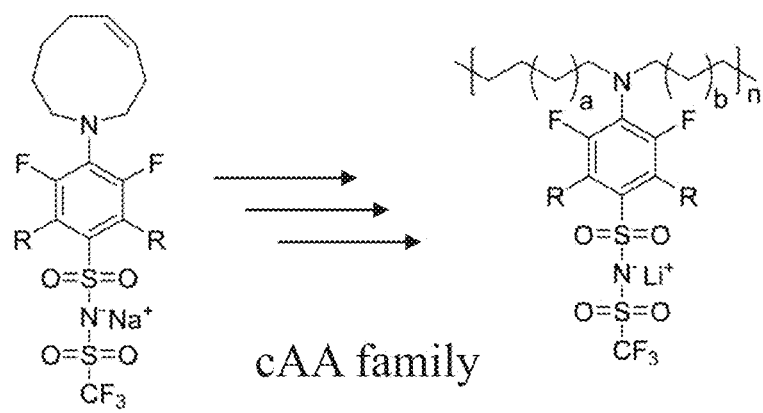
FIG. 1 shows the synthesis of lithium sulfonamide polymer electrolytes from sulfonamide salts substituted at the para position with a hexahydroazonine substituent. The synthesis involves three steps: 1) a ring opening metathesis polymerization; 2) a hydrogenation; and 3) an ion exchange reaction.
Figure 2:
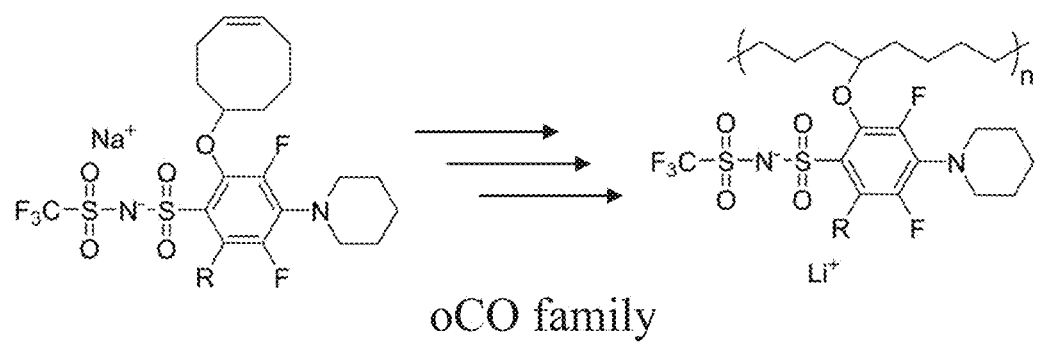
FIG. 2 shows the synthesis of lithium sulfonamide polymer electrolytes from sodium sulfonamide salts substituted at the ortho position with a hydroxycyclooctene substituent and substituted at the para position with a piperdine substituent. The synthesis involves three steps: 1) a ring opening metathesis polymerization; 2) a hydrogenation; and 3) an ion exchange reaction.
Figure 3:
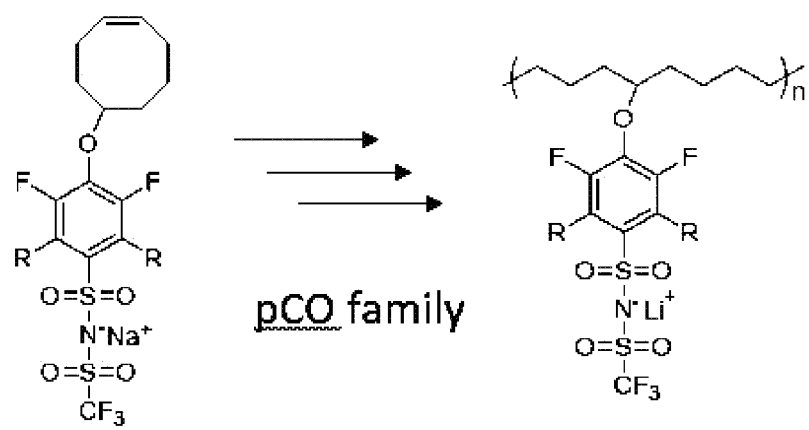
FIG. 3 shows the synthesis of lithium sulfonamide polymer electrolytes from sodium sulfonamide salts substituted at the para position with a hydroxycyclooctene substituent. The synthesis involves three steps: 1) a ring opening metathesis polymerization; 2) a hydrogenation; and 3) an ion exchange reaction.
Figure 4:
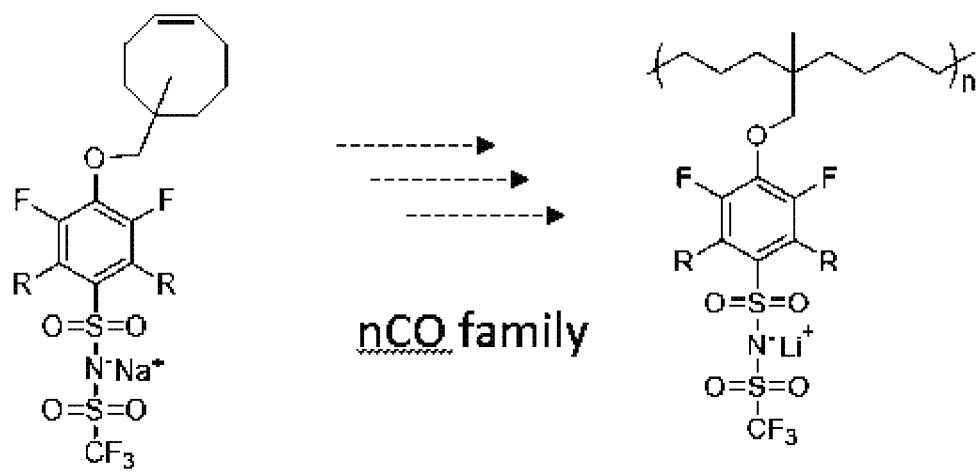
FIG. 4 shows the synthesis of lithium sulfonamide polymer electrolytes from sodium sulfonamide salts substituted at the para position with a methylcyclooctene methanol substituent. The synthesis involves three steps: 1) a ring opening metathesis polymerization; 2) a hydrogenation; and 3) an ion exchange reaction.
Figure 5:
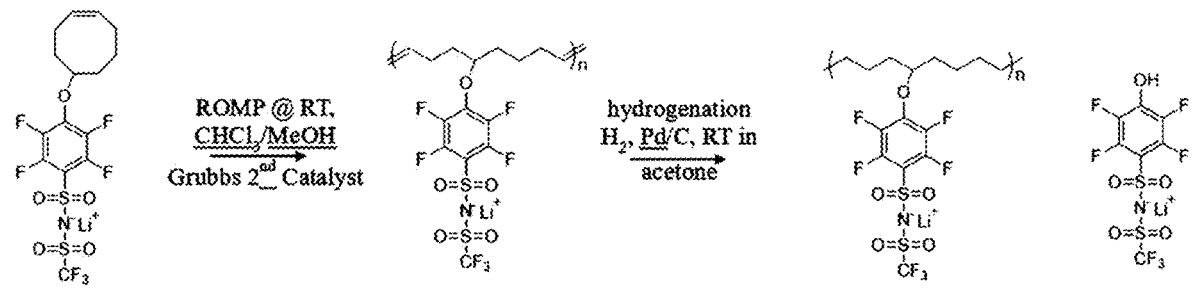
FIG. 5 shows the synthesis of the lithium sulfonamide polymer electrolyte from lithium (Z)-((4-(cyclooct-4-en-1-yloxy)-2,3,5,6 tetrafluorophenyl)sulfonyl)((trifluoromethyl)sulfonyl) amide.
Figure 6:
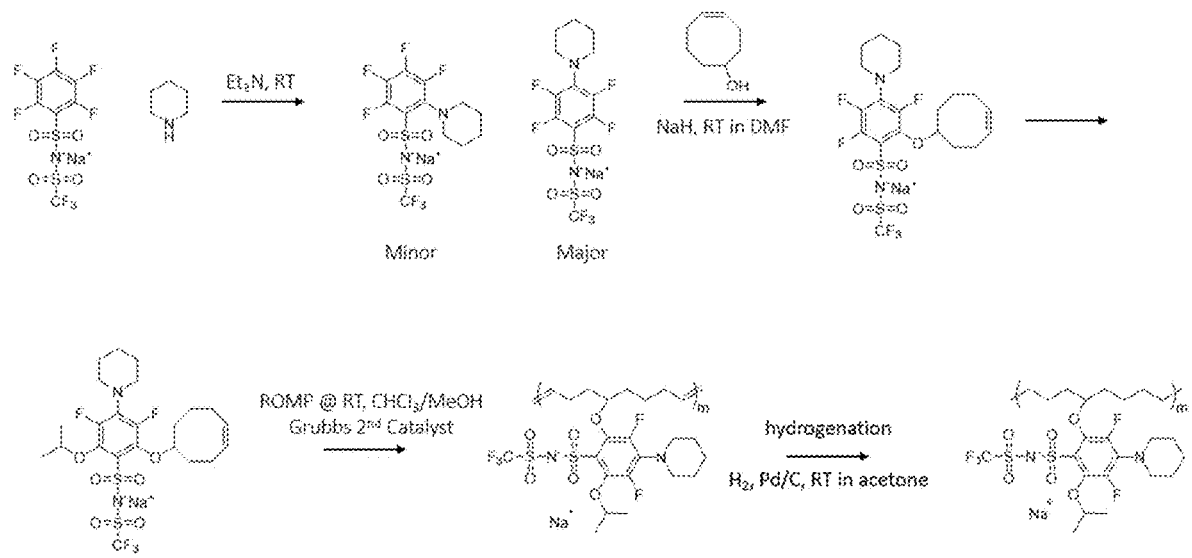
FIG. 6 shows the full synthetic process for the synthesis of sodium polymer electrolyte resulting from sodium ((perfluorophenyl)sulfonyl)((trifluoromethyl)sulfonyl)amide. The synthesis involves three consecutive nucleophilic substitution reactions followed by a ring opening metathesis polymerization and a hydrogenation.
Figure 7:
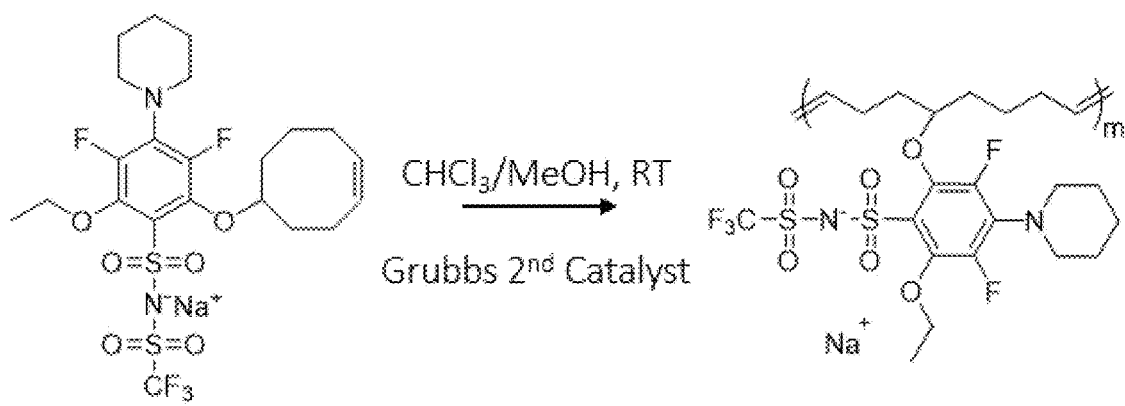
FIG. 7 shows the ring opening metathesis polymerization of sodium (Z)-((2-(cyclooct-4-en-1-yloxy)-6-ethoxy-3,5-difluoro-4-(piperidin-1-yl)phenyl)sulfonyl)((trifluoromethyl)sulfonyl)amide.
Figure 8:
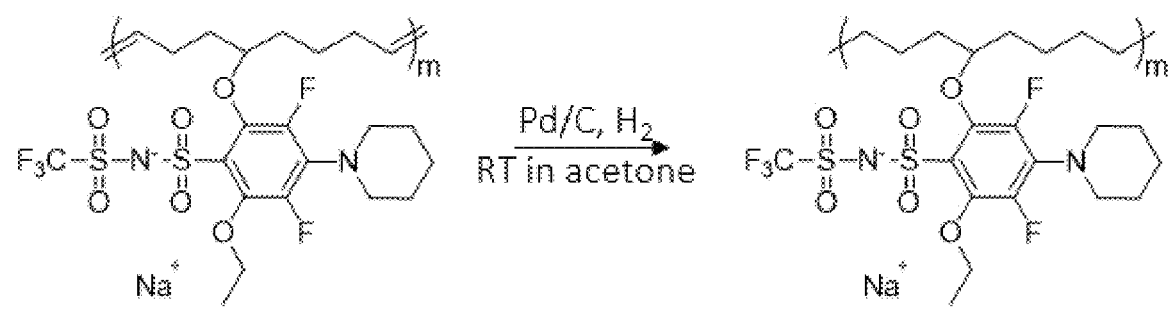
FIG. 8 shows hydrogenation of the product from FIG. 7.
Figure 9:
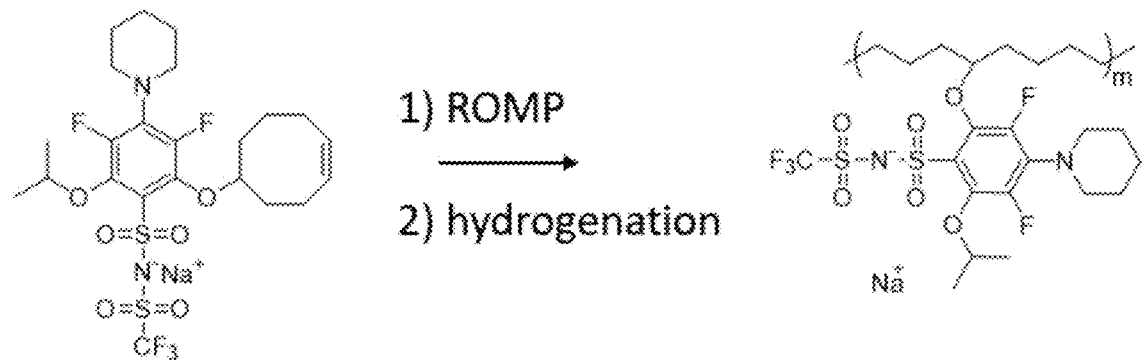
FIG. 9 shows the synthesis of the sodium sulfonamide polymer electrolyte from sodium (Z)-((2-(cyclooct-4-en-1-yloxy)-3,5-difluoro-6-isopropoxy-4-(piperidin-1-yl)phenyl)sulfonyl)((trifluoromethyl)sulfonyl)amide.

For convenience, certain terms employed herein, in the specification, examples and appended claims are collected herein.

Unless otherwise required by context, singular terms shall include pluralities, and plural terms shall include the singular.

The following definitions are more general terms used throughout the present application:

The singular terms "a," "an," and "the" include plural references unless the context clearly indicates otherwise. Similarly, the word "or" is intended to include "and" unless the context clearly indicates otherwise.

Other than in the examples, or where otherwise indicated, all numbers expressing quantities of ingredients or reaction conditions used herein should be understood as modified in all instances by the term "about." "About" and "approximately" shall generally mean an acceptable degree of error for the quantity measured given the nature or precision of the measurements. Exemplary degrees of error are within 20 percent (%), typically, within 10%, or more typically, within 5%, 4%, 3%, 2% or 1% of a given value or range of values.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5$^{th}$ Edition, John Wiley & Sons, Inc., New York, 2001; Larock, Comprehensive Organic Transformations, VCH Publishers, Inc., New York, 1989; and Carruthers, Some Modern Methods of Organic Synthesis, 3$^{rd}$ Edition, Cambridge University Press, Cambridge, 1987.

Compounds described herein can include one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L., Stereochemistry of Carbon Compounds (McGraw-Hill, N Y, 1962); and Wilen, S. H. Tables of Resolving Agents and Optical Resolutions, p. 268 (E. L. Eliel, Ed., Univ. of Notre Dame Press, Notre Dame, Ind. 1972). The disclosure additionally encompasses compounds as individual isomers substantially free of other isomers, and alternatively, as mixtures of various isomers.

In a formula, ⁓ is a single bond where the stereochemistry of the moieties immediately attached thereto is not specified, --- is absent or a single bond, and === or ≡≡≡ is a single or double bond.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The term "aliphatic" includes both saturated and unsaturated, straight chain (i.e., unbranched), branched, acyclic, cyclic, or polycyclic aliphatic hydrocarbons, which are optionally substituted with one or more functional groups. Likewise, the term "heteroaliphatic" refers to heteroalkyl, heteroalkenyl, heteroalkynyl, and heterocyclic groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-100 aliphatic carbon atoms. In certain other embodiments, the alkyl, alkenyl, and alkynyl groups employed in the disclosure contain 1-50 aliphatic carbon atoms. In certain other embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, npropyl, isopropyl, cyclopropyl, —CH$_2$-cyclopropyl, vinyl, allyl, n-butyl, sec-butyl, isobutyl, tertbutyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group. In some embodiments, an alkyl group has 1 to 1000 carbon atoms ("$C_1$-$C_{1000}$ alkyl"), 1 to 900 carbon atoms ("$C_1$-$C_{900}$ alkyl"), 1 to 800 carbon atoms ("$C_1$-$C_{800}$ alkyl"), 1 to 700 carbon atoms ("$C_1$-$C_{700}$ alkyl"), 1 to 600 carbon atoms ("$C_1$-$C_{600}$ alkyl"), 1 to 500 carbon atoms ("$C_1$-$C_{500}$ alkyl"), 1 to 400 carbon atoms ("$C_1$-$C_{400}$ alkyl"), 1 to 300 carbon atoms ("$C_1$-$C_{300}$ alkyl"), 1 to 200 carbon atoms ("$C_1$-$C_{200}$ alkyl"), 1 to 100 carbon atom ("$C_1$-$C_{100}$ alkyl"). In some embodiments, an alkyl group has 1 to 10 carbon atoms ("$C_1$-$C_{10}$ alkyl"), 1 to 9 carbon atoms ("$C_1$-$C_9$ alkyl"), 1 to 8 carbon atoms ("$C_1$-$C_8$ alkyl"), 1 to 7 carbon atoms ("$C_1$-$C_7$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$ alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents.

The term "alkenyl" refers to a radical of a straight-chain or branched hydrocarbon group having from 2 to 1000 carbon atoms and one or more carbon-carbon double bonds (e.g., 1, 2, 3, or 4 double bonds). In some embodiments, an alkenyl group has 2 to 1000 carbon atoms ("$C_2$-$C_{1000}$ alkenyl"), 2 to 900 carbon atoms ("$C_2$-$C_{900}$ alkenyl"), 2 to 800 carbon atoms ("$C_2$-$C_{800}$ alkenyl"), 2 to 700 carbon atoms ("$C_2$-$C_{700}$ alkenyl"), 2 to 600 carbon atoms ("$C_2$-$C_{600}$ alkenyl"), 2 to 500 carbon atoms ("$C_2$-$C_{500}$ alkenyl"), 2 to 400 carbon atoms ("$C_2$-$C_{400}$ alkenyl"), 2 to 300 carbon atoms ("$C_2$-$C_{300}$ alkenyl"), 2 to 200 carbon atoms ("$C_2$-$C_{200}$ alkenyl"), 2 to 100 carbon atom ("$C_2$-$C_{100}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Unless otherwise specified, each instance of an alkenyl group is independently unsubstituted (an "unsubstituted alkenyl") or substituted (a "substituted alkenyl") with one or more substituents. In an alkenyl group, a C=C double bond for which the stereochemistry is not specified (e.g., —CH=CHCH$_3$,

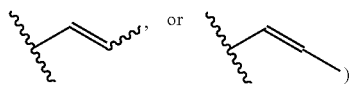

may be in the (E)- or (Z)-configuration.

The term "alkynyl" refers to a radical of a straight-chain or branched hydrocarbon group having from 2 to 1000 carbon atoms and one or more carbon-carbon triple bonds (e.g., 1, 2, 3, or 4 triple bonds). In some embodiments, an alkynyl group has 2 to 1000 carbon atoms ("$C_2$-$C_{1000}$ alkynyl"), 2 to 900 carbon atoms ("$C_2$-$C_{900}$ alkynyl"), 2 to 800 carbon atoms ("$C_2$-$C_{800}$ alkynyl"), 2 to 700 carbon atoms ("$C_2$-$C_{700}$ alkynyl"), 2 to 600 carbon atoms ("$C_2$-$C_{600}$ alkynyl"), 2 to 500 carbon atoms ("$C_2$-$C_{500}$ alkynyl"), 2 to 400 carbon atoms ("$C_2$-$C_{400}$ alkynyl"), 2 to 300 carbon atoms ("$C_2$-$C_{300}$ alkynyl"), 2 to 200 carbon atoms ("$C_2$-$C_{200}$ alkynyl"), 2 to 100 carbon atom ("$C_2$-$C_{100}$ alkynyl"). In some embodiments, an alkynyl group has 2 to 9 carbon atoms ("$C_{2-9}$ alkynyl"), 2 to 8 carbon atoms ("$C_{2-8}$ alkynyl"), 2 to 7 carbon atoms ("$C_{2-7}$ alkynyl"), 2 to 6 carbon atoms ("$C_{2-6}$ alkynyl"), 2 to 5 carbon atoms ("$C_{2-5}$ alkynyl"), 2 to 4 carbon atoms ("$C_{2-4}$ alkynyl"), 2 to 3 carbon atoms ("$C_{2-3}$ alkynyl"), or 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Unless otherwise specified, each instance of an alkynyl group is independently unsubstituted (an "unsubstituted alkynyl") or substituted (a "substituted alkynyl") with one or more substituents.

The term "heteroalkyl" refers to an alkyl group which further includes at least one heteroatom (e.g., 1, 2, 3, or 4 heteroatoms) selected from oxygen, nitrogen, phosphorus, or sulfur within (i.e., inserted between adjacent carbon atoms of) and/or placed at one or more terminal position(s) of the parent chain. In certain embodiments, a heteroalkyl group refers to a saturated group having from 1 to 1000 carbon atoms and 1 or more heteroatoms within the parent chain ("$C_1$-$C_{1000}$ heteroalkyl"), 1 to 900 carbon atoms and 1 or more heteroatoms within the parent chain ("$C_1$-$C_{900}$ heteroalkyl"), 1 to 800 carbon atoms and 1 or more heteroatoms within the parent chain ("$C_1$-$C_{800}$ heteroalkyl"), 1 to 700 carbon atoms and 1 or more heteroatoms within the parent chain ("$C_1$-$C_{700}$ heteroalkyl"), 1 to 600 carbon atoms and 1 or more heteroatoms within the parent chain ("$C_1$-$C_{600}$ heteroalkyl"), 1 to 500 carbon atoms and 1 or more heteroatoms within the parent chain ("$C_1$-$C_{500}$ heteroalkyl"), 1 to 400 carbon atoms and 1 or more heteroatoms within the parent chain ("$C_1$-$C_{400}$ heteroalkyl"), 1 to 300 carbon atoms and 1 or more heteroatoms within the parent chain ("$C_1$-$C_{300}$ heteroalkyl"), 1 to 200 carbon atoms and 1 or more heteroatoms within the parent chain ("$C_1$-$C_{200}$ heteroalkyl"), or 1 to 100 carbon atoms and 1 or more heteroatoms within the parent chain ("$C_1$-$C_{100}$ heteroalkyl"). In certain embodiments, a heteroalkyl group refers to a saturated group having from 1 to 10 carbon atoms and 1 or more heteroatoms within the parent chain ("$C_1$-$C_{10}$ heteroalkyl"), 1 to 9 carbon atoms and 1 or more heteroatoms within the parent chain ("$C_1$-$C_9$ heteroalkyl"), 1 to 8 carbon atoms and 1 or more heteroatoms within the parent chain ("$C_1$-$C_8$ heteroalkyl"), 1 to 7 carbon atoms and 1 or more heteroatoms within the parent chain ("$C_1$-$C_7$ heteroalkyl"), 1 to 6 carbon atoms and 1 or more heteroatoms within the parent chain ("$C_1$-$C_6$ heteroalkyl"), 1 to 5 carbon atoms and 1 or more heteroatoms within the parent chain ("$C_1$-$C_5$ heteroalkyl"), 1 to 4 carbon atoms and 1 or more heteroatoms within the parent chain ("$C_1$-$C_4$ heteroalkyl"), 1 to 3 carbon atoms and 1 or more heteroatoms within the parent chain ("$C_1$-$C_3$ heteroalkyl"), 1 to 2 carbon atoms and 1 heteroatom within the parent chain ("$C_1$-$C_2$ heteroalkyl"), or 1 carbon atom and 1 heteroatom ("$C_1$ heteroalkyl"). Unless otherwise specified, each instance of a heteroalkyl group is independently unsubstituted (an "unsubstituted heteroalkyl") or substituted (a "substituted heteroalkyl") with one or more substituents.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a saturated group having from 1 to 1000 carbon atoms and 1 or more heteroatoms within the parent chain ("heteroC$_1$-C$_{1000}$ alkenyl"), 1 to 900 carbon atoms and 1 or more heteroatoms within the parent chain ("heteroC$_1$-C$_{900}$ alkenyl"), 1 to 800 carbon atoms and 1 or more heteroatoms within the parent chain ("heteroC$_1$-C$_{800}$ alkenyl"), 1 to 700 carbon atoms and 1 or more heteroatoms within the parent chain ("heteroC$_1$-C$_{700}$ alkenyl"), 1 to 600 carbon atoms and 1 or more heteroatoms within the parent chain ("heteroC$_1$-C$_{600}$ alkenyl"), 1 to 500 carbon atoms and 1 or more heteroatoms within the parent chain ("heteroC$_1$-C$_{500}$ alkenyl"), 1 to 400 carbon atoms and 1 or more heteroatoms within the parent chain ("heteroC$_1$-C$_{400}$ alkenyl"), 1 to 300 carbon atoms and 1 or more heteroatoms within the parent chain ("heteroC$_1$-C$_{300}$ alkenyl"), 1 to 200 carbon atoms and 1 or more heteroatoms within the parent chain ("heteroC$_1$-C$_{200}$ alkenyl"), or 1 to 100 carbon atoms and 1 or more heteroatoms within the parent chain ("heteroC$_1$-C$_{100}$ alkenyl"). In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a saturated group having from 1 to 1000 carbon atoms and 1 or more heteroatoms within the parent chain ("heteroC$_1$-C$_{1000}$ alkynyl"), 1 to 900 carbon atoms and 1 or more heteroatoms within the parent chain ("heteroC$_1$-C$_{900}$ alkynyl"), 1 to 800 carbon atoms and 1 or more heteroatoms within the parent chain ("heteroC$_1$-C$_{800}$ alkynyl"), 1 to 700 carbon atoms and 1 or more heteroatoms within the parent chain ("heteroC$_1$-C$_{700}$ alkynyl), 1 to 600 carbon atoms and 1 or more heteroatoms within the parent chain ("heteroC$_1$-C$_{600}$ alkynyl"), 1 to 500 carbon atoms and 1 or more heteroatoms within the parent chain ("heteroC$_1$-C$_{500}$ alkynyl"), 1 to 400 carbon atoms and 1 or more heteroatoms within the parent chain ("heteroC$_1$-C$_{400}$ alkynyl"), 1 to 300 carbon atoms and 1 or more heteroatoms within the parent chain ("heteroC$_1$-C$_{300}$ alkynyl"), 1 to 200 carbon atoms and 1 or more heteroatoms within the parent chain ("heteroC$_1$-C$_{200}$ alkynyl"), or 1 to 100 carbon atoms and 1 or more heteroatoms within the parent chain ("heteroC$_1$-C$_{100}$ alkynyl"). In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" or "cycloalkyl" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"), 3 to 7 ring carbon atoms ("C$_{3-7}$ carbocyclyl"), 3 to 6 ring carbon atoms ("C$_{3-6}$ carbocyclyl"), 4 to 6 ring carbon atoms ("C$_{4-6}$ carbocyclyl"), 5 to 6 ring carbon atoms ("C$_{5-6}$ carbocyclyl"), or 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, phosphorus, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, "heterocyclyl" also includes rings systems wherein the rings systems are saturated or unsaturated.

In some embodiments, a heterocyclyl group is a 5-10 membered non-aromatic ring system having ring carbon atoms and 1-4 ring heteroatoms, wherein each heteroatom is independently selected from nitrogen, oxygen, phosphorus, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorus, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorus, and sulfur ("5-6 membered heterocyclyl"). In some embodiments, the 5-6 membered heterocyclyl has 1-3 ring heteroatoms selected from nitrogen, oxygen, phosphorus, and sulfur. In some embodiments, the 5-6 membered heterocyclyl has 1-2 ring heteroatoms selected from nitrogen, oxygen, phosphorus, and sulfur. In some embodiments, the 5-6 membered heterocyclyl has 1 ring heteroatom selected from nitrogen, oxygen, phosphorus, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl, and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 r electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents.

The term "heteroaryl" refers to a radical of a 5-14 membered monocyclic or polycyclic (e.g., bicyclic, tricyclic) 4n+2 aromatic ring system (e.g., having 6, 10, or 14 r electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group be monovalent or may have more than one point of attachment to another moiety (e.g., it may be divalent, trivalent, etc), although the valency may be specified directly in the name of the group. For example, "triazoldiyl" refers to a divalent triazolyl moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As understood from the above, alkyl, alkenyl, alkynyl, carbocyclyl, aryl, and heteroaryl groups are, in certain embodiments, optionally substituted. Optionally substituted refers to a group which may be substituted or unsubstituted (e.g., "substituted" or "unsubstituted" alkyl). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Affixing the suffix "ene" to a group indicates the group is a polyvalent (e.g., bivalent, trivalent, tetravalent, or pentavalent) moiety. In certain embodiments, affixing the suffix "ene" to a group indicates the group is a bivalent moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion. In certain embodiments, none of R$^{aa}$ to R$^{gg}$ comprise X$^-$.

In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$. In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, or —NO$_2$.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), P-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH.

The term "thiol" or "thio" refers to the group —SH.

The term "amine" or "amino" refers to the group —NH— or —$NH_2$.

The term "acyl" refers to a group having the general formula —$C(=O)R^{X1}$, —$C(=O)OR^{X1}$, —$C(=O)$—O—$C(=O)R^{X1}$, —$C(=O)SR^{X1}$, —$C(=O)N(R^{X1})_2$, —$C(=S)R^{X1}$, —$C(=S)N(R^{X1})_2$, and —$C(=S)S(R^{X1})$, —$C(=NR^{X1})R^{X1}$, —$C(=NR^{X1})OR^{X1}$, —$C(=NR^{X1})SR^{X1}$, and —$C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "polymer" refers to a molecule including two or more (e.g., 3 or more, 4 or more, 5 or more, 10 or more) repeating units which are covalently bound together. In certain embodiments, a polymer comprises 3 or more, 5 or more, 10 or more, 50 or more, 100 or more, 500 or more, 1000 or more, 2000 or more, 3000 or more, 4000 or more, 5000 or more, 6000 or more, 7000 or more, 8000 or more, 9000 or more, or 10000 or more repeating units. In certain embodiments, a polymer comprises more than 5000 repeating units. The repeating units of a polymer are referred to as "monomers." A "homopolymer" is a polymer that consists of a single repeating monomer. A "copolymer" is a polymer that comprises two or more different monomer subunits. Copolymers include, but are not limited to, random, block, alternating, segmented, linear, branched, grafted, and tapered copolymers. A "graft polymer" is a segmented copolymer with a linear backbone of one composite and randomly distributed branches of another composite. The major difference between graft polymers and bottlebrush polymers (or brush-arm polymers) is the grafting density. The targeted graft density for bottlebrush polymers is that in at least one segment of the copolymer is one graft from each backbone monomer unit. A "star polymer" is a polymer that consists of several polymers chains connected at a core atom, core molecule, or core polymer. Polymers may be natural (such as biopolymers like naturally occurring polypeptides), or synthetic (e.g., non-naturally occurring). A polymer may have an overall molecular weight of 50 Da or greater, 100 Da or greater, 500 Da or greater, 1000 Da or greater, 2000 Da or greater, 5000 Da or greater, 10000 Da or greater, 20000 Da or greater, or 50000 Da or greater.

The terms "living polymer" and "living polymerization" refer a polymerization where the ability of a growing polymer chain to terminate has been removed. Chain termination and chain transfer reactions are absent, and the rate of the chain initiation is also much larger than the rate of chain propagation.

The term "average molecular weight" may encompass the number average molecular weight ($M_n$), weight average molecular weight ($M_w$), higher average molecular weight ($M_z$ or $M_z+1$), GPC/SEC (gel permeation chromatography/size-exclusion chromatography)-determined average molecular weight ($M_p$), and viscosity average molecular weight ($M_v$).

The terms "number average molecular weight," "number average molar mass," and "$M_n$" are measurements of the molecular mass of a polymer. The number average molecular mass is the ordinary arithmetic mean or average of the molecular masses of the individual polymers. It is determined by measuring the molecular mass of n polymer molecules, summing the masses, and dividing by n. For example, a polymer having 100 repeating units of a monomer with a molecular weight of 100 g/mol would have a number average molecular weight ($M_n$) of 10,000 g/mol [$M_n$=(100)*(100 g/mol)/(1)=10,000 g/mol)]. The number average molecular mass of a polymer can be determined by gel permeation chromatography, viscometry via the Mark-Houwink equation, colligative methods such as vapor pressure osmometry, end-group determination, or $^1$H NMR (nuclear magnetic resonance).

The term "monomer" refers to a molecule that may be covalently joined to other monomers to form a polymer. The process by which the monomers are combined to form a polymer is called polymerization. A macromolecule with a reactive moiety that enables it to act as a monomer is called a macromonomer. Molecules made of a small number of monomer units (up to a few dozen) are called oligomers.

The term "average hydrodynamic diameter" ($D_H$) as used herein refers to the average size of a conjugate or particle. The average hydrodynamic diameter may or may not encompass the solvation layers of conjugate or particle, and may be determined through a number of methods including dynamic light scattering, electron microscopy (e.g., scanning electron microscopy, transmission electron microscopy), atomic force microscopy, and X-ray diffraction.

The term "average polydispersity" (PDI) as used herein refers to a measure of the distribution of molecular size in a mixture, e.g., as determined by a chromatographic method, such as gel permeation chromatography or size exclusion chromatography, or through dynamic light scattering.

As used herein, the term "polyethylene glycol" or "PEG" refers to an ethylene glycol polymer that contains about 20 to about 2,000,000 linked monomers, typically about 50-1,000 linked monomers, usually about 100-300. Polyethylene glycols include ethylene glycol polymer containing various numbers of linked monomers, e.g., PEG20, PEG30, PEG40, PEG60, PEG80, PEG100, PEG115, PEG200, PEG300, PEG400, PEG500, PEG600, PEG1000, PEG1500, PEG2000, PEG3350, PEG4000, PEG4600, PEG5000, PEG6000, PEG8000, PEG11000, PEG12000, PEG2000000, and any mixtures thereof.

The term "polyelectrolyte" or "polymer electrolyte" refers to polymers whose repeating units bear an electrolyte group. Polycations and polyanions are polyelectrolytes. These groups dissociate in polar solvents, such as water, making the polymers charged. Polyelectrolyte properties are thus similar to both electrolytes (salts) and polymers (high molecular weight compounds) and are sometimes called polysalts. Like salts, their solutions are often viscous. Charged molecular chains, commonly present in soft matter systems, play a fundamental role in determining structure, stability, and the interactions of various molecular assemblies. Theoretical approaches to describing their statistical properties differ profoundly from those of their electrically neutral counterparts, while technological and industrial fields exploit their unique properties. Many biological molecules are polyelectrolytes. For instance, polypeptides, glycosaminoglycans, and DNA are polyelectrolytes. Both natural and synthetic polyelectrolytes are used in a variety of industries.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this disclosure include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "leaving group" is given its ordinary meaning in the art of synthetic organic chemistry and refers to an atom or a group capable of being displaced by a nucleophile. Examples of suitable leaving groups include halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other examples of leaving groups are water, ammonia, alcohols, ether moieties, thioether moieties, zinc halides, magnesium moieties, diazonium salts, and copper moieties.

The term "solvent" refers to a substance that dissolves one or more solutes, resulting in a solution. A solvent may serve as a medium for any reaction or transformation described herein. The solvent may dissolve one or more reactants or reagents in a reaction mixture. The solvent may facilitate the mixing of one or more reagents or reactants in a reaction mixture. The solvent may also serve to increase or decrease the rate of a reaction relative to the reaction in a different solvent. Solvents can be polar or non-polar, protic or aprotic. Common solvents useful in the methods described herein include, but are not limited to, acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-dimethylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), nitromethane, 1-octanol, pentane, 3-pentanone, 1-propanol, 2-propanol, pyridine, tetrachloroethylene, tetrahydrofuran (THF), 2-methyltetrahydrofuran, toluene, trichlorobenzene, 1,1,2-trichlorotrifluoroethane, 2,2,4-trimethylpentane, trimethylamine, triethylamine, N,N-diisopropylethylamine, diisopropylamine, water, o-xylene, and p-xylene.

As used herein, the term "agent" means a molecule, group of molecules, complex or substance administered to an organism for diagnostic, therapeutic, preventative medical, or veterinary purposes. In certain embodiments, the agent is a pharmaceutical agent (e.g., a therapeutic agent, a diagnostic agent, or a prophylactic agent). In certain embodiments, the compositions disclosed herein comprise an agent(s), e.g., a first therapeutic agent (e.g., at least one (including, e.g., at least two, at least three). In some embodiments, the compositions (e.g., macromonomers, conjugates, or particles) can further comprise a second therapeutic agent, a targeting moiety, a diagnostic moiety as described herein.

As used herein, the term "therapeutic agent" includes an agent that is capable of providing a local or systemic biological, physiological, or therapeutic effect in the biological system to which it is applied. For example, a therapeutic agent can act to control tumor growth, control infection or inflammation, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism.

An agent (e.g., a therapeutic agent) can include a wide variety of different compounds, including chemical compounds and mixtures of chemical compounds (e.g., small organic or inorganic molecules) such as drug compounds (e.g., compounds approved for human or veterinary use by the U.S. Food and Drug Administration as provided in the Code of Federal Regulations (CFR)); targeting agents; isotopically labeled chemical compounds; agents useful in bioprocessing; carbohydrates; saccharines; monosaccharides; oligosaccharides; polysaccharides; biological macromolecules (e.g., peptides, proteins, and peptide analogs and derivatives); peptidomimetics; antibodies and antigen binding fragments thereof; nucleic acids (e.g., DNA or RNA); nucleotides; nucleosides; oligonucleotides; antisense oligonucleotides; polynucleotides; nucleic acid analogs and derivatives; nucleoproteins; mucoproteins; lipoproteins; synthetic polypeptides or proteins; small molecules linked to proteins; glycoproteins; steroids; lipids; hormones; vitamins; vaccines; immunological agents; an extract made from biological materials such as bacteria, plants, fungi, or animal cells; animal tissues; naturally occurring or synthetic compositions; and any combinations thereof.

In some embodiments, the agent is in the form of a prodrug. The term "prodrug" refer to a compound that becomes active, e.g., by solvolysis, reduction, oxidation, or under physiological conditions, to provide a pharmaceutically active compound, e.g., in vivo. A prodrug can include a derivative of a pharmaceutically active compound, such as, for example, to form an ester by reaction of the acid, or acid anhydride, or mixed anhydrides moieties of the prodrug moiety with the hydroxyl moiety of the pharmaceutical active compound, or to form an amide prepared by the acid, or acid anhydride, or mixed anhydrides moieties of the prodrug moiety with a substituted or unsubstituted amine of the pharmaceutically active compound. Simple aliphatic or aromatic esters, amides, and anhydrides derived from acidic groups may comprise prodrugs. In some embodiments, the conjugate or particle described herein incorporates one therapeutic agent or prodrug thereof. In some embodiments, the conjugate or particle described herein incorporates more than one therapeutic agents or prodrugs.

In some embodiments, the agent (e.g., a therapeutic agent) is a small molecule. As used herein, the term "small molecule" can refer to compounds that are "natural product-like." However, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary agents (e.g., a therapeutic agents) in the compositions include, but are not limited to, those found in *Harrison's Principles of Internal Medicine,* 13th Edition, Eds. T. R. Harrison et al. McGraw-Hill N.Y., NY; Physicians' Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

In some embodiments, exemplary therapeutic agents in the compositions include, but are not limited to, one or more of the agents listed in Paragraph 0148 of U.S. Pat. No. 9,381,253, incorporated by reference herein.

In other embodiments, exemplary therapeutic agents in the compositions include, but are not limited to, one or more of the therapeutic agents listed in WO 2013/169739, including the anti-hypertensive and/or a collagen modifying agents ("AHCM") disclosed, e.g., in Paragraphs 40-49, 283, 286-295; the microenvironment modulators disclosed, e.g., in Paragraphs 113-121, of WO 2013/169739, incorporated herein by reference. In some embodiments, the composition comprising the AHCM and/or the microenvironment modulator causes one or more of: reduces solid stress (e.g., growth-induced solid stress in tumors); decreases tumor fibrosis; reduces interstitial hypertension or interstitial fluid pressure (IFP); increases interstitial tumor transport; increases tumor or vessel perfusion; increases vascular diameters and/or enlarges compressed or collapsed blood vessels; reduces or depletes one or more of: cancer cells, or stromal cells (e.g., tumor associated fibroblasts or immune cells); decreases the level or production of extracellular matrix components, such as fibers (e.g., collagen, procollagen), and/or polysaccharides (e.g., glycosaminoglycans such as hyaluronan or hyaluronic acid); decreases the level or production of collagen or procollagen; decreases the level or production of hyaluronic acid; increases tumor oxygenation; decreases tumor hypoxia; decreases tumor acidosis; enables immune cell infiltration; decreases immunosuppression; increases antitumor immunity; decreases the production of cancer stem cells (also referred to herein as tumor-initiating cells); or enhances the efficacy (e.g., penetration or diffusion), of the therapy, e.g., the cancer therapy (e.g., radiation, photodynamic therapy, chemotherapeutics and immunotherapies) in a tumor or tumor vasculature, in the subject.

Agents, e.g., therapeutic agents, include the herein disclosed categories and specific examples. It is not intended that the category be limited by the specific examples. Those of ordinary skill in the art will recognize also numerous other compounds that fall within the categories and that are useful according to the present disclosure.

Examples of therapeutic agents include, but are not limited to, antimicrobial agents, analgesics, antiinflammatory agents, counterirritants, coagulation modifying agents, diuretics, sympathomimetics, anorexics, antacids and other gastrointestinal agents; antiparasitics, antidepressants, anti-hypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anti-cancer properties, or a combination thereof. Other suitable therapeutic agents include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; anti-hypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

In certain instances, the diagnostic agent is an imaging agent or contrast agent. The terms "imaging agent" and "contrast agent" refer to a substance used to enhance the contrast of structures or fluids within the body in medical imaging. It is commonly used to enhance the visibility of blood vessels and the gastrointestinal tract in medical imaging.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

An "effective amount" of a composition described herein refers to an amount sufficient to elicit the desired biological response. An effective amount of a composition described herein may vary depending on such factors as the desired biological endpoint, the pharmacokinetics of the composition, the condition being treated, the mode of administration, and the age and health of the subject. In certain embodiments, an effective amount is a therapeutically effective amount. In certain embodiments, an effective amount is a prophylactically effective amount. In certain embodiments, an effective amount is the amount of a composition or pharmaceutical composition described herein in a single dose. In certain embodiments, an effective amount is the combined amounts of a composition or pharmaceutical composition described herein in multiple doses.

A "therapeutically effective amount" of a composition described herein is an amount sufficient to provide a therapeutic benefit in the treatment of a condition or to delay or minimize one or more symptoms associated with the condition. A therapeutically effective amount of a composition means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a composition described herein is an amount sufficient to prevent a condition, or one or more symptoms associated with the condition or prevent its recurrence. A prophylactically effective amount of a composition means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "biocompatible" or "biocompatibility" refers to the ability of a material to perform with an appropriate host response in a specific situation. In particular, the terms refer to the ability of a biomaterial to perform its desired function with respect to a medical therapy without eliciting any undesirable local or systematic effects in the recipient or beneficiary of that therapy, but generating the most appropriate beneficial cellular or tissue response in that specific situation, and optimizing the clinically relevant performance of that therapy.

The term "nucleophilic aromatic substitution" refers to a substitution reaction in organic chemistry in which a nucleophile displaces a leaving group, such as a halide, on an aromatic ring.

The term "initiator" refers to a chemical compound that can produce radical species and/or promote radical reactions. Common initiators useful in the methods and systems described herein include, but are not limited to, azobisisobutyronitrile, 1,1'-azobis(cyclohexanecarbonitrile), di-tert-butyl peroxide, benzoyl peroxide, methyl ethyl ketone peroxide, acetone peroxide, sodium persulfate, potassium persulfate, ammonium persulfate, ethyl 2-bromo-2-phenylacetate, dodecyl 2-bromoisobutyrate, ethyl 2-bromoisobutyrate, ethyl 2-bromopropionate, 2-hydroxyethyl 2-bromoisobutyrate, and octadecyl 2-bromoisobutyrate.

The term "iniferter" refers to a chemical compound that simultaneously acts as a initiator, transfer agent, and terminator. Common iniferters useful in the methods described herein include, but are not limited to, benzyl benzodithioate, cyanomethyl benzodithioate, 4-cyano-4-(phenylcarbonothioylthio)pentanoic acid, 4-cyano-4-(phenylcarbonothioylthio)pentanoic acid N-succinimidyl ester, 2-cyano-2-propyl benzodithioate, 2-cyano-2-propyl 4-cyanobenzodithioate, ethyl 2-(4-methoxyphenylcarbonothioylthio)acetate, ethyl 2-methyl-2-(phenylthiocarbonylthio)propionate, ethyl 2-(phenylcarbonothioylthio)-2-phenylacetate, ethyl 2-(phenylcarbonothioylthio)propionate, 1-(methoxycarbonyl)ethyl benzodithioate, 2-(4-methoxyphenylcarbonothioylthio)ethanoic acid, 2-nitro-5-(2-propynyloxy)benzyl 4-cyano-4-(phenylcarbonothioylthio)pentanoate, 2-(phenylcarbonothioylthio)propanoic acid, 2-phenyl-2-propyl benzodithioate, 3,5-Bis(2-dodecylthiocarbonothioylthio-1-oxopropoxy)benzoic acid, 2-cyanobutan-2-yl 4-chloro-3,5-dimethyl-1H-pyrazole-1-carbodithioate, 2-cyanobutanyl-2-yl 3,5-dimethyl-1H-pyrazole-1-carbodithioate, 4-cyano-4-[(dodecylsulfanylthiocarbonyl)sulfanyl]pentanoic acid, 4-cyano-4-[(dodecylsulfanylthiocarbonyl)sulfanyl]pentanol, cyanomethyl (3,5-dimethyl-1H-pyrazole)-carbodithioate, cyanomethyl dodecyl trithiocarbonate, cyanomethyl [3-(trimethoxysilyl)propyl]trithiocarbonate, 2-cyano-2-propyl dodecyl trithiocarbonate, S,S-dibenzyl trithiocarbonate, 2-(dodecylthiocarbonothioylthio)propionic acid, 2-(dodecylthiocarbonothioylthio)-2-methylpropionic acid 3-azido-1-propanol ester, 2-(dodecylthiocarbonothioylthio)-2-methylpropionic acid N-hydroxysuccinimide ester, 2-(dodecylthiocarbonothioylthio)-2-methylpropionic acid pentafluorophenyl ester, phthalimidomethyl butyl trithiocarbonate, methyl 2-(dodecylthiocarbonothioylthio)-2-methylpropionate, 2,2'-(thiocarbonylbis(sulfanediyl))bis(2-methylpropanoic acid), dibenzyl 2,2'-(thiocarbonylbis(sulfanediyl))bis(2-methylpropanoate), dibenzyl 2,2'-(thiocarbonylbis(sulfanediyl))dipropionate, 2-(((dodecylthio)carbonothioyl)thio)propanoic acid, benzyl 1H-pyrrole-1-carbodithioate, cyanomethyl diphenylcarbamodithioate, cyanomethyl methyl(phenyl)carbamodithioate, cyanomethyl methyl(4-pyridyl)carbamodithioate, 2-cyanopropan-2-yl N-methyl-N-(pyridin-4-yl)carbamodithioate, methyl 2-[methyl(4-pyridinyl)carbamothioylthio]propionate, 1-succinimidyl-4-cyano-4-[N-methyl-N-(4-pyridyl)carbamothioylthio]pentanoate, ethyl 2-(((ethylthio)carbonothioyl)thio)propanoate, methyl (4-methoxyphenoxy)carbonothioylsulfanyl acetate, methyl (methoxycarbonothioyl)sulfanyl acetate, methyl (ethoxycarbonothioyl)sulfanyl acetate, and methyl (isopropoxycarbonothioyl)sulfanyl acetate.

The term "chain transfer agent" refers to a chemical compound that is able to react with a chain carrier by a reaction in which the original chain carrier is deactivated and a new chain carrier is generated. Common chain transfer agents useful in the methods described herein include, but are not limited to, benzyl benzodithioate, cyanomethyl benzodithioate, 4-cyano-4-(phenylcarbonothioylthio)pentanoic acid, 4-cyano-4-(phenylcarbonothioylthio)pentanoic acid N-succinimidyl ester, 2-cyano-2-propyl benzodithioate, 2-cyano-2-propyl 4-cyanobenzodithioate, ethyl 2-(4-methoxyphenylcarbonothioylthio)acetate, ethyl 2-methyl-2-(phenylthiocarbonylthio)propionate, ethyl 2-(phenylcarbonothioylthio)-2-phenylacetate, ethyl 2-(phenylcarbonothioylthio)propionate, 1-(methoxycarbonyl)ethyl benzodithioate, 2-(4-methoxyphenylcarbonothioylthio)ethanoic acid, 2-nitro-5-(2-propynyloxy)benzyl 4-cyano-4-(phenylcarbonothioylthio)pentanoate, 2-(phenylcarbonothioylthio)propanoic acid, 2-phenyl-2-propyl benzodithioate, 3,5-Bis(2-dodecylthiocarbonothioylthio-1-oxopropoxy)benzoic acid, 2-cyanobutan-2-yl 4-chloro-3,5-dimethyl-1H-pyrazole-1-carbodithioate, 2-cyanobutanyl-2-yl 3,5-dimethyl-1H-pyrazole-1-carbodithioate, 4-cyano-4-[(dodecylsulfanylthiocarbonyl)sulfanyl]pentanoic acid, 4-cyano-4-[(dodecylsulfanylthiocarbonyl)sulfanyl]pentanol, cyanomethyl (3,5-dimethyl-1H-pyrazole)-carbodithioate, cyanomethyl dodecyl trithiocarbonate, cyanomethyl [3-(trimethoxysilyl)propyl]trithiocarbonate, 2-cyano-2-propyl dodecyl trithiocarbonate, S,S-dibenzyl trithiocarbonate, 2-(dodecylthiocarbonothioylthio)propionic acid, 2-(dodecylthiocarbonothioylthio)-2-methylpropionic acid 3-azido-1-propanol ester, 2-(dodecylthiocarbonothioylthio)-2-methylpropionic acid N-hydroxysuccinimide ester, 2-(dodecylthiocarbonothioylthio)-2-methylpropionic acid pentafluorophenyl ester, phthalimidomethyl butyl trithiocarbonate, methyl 2-(dodecylthiocarbonothioylthio)-2-methylpropionate, 2,2'-(thiocarbonylbis(sulfanediyl))bis(2-methylpropanoic acid), dibenzyl 2,2'-(thiocarbonylbis(sulfanediyl))bis(2-methylpropanoate), dibenzyl 2,2'-(thiocarbonylbis(sulfanediyl))dipropionate, 2-(((dodecylthio)carbonothioyl)thio)propanoic acid, benzyl 1H-pyrrole-1-carbodithioate, cyanomethyl diphenylcarbamodithioate, cyanomethyl methyl(phenyl)carbamodithioate, cyanomethyl methyl(4-pyridyl)carbamodithioate, 2-cyanopropan-2-yl N-methyl-N-(pyridin-4-yl)carbamodithioate, methyl 2-[methyl(4-pyridinyl)carbamothioylthio] propionate, 1-succinimidyl-4-cyano-4-[N-methyl-N-(4-pyridyl)carbamothioylthio]pentanoate, ethyl 2-(((ethylthio)carbonothioyl)thio)propanoate, methyl (4-methoxyphenoxy)carbonothioylsulfanyl acetate, methyl (methoxycarbonothioyl)sulfanyl acetate, methyl (ethoxycarbonothioyl)sulfanyl acetate, and methyl (isopropoxycarbonothioyl)sulfanyl acetate.

The following definitions are more general terms used throughout the present application.

The term "catalysis," "catalyze," or "catalytic" refers to the increase in rate of a chemical reaction due to the participation of a substance called a "catalyst." In certain embodiments, the amount and nature of a catalyst remains essentially unchanged during a reaction. In certain embodiments, a catalyst is regenerated, or the nature of a catalyst is essentially restored after a reaction. A catalyst may participate in multiple chemical transformations. The effect of a catalyst may vary due to the presence of other substances known as inhibitors or poisons (which reduce the catalytic activity) or promoters (which increase the activity). Catalyzed reactions have lower activation energy (rate-limiting free energy of activation) than the corresponding uncatalyzed reaction, resulting in a higher reaction rate at the same temperature. Catalysts may affect the reaction environment favorably, bind to the reagents to polarize bonds, form specific intermediates that are not typically produced by a uncatalyzed reaction, or cause dissociation of reagents to reactive forms.

The disclosure is not intended to be limited in any manner by the above exemplary listing of substituents. Additional terms may be defined in other sections of this disclosure.

DETAILED DESCRIPTION OF CERTAIN EMBODIMENTS

The present disclosure describes compounds (e.g., sulfonamide salts with polymerizable groups) that can be used to produce polymers (e.g., polymers that bear sulfonamide sidechains and carbon backbones). These compounds (e.g., salts) and polymers are designed to be stable towards chemical reactions such as radical abstraction, deprotonation, electrochemical oxidation, and nucleophilic attack. These polymers have potential applications as components of batteries and other devices that require ion conductivity in harsh chemical and electrochemical environments. Furthermore, the use of fluorinated aryl groups allows for the modular introduction of functionality onto the polymer sidechains through nucleophilic aromatic substitution processes, thus enabling access to a wide array of novel polysulfonamides with variable structures for tuning the glass transition temperature, stability, and other material properties.

Before the disclosed systems, compositions, methods, reagents, and kits are described in more detail, it should be understood that the aspects described herein are not limited to specific embodiments, methods, apparati, or configurations, and as such can, of course, vary. It is also to be understood that the terminology used herein is for the purpose of describing particular aspects only and, unless specifically defined herein, is not intended to be limiting.

Compounds

Compounds in this disclosure are sulfonamide salt monomers, which contain a polymerizable group for polymerization for the preparation of polymer electrolytes.

The present disclosure describes compounds of Formula (I) (monomers) as described herein.

In one aspect, the compound is a compound of Formula (I):

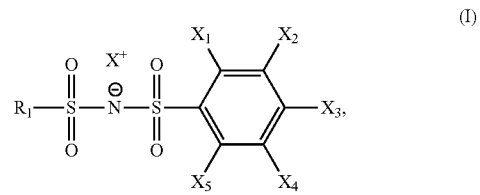

or a salt thereof, wherein:

$R_1$ is optionally substituted alkyl or optionally substituted phenyl;

$X^+$ is a counterion;

$X_1$, $X_2$, $X_3$, $X_4$ and $X_5$ independently is hydrogen; halogen; optionally substituted, cyclic or acyclic alkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; —$OR_2$; —$N(R_3)_2$; or —$SR_2$;

each $R_2$ independently is hydrogen; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; optionally substituted heteroaryl; an oxygen protecting group; or a sulfur protecting group; and each $R_3$ is hydrogen; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; or optionally substituted heteroaryl; a nitrogen protecting group; or two $R_3$ are taken together to form an optionally substituted heterocyclic moiety;

provided that at least one of $X_1$, $X_2$, $X_3$, $X_4$ and $X_5$ comprises optionally substituted, cyclic or acyclic alkenyl; optionally substituted, cyclic or acyclic heteroalkenyl; optionally substituted, cyclic or acyclic alkynyl, or optionally substituted, cyclic or acyclic heteroalkynyl; and at least one of $X_1$, $X_2$, $X_3$, $X_4$ and $X_5$ is halogen; or optionally substituted, cyclic or acyclic alkyl.

In certain embodiments, $R_1$ is optionally substituted haloalkyl. In certain embodiments, $R_1$ is —$CF_3$. In certain embodiments, $R_1$ is fluorinated phenyl.

In certain embodiments, $X^+$ is an inorganic or organic cation. In certain embodiments, $X^+$ is an inorganic cation selected from the group consisting of $Li^+$, $Na^+$, $K^+$, $Rb^+$, $Cs^+$, and $Fr^+$. In certain embodiments, $X^+$ is $Li^+$. In certain embodiments, $X^+$ is $Na^+$. In certain embodiments, $X^+$ is an organic cation. In certain embodiments, salts described herein can be pharmaceutically acceptable salts.

In certain embodiments, between one and four of $X_1$, $X_2$, $X_3$, $X_4$ and $X_5$ are a halogen of haloalkyl group. In certain embodiments, the halogen is fluorine. In certain embodiments, the haloalkyl group is —$CF_3$. In certain embodiments, $X_2$, $X_3$, $X_4$ and $X_5$ are all fluorine. In certain embodiments, $X_1$, $X_2$, $X_4$ and $X_5$ are all fluorine. In certain embodiments, between two and four of $X_1$, $X_2$, $X_3$, $X_4$ and $X_5$ are fluorine. In certain embodiments, $X_2$ and $X_4$ are both fluorine.

In certain embodiments, at least one of $X_1$, $X_3$, and $X_5$ of a compound of Formula (I) is optionally substituted, cyclic or acyclic alkenyl, or optionally substituted, cyclic or acyclic heteroalkenyl.

In certain embodiments, the compound of Formula (I) is of formula:

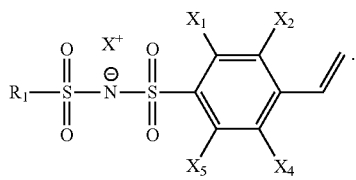

In certain embodiments, the compound of Formula (I) is of formula:

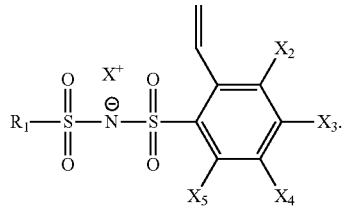

In certain embodiments, the compound of Formula (I) is of formula:

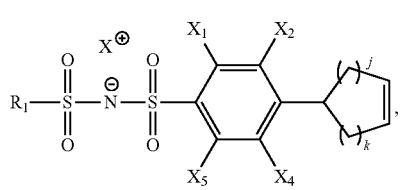

In certain embodiments, the compound of Formula (I) is of formula: wherein: j is an integer between 0 and 3, inclusive; and k is an integer between 0 and 3, inclusive.

In certain embodiments, the compound of Formula (I) is of formula:

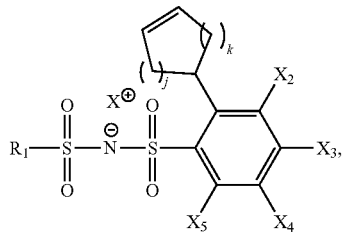

wherein: j is an integer between 0 and 3, inclusive; and k is an integer between 0 and 3, inclusive.

In certain embodiments, at least one of $X_1$, $X_3$, and $X_5$ of a compound of Formula (I) is optionally substituted, cyclic or acyclic alkynyl, or optionally substituted, cyclic or acyclic heteroalkynyl. In certain embodiments, the compound of Formula (I) is of formula:

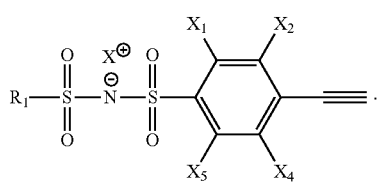

In certain embodiments, the compound of Formula (I) is of formula:

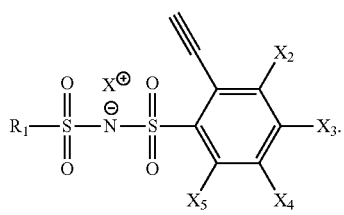

In certain embodiments, the compound of Formula (I) is of formula:

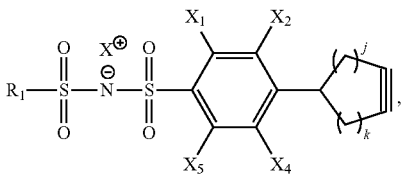

wherein: j is an integer between 0 and 5, inclusive; and k is an integer between 0 and 5, inclusive; provided that the sum of j and k is at least 5. In certain embodiments, the compound of Formula (I) is of formula:

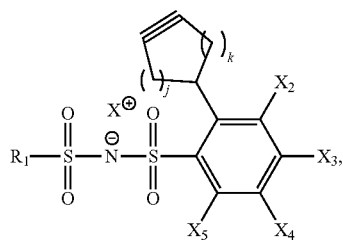

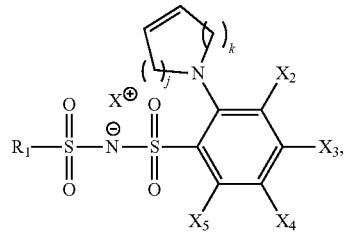

wherein: j is an integer between 0 and 5, inclusive; and k is an integer between 0 and 5, inclusive; provided that the sum of j and k is at least 5.

In certain embodiments, at least one of $X_1$, $X_3$, and $X_5$ of a compound of Formula (I) independently is —$OR_2$, or —$N(R_3)_2$, or —$SR_2$; wherein: each $R_2$ independently is hydrogen; optionally substituted, cyclic or acyclic haloalkyl; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; or optionally substituted heteroaryl; each $R_3$ is hydrogen; optionally substituted, cyclic or acyclic haloalkyl; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; or optionally substituted heteroaryl; or two $R_3$ are taken together to form an optionally substituted cyclic alkenyl or an optionally substituted cyclic alkynyl; provided that at least one of $X_1$, $X_2$, $X_3$, $X_4$ and $X_5$ is optionally substituted, cyclic or acyclic alkenyl; optionally substituted, cyclic or acyclic heteroalkenyl; optionally substituted, cyclic or acyclic alkynyl, or optionally substituted, cyclic or acyclic heteroalkynyl; and at least one of $X_1$, $X_2$, $X_3$, $X_4$ and $X_5$ is halogen; optionally substituted, cyclic or acyclic haloalkyl.

In certain embodiments, the compound of Formula (I) is of formula:

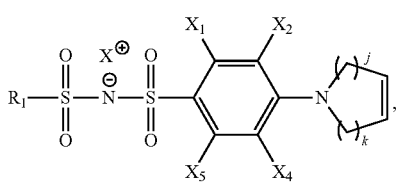

wherein: j is an integer between 0 and 3, inclusive; and k is an integer between 0 and 3, inclusive. In certain embodiments, the compound of Formula (I) is of formula:

wherein: j is an integer between 0 and 3, inclusive; and k is an integer between 0 and 3, inclusive.

In certain embodiments, the compound of Formula (I) is of formula:

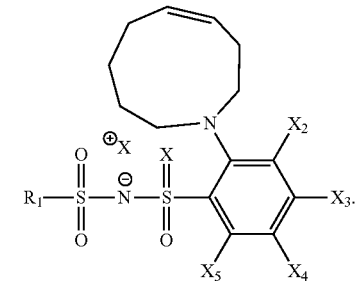

In certain embodiments, the compound of Formula (I) is of formula:

In certain embodiments, the compound of Formula (I) is of formula:

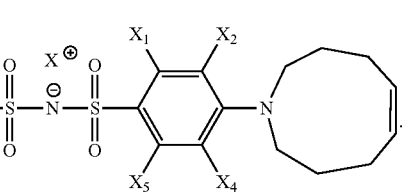

In certain embodiments, the compound of Formula (I) is of formula:

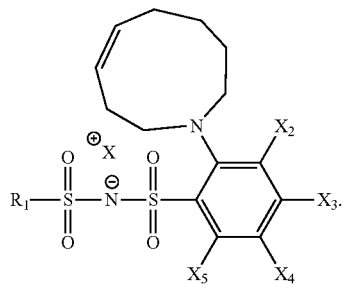

In certain embodiments, the compound of Formula (I) is of formula:

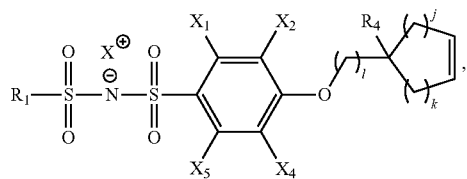

wherein: j is an integer between 0 and 3, inclusive; k is an integer between 0 and 3, inclusive; l is an integer between 0 and 10, inclusive; and $R_4$ is hydrogen or optionally substituted acyclic alkyl. In certain embodiments, the compound of Formula (I) is of formula:

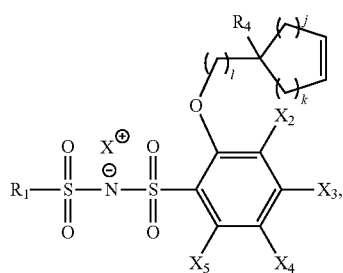

wherein: j is an integer between 0 and 3, inclusive; k is an integer between 0 and 3, inclusive; l is an integer between 0 and 10, inclusive; and $R_4$ is hydrogen or optionally substituted acyclic alkyl.

In certain embodiments, the compound of Formula (I) is of formula:

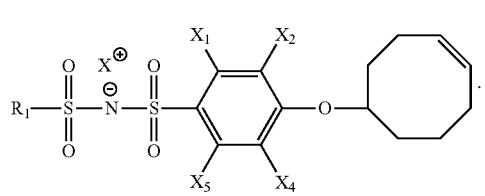

In certain embodiments, the compound of Formula (I) is of formula:

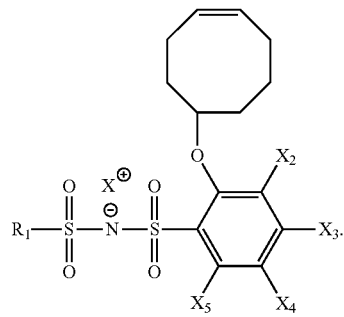

In certain embodiments, the compound of Formula (I) is of formula:

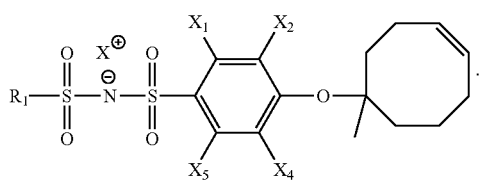

In certain embodiments, the compound of Formula (I) is of formula:

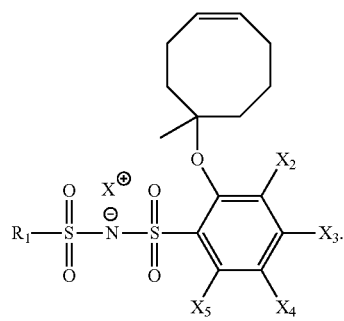

In certain embodiments, the compound of Formula (I) is of formula:

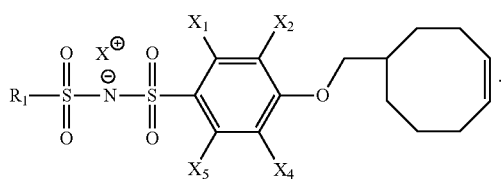

In certain embodiments, the compound of Formula (I) is of formula:

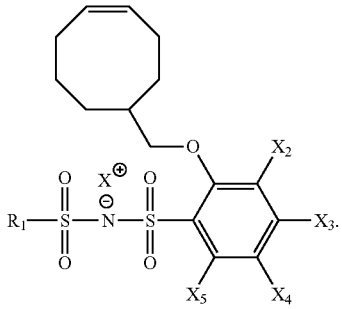

In certain embodiments, the compound of Formula (I) is of formula:

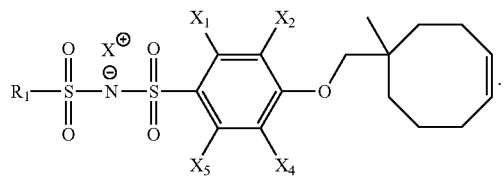

In certain embodiments, the compound of Formula (I) is of formula:

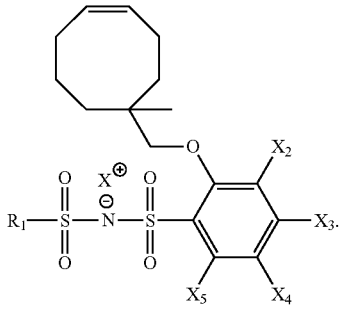

In certain embodiments, the compound of Formula (I) is of formula:

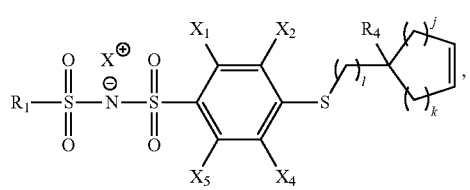

wherein: j is an integer between 0 and 3, inclusive; k is an integer between 0 and 3, inclusive; l is an integer between 0 and 10, inclusive; and $R_4$ is hydrogen or optionally substituted acyclic alkyl. In certain embodiments, the compound of Formula (I) is of formula:

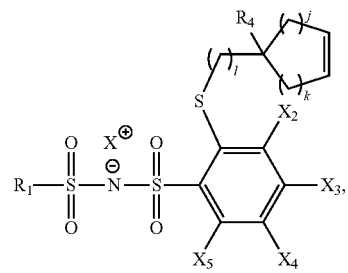

wherein: j is an integer between 0 and 3, inclusive; k is an integer between 0 and 3, inclusive; l is an integer between 0 and 10, inclusive; and $R_4$ is hydrogen or optionally substituted acyclic alkyl.

In certain embodiments, compound of Formula (I) is of formula:

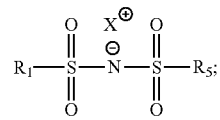

or a salt thereof, and $R_5$ is selected from the group consisting of:

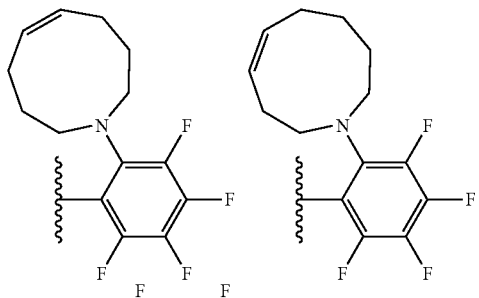

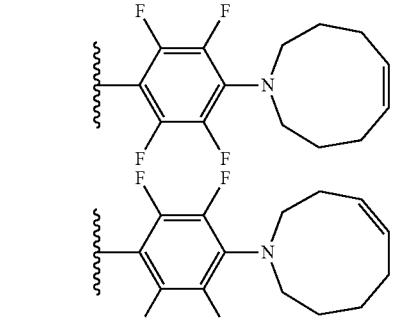

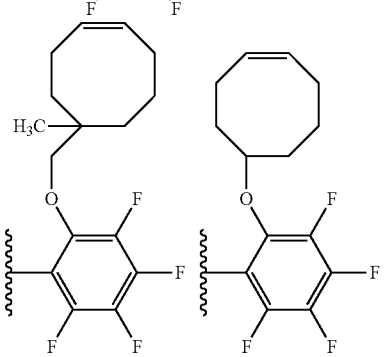

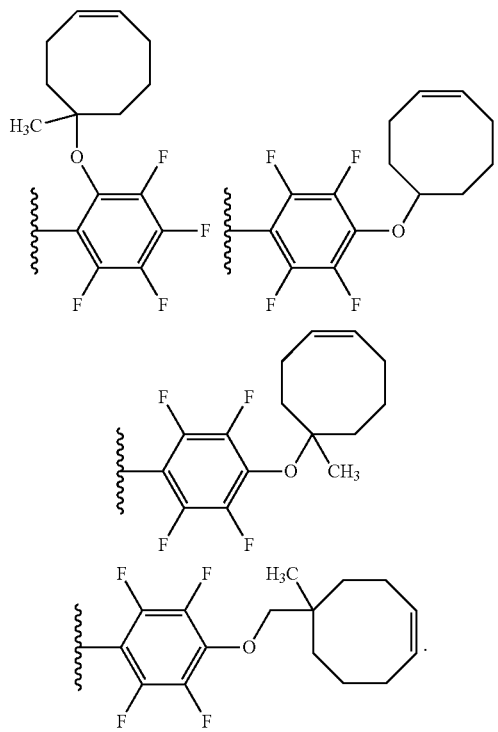
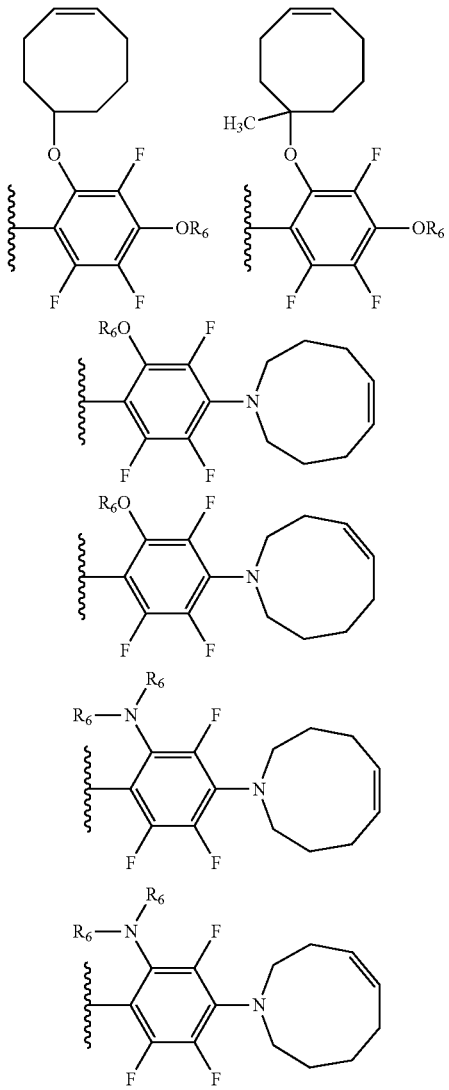
In certain embodiments, the compound of Formula (I) is of formula:
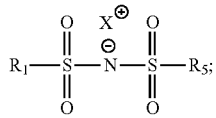
or a salt thereof, and $R_5$ is selected from the group consisting of:
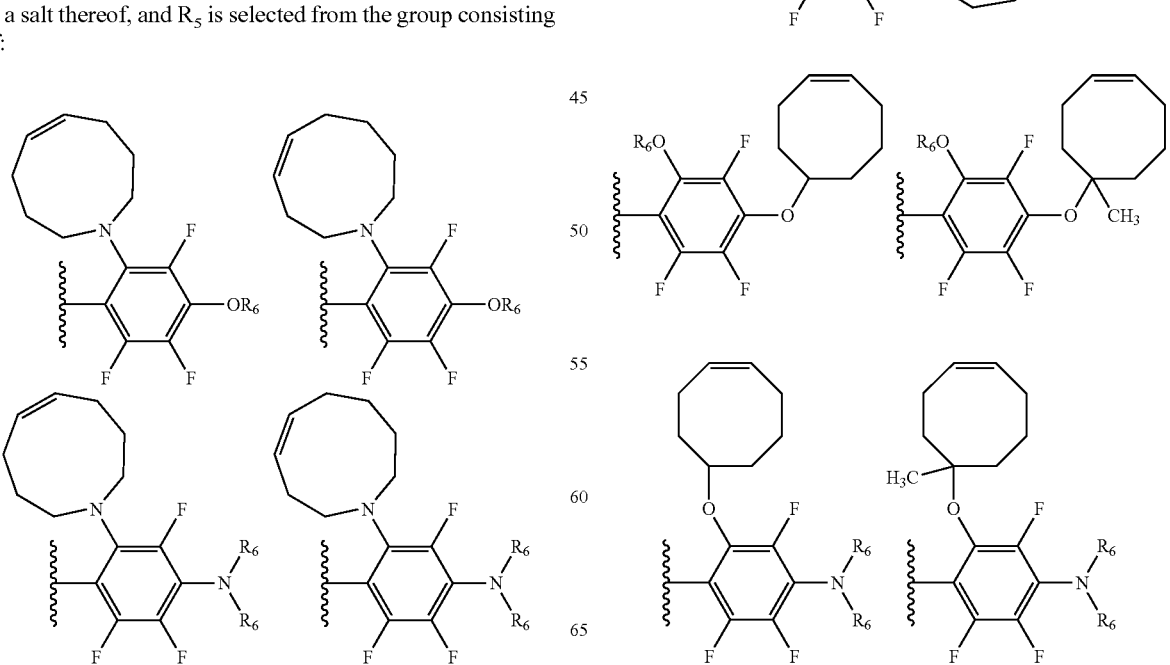

-continued

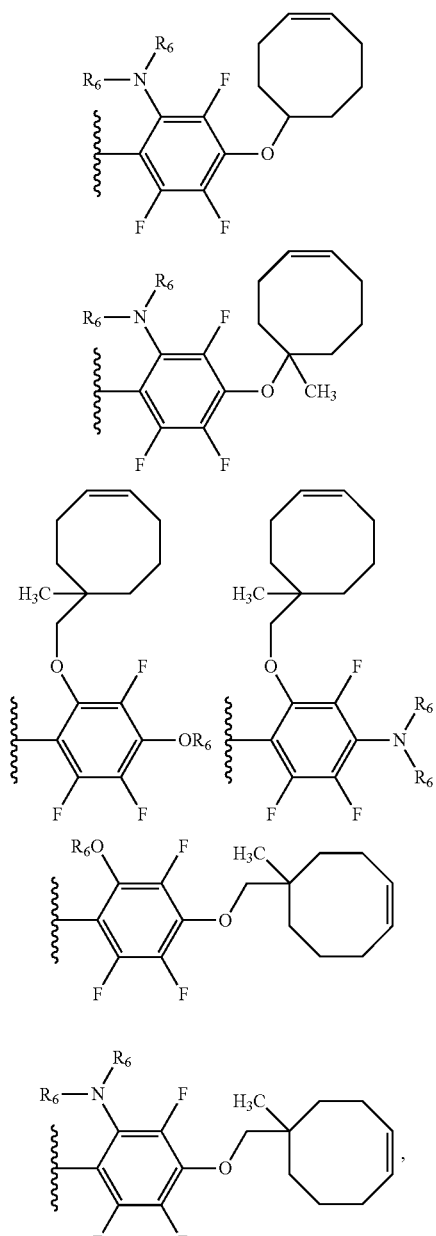

wherein: each $R_6$ independently is hydrogen; optionally substituted alkyl; optionally substituted heteroalkyl; optionally substituted aryl; optionally substituted heteroaryl; or two $R_6$ bonded to the same atom are taken together to form an optionally substituted heterocyclic moiety.

In certain embodiments, the compound of Formula (I) is of formula:

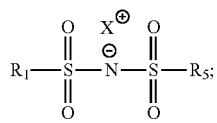

or a salt thereof, and $R_5$ is selected from the group consisting of:

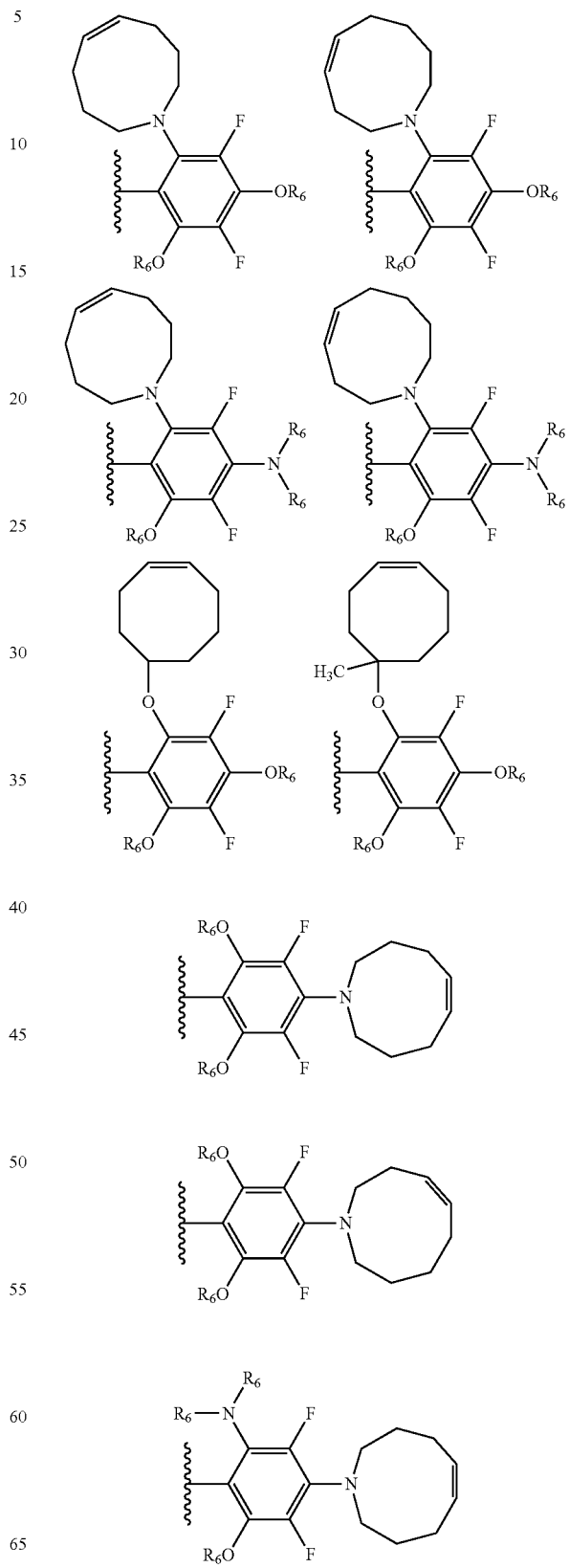

-continued
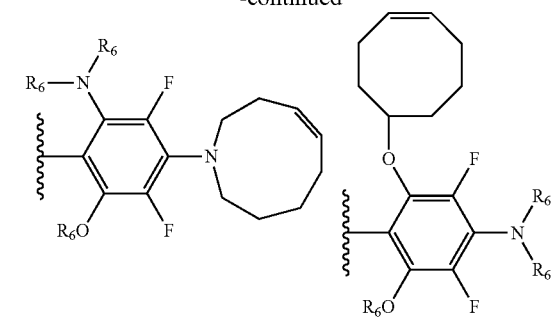
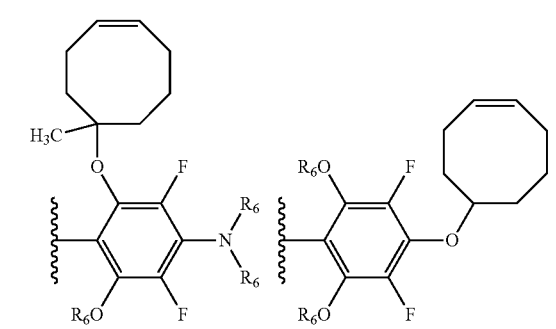
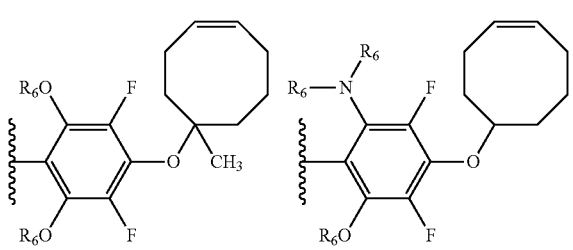
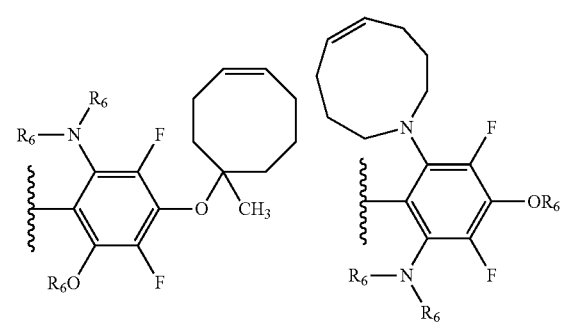
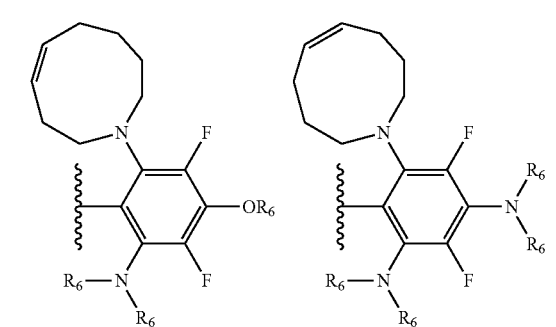
-continued
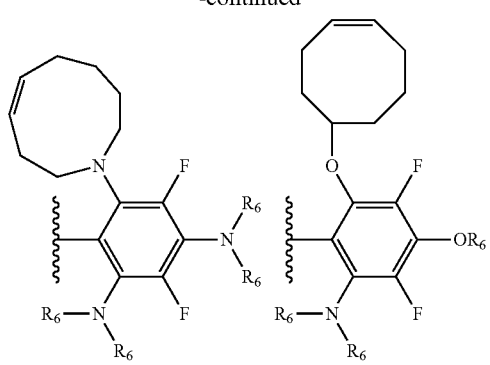
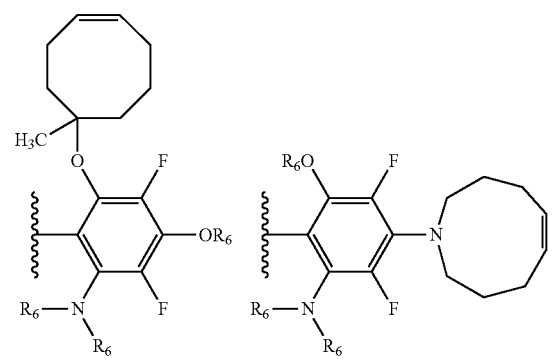
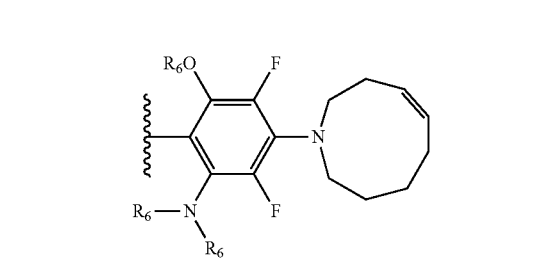
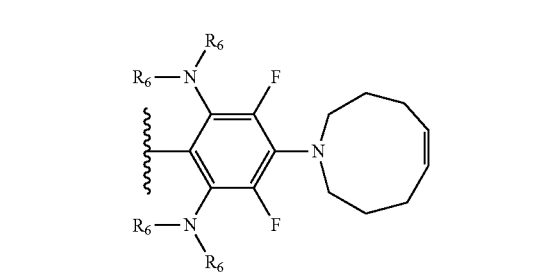
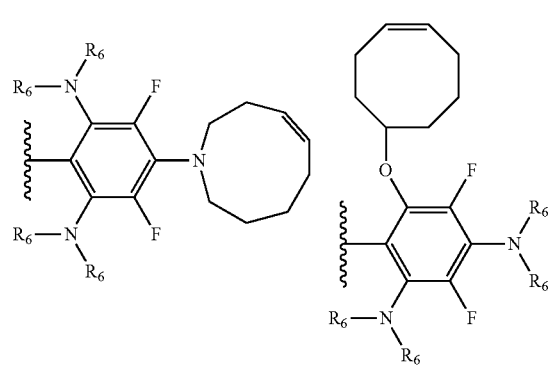

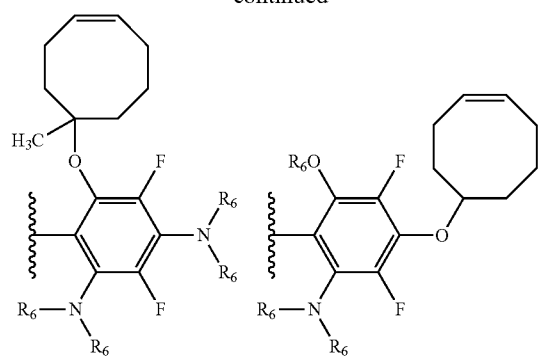
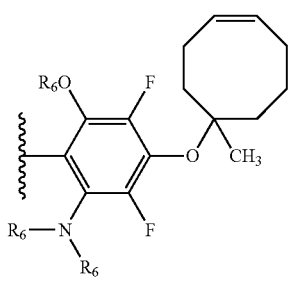
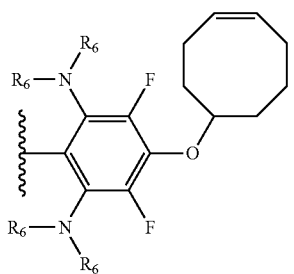
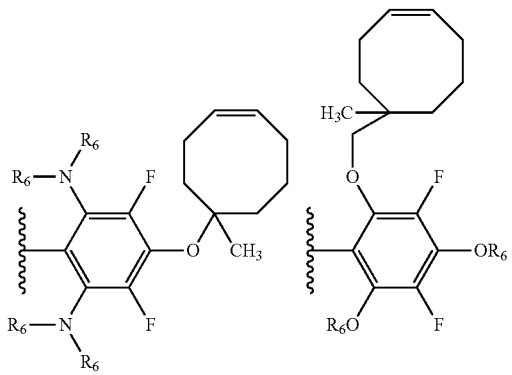
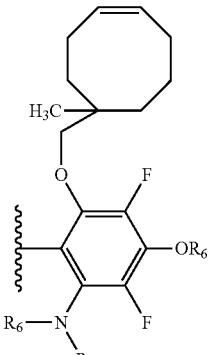
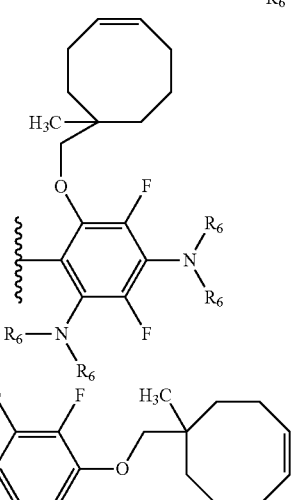
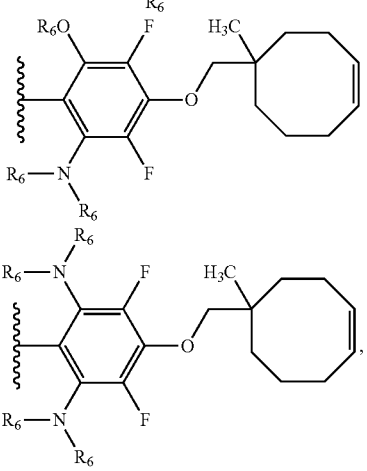
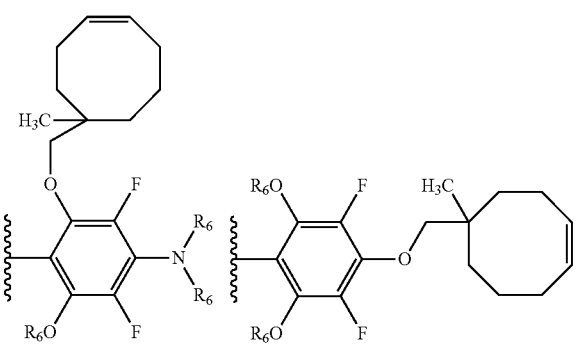

wherein: each $R_6$ independently is hydrogen; optionally substituted alkyl; optionally substituted heteroalkyl; optionally substituted aryl; optionally substituted heteroaryl; or two $R_6$ bonded to the same atom are taken together to form an optionally substituted cyclic heteroalkyl. In certain embodiments, each $R_6$ independently is selected from the group consisting of methyl, ethyl, n-propyl, iso-propyl, n-butyl, iso-butyl, tert-butyl, n-pentyl, neo-pentyl. In certain embodiments, $R_6$ is methoxyethyl. In certain embodiments, $R_6$ is phenyl. In certain embodiments, $R_6$ is methoxyphenyl. In certain embodiments, $R_6$ is pyridyl. In certain embodiments, two $R_6$ of

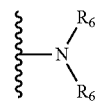

are taken together to form

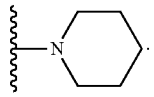

Polymers

Polymers in this disclosure are sulfonamide salt polymers or polymer electrolytes, which are prepared from the polymerization of compounds of Formula (I).

The present disclosure describes polymers of Formula (II) as described herein.

In one aspect, the polymer is a polymer of Formula (II):

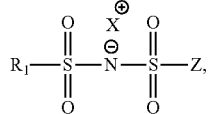

(II)

or a salt thereof, wherein

Z is:

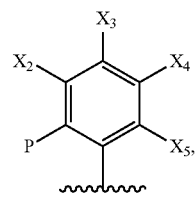

(II-a)

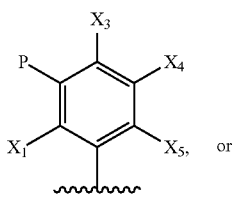

(II-b)

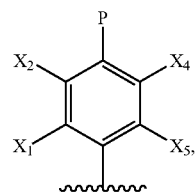

or (II-c)

wherein P is:

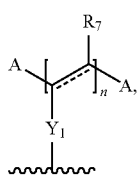

(II-d)

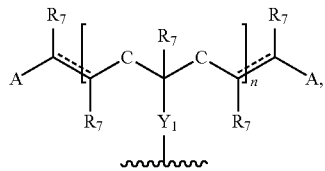

(II-e)

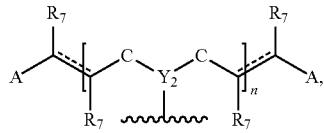

(II-f)

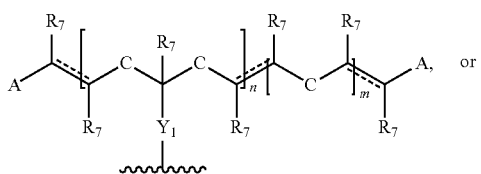

(II-g)

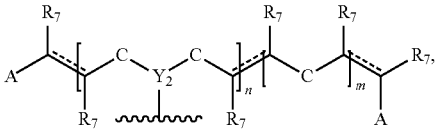

(II-h)

wherein:

═══ is a single bond or a double bond;

$R_1$ is optionally substituted haloalkyl; X is a metal or compound capable of forming a stable cation; $X_1$, $X_2$, $X_3$, $X_4$ and $X_5$ independently is halogen; optionally substituted, cyclic or acyclic haloalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted carbonyl; —$OR_2$; —$N(R_3)_2$; or —$SR_2$; each $R_2$ independently is hydrogen; optionally substituted, cyclic or acyclic haloalkyl; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; optionally substituted heteroaryl; an oxygen protecting group; or sulfur protecting group; each $R_3$ independently is hydrogen; optionally substituted, cyclic or acyclic haloalkyl; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; optionally substituted heteroaryl; a nitrogen protecting group; or two $R_3$ are taken together to form an optionally substituted cyclic alkenyl or an optionally substituted cyclic alkynyl; each $R_7$ independently is hydrogen; optionally substituted, cyclic or acyclic alkyl; optionally substituted, cyclic or acyclic heteroalkyl; optionally substituted aryl; or optionally substituted heteroaryl; $Y_1$ is O, S, $NR_4$, $C(R_4)_2$, $OC(R_4)_2$, or optionally substituted acyl, optionally substituted aryl, or optionally substituted heteroaryl; $Y_2$ is N, $CR_4$, optionally substituted aryl, or optionally substituted heteroaryl; A is optionally substituted, cyclic or acyclic haloalkyl; optionally substituted, cyclic or acyclic alkyl; optionally substituted, cyclic or acyclic heteroalkyl; optionally substituted aryl; optionally substituted heteroaryl, or optionally substituted acyl; B is a repeat unit; each C independently is optionally substituted, cyclic or acyclic alkyl; optionally substituted, cyclic or acyclic heteroalkyl; optionally substituted aryl; optionally substituted heteroaryl; optionally substituted acyl; or polymer; each n and m independently is an integer between 1 and 100, inclusive.

The descriptions for $R_1$, X, $X_1$, $X_2$, $X_3$, $X_4$, $X_5$, $R_2$, and $R_3$ have previously been provided. In certain embodiments, Z is

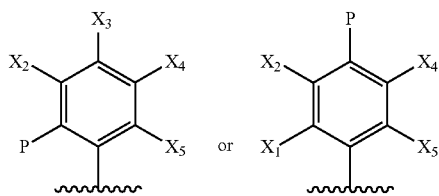

of a polymer of Formula (II); and P is selected from the group consisting of:

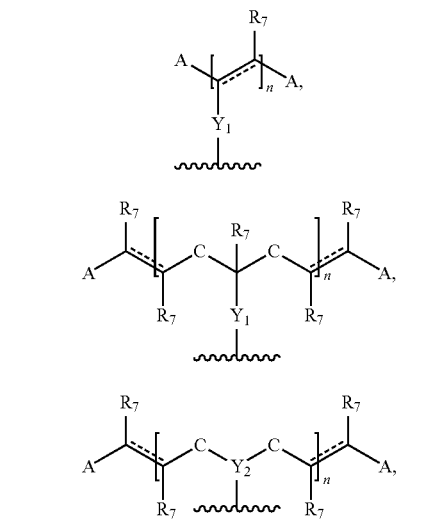

(II-d)

(II-e)

(II-f)

(II-g)

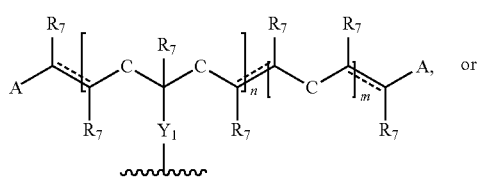

(II-h)

In certain embodiments, the structure of Formula (II-e) is

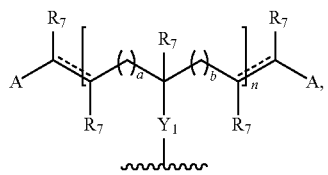

wherein: $Y_1$ is O or $OC(R_4)_2$; each $R_7$ independently is hydrogen or optionally substituted alkyl; a is an integer between 0 and 5, inclusive; b is an integer between 0 and 5, inclusive; n is an integer between 0 and 100, inclusive.

In certain embodiments, the structure of Formula (II-f) is

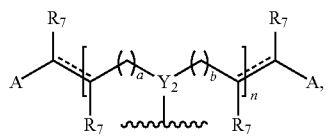

wherein: $Y_2$ is N; each $R_7$ independently is hydrogen or optionally substituted alkyl; a is an integer between 0 and 5, inclusive; b is an integer between 0 and 5, inclusive.

In certain embodiment, the structure of Formula (II-g) is

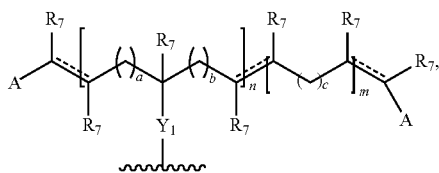

wherein: $Y_1$ is O or $OC(R_4)_2$; each $R_7$ independently is hydrogen or optionally substituted alkyl; a is an integer between 0 and 5, inclusive; b is an integer between 0 and 5, inclusive; c is an integer between 1 and 10, inclusive; n is an integer between 0 and 100, inclusive; and m is an integer between 0 and 100, inclusive.

In certain embodiments, the structure of Formula (II-h) is

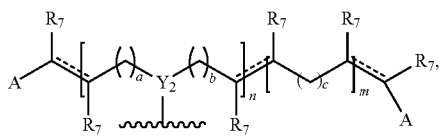

wherein: $Y_2$ is N; each $R_7$ independently is hydrogen or optionally substituted alkyl; a is an integer between 0 and 5, inclusive; b is an integer between 0 and 5, inclusive; c is an integer between 1 and 10, inclusive; n is an integer between 0 and 100, inclusive; and m is an integer between 0 and 100, inclusive.

In certain embodiments, the structure of Z is

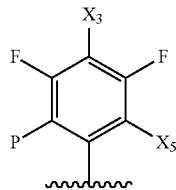

of a polymer of Formula (II), wherein: P is

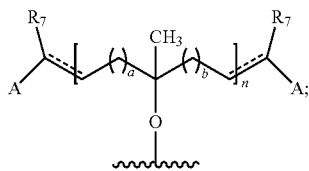

$X_3$ is fluorine; —$OR_6$; or —$N(R_6)_2$; $X_5$ is fluorine; —$OR_6$; or —$N(R_6)_2$; each $R_6$ independently is optionally substituted alkyl; optionally substituted heteroalkyl; optionally substituted aryl; optionally substituted heteroaryl; or two $R_6$ bonded to the same atom are taken together to form an optionally substituted cyclic heteroalkyl; a is 2; b is 3; n is an integer between 0 and 100, inclusive.

In certain embodiments, the structure of Z is

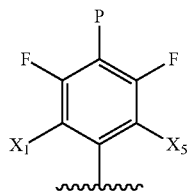

of a polymer of Formula (II), wherein: P is

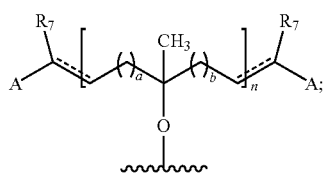

$X_1$ is fluorine; —$OR_6$; or —$N(R_6)_2$; $X_5$ is fluorine; —$OR_6$; or —$N(R_6)_2$; each $R_6$ independently is optionally substituted alkyl; optionally substituted heteroalkyl; or optionally substituted aryl; optionally substituted heteroaryl; or two $R_6$ bonded to the same atom are taken together to form an optionally substituted cyclic heteroalkyl; a is 2; b is 3; n is an integer between 0 and 100, inclusive.

In certain embodiments, the structure of Z is

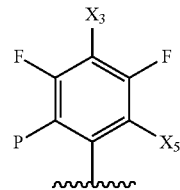

of a polymer of Formula (II), wherein: P is

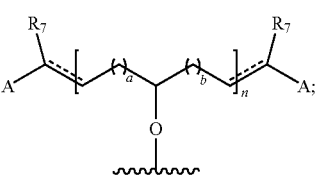

$X_3$ is fluorine; —$OR_6$; or —$N(R_6)_2$; $X_5$ is fluorine; —$OR_6$; or —$N(R_6)_2$; each $R_6$ independently is optionally substituted alkyl; optionally substituted heteroalkyl; optionally substituted aryl; optionally substituted heteroaryl; or two $R_6$ bonded to the same atom are taken together to form an optionally substituted cyclic heteroalkyl; a is 2; b is 3; n is an integer between 0 and 100, inclusive.

In certain embodiments, wherein the structure of Z is

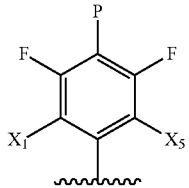

of a polymer of Formula (II), wherein: P is

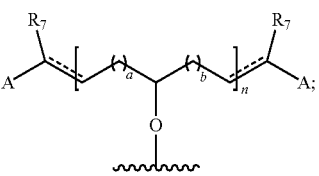

$X_1$ is fluorine; —$OR_6$; or —$N(R_6)_2$; $X_5$ is fluorine; —$OR_6$; or —$N(R_6)_2$; each $R_6$ independently is optionally substituted alkyl; optionally substituted heteroalkyl, or optionally substituted aryl; optionally substituted heteroaryl, or two $R_6$ bonded to the same atom are taken together to form an optionally substituted cyclic heteroalkyl; a is 2; b is 3; n is an integer between 0 and 100, inclusive.

In certain embodiments, the structure of Z is

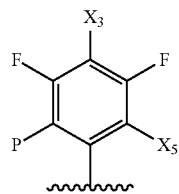

of a polymer of Formula (II), wherein: P is

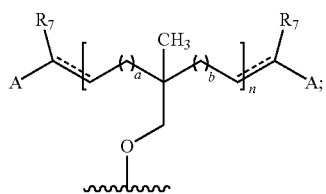

$X_3$ is fluorine; —$OR_6$; or —$N(R_6)_2$; $X_5$ is fluorine; —$OR_6$; or —$N(R_6)_2$; each $R_6$ independently is optionally substituted alkyl; optionally substituted heteroalkyl; optionally substituted aryl; optionally substituted heteroaryl; or two $R_6$ bonded to the same atom are taken together to form an optionally substituted cyclic heteroalkyl; a is 2; b is 3; n is an integer between 0 and 100, inclusive.

In certain embodiments, the structure of Z is

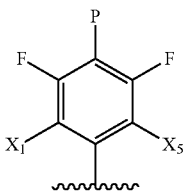

of a polymer of Formula (II), wherein: P is

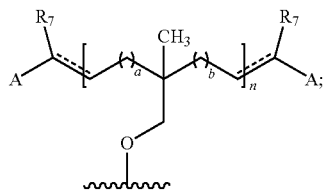

$X_1$ is fluorine; —$OR_6$; or —$N(R_6)_2$; $X_5$ is fluorine; —$OR_6$; or —$N(R_6)_2$; each $R_6$ independently is optionally substituted alkyl; optionally substituted heteroalkyl; optionally substituted aryl; optionally substituted heteroaryl; or two $R_6$ bonded to the same atom are taken together to form an optionally substituted cyclic heteroalkyl; a is 2; b is 3; n is an integer between 0 and 100, inclusive.

In certain embodiments, the structure of Z is

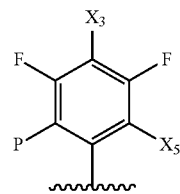

of a polymer of Formula (II), wherein: P is

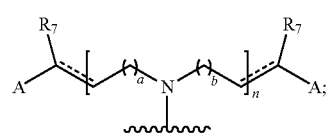

$X_3$ is fluorine; —$OR_6$; or —$N(R_6)_2$; $X_5$ is fluorine; —$OR_6$; or —$N(R_6)_2$; each $R_6$ independently is optionally substituted alkyl; optionally substituted heteroalkyl; optionally substituted aryl; optionally substituted heteroaryl; or two $R_6$ bonded to the same atom are taken together to form an optionally substituted cyclic heteroalkyl; a is 2; b is 4; n is an integer between 0 and 100, inclusive.

In certain embodiments, the structure of Z is

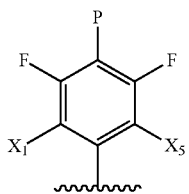

of a polymer of Formula (II), wherein: P is

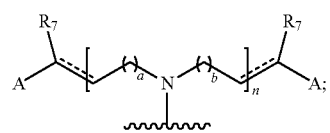

$X_1$ is fluorine; —$OR_6$; or —$N(R_6)_2$; $X_5$ is fluorine; —$OR_6$; or —$N(R_6)_2$; each $R_6$ independently is optionally substituted alkyl; optionally substituted heteroalkyl; optionally substituted aryl; optionally substituted heteroaryl; or two $R_6$ bonded to the same atom are taken together to form an optionally substituted cyclic heteroalkyl; a is 2; b is 4; n is an integer between 0 and 100, inclusive.

In certain embodiments, the structure of Z is

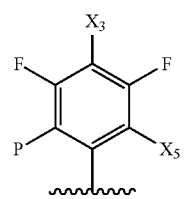

of a polymer of Formula (II), wherein: P is

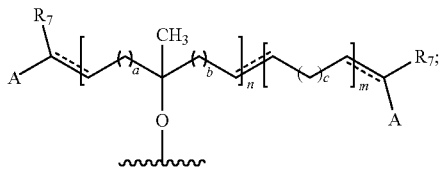

$X_3$ is fluorine; —$OR_6$; or —$N(R_6)_2$; $X_5$ is fluorine; —$OR_6$; or —$N(R_6)_2$; each $R_6$ independently is optionally substituted alkyl; optionally substituted heteroalkyl; optionally substituted aryl; optionally substituted heteroaryl; or two $R_6$ bonded to the same atom are taken together to form an optionally substituted cyclic heteroalkyl; a is 2; b is 3; c is 6; m is an integer between 0 and 100, inclusive; n is an integer between 0 and 100, inclusive.

In certain embodiments, the structure of Z is

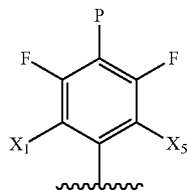

of a polymer of Formula (II), wherein: P is

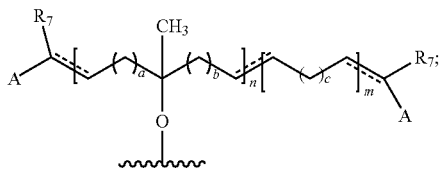

$X_1$ is fluorine; —$OR_6$; or —$N(R_6)_2$; $X_5$ is fluorine; —$OR_6$; or —$N(R_6)_2$; each $R_6$ independently is optionally substituted alkyl; optionally substituted heteroalkyl; optionally substituted aryl; optionally substituted heteroaryl; or two $R_6$ bonded to the same atom are taken together to form an optionally substituted cyclic heteroalkyl; a is 2; b is 3; c is 6; m is an integer between 0 and 100, inclusive; n is an integer between 0 and 100, inclusive.

In certain embodiments, the structure of Z is

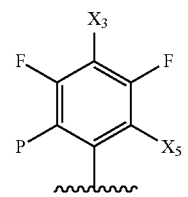

of a polymer of Formula (II), wherein: P is

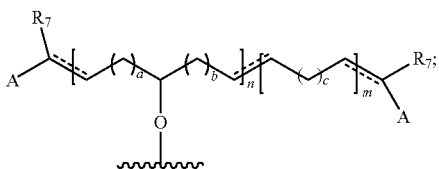

$X_3$ is fluorine; —$OR_6$; or —$N(R_6)_2$; $X_5$ is fluorine; —$OR_6$; or —$N(R_6)_2$; each $R_6$ independently is optionally substituted alkyl; optionally substituted heteroalkyl; optionally substituted aryl; optionally substituted heteroaryl; or two $R_6$ bonded to the same atom are taken together to form an optionally substituted cyclic heteroalkyl; a is 2; b is 3; c is 6; m is an integer between 0 and 100, inclusive; n is an integer between 0 and 100, inclusive.

In certain embodiments, the structure of Z is

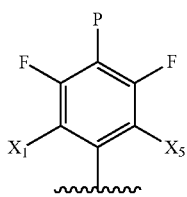

of a polymer of Formula (II), wherein: P is

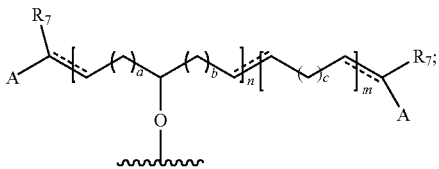

$X_1$ is fluorine; —$OR_6$; or —$N(R_6)_2$; $X_5$ is fluorine; —$OR_6$; or —$N(R_6)_2$; each $R_6$ independently is optionally substituted alkyl; optionally substituted heteroalkyl; optionally substituted aryl; optionally substituted heteroaryl; or two $R_6$ bonded to the same atom are taken together to form an optionally substituted cyclic heteroalkyl; a is 2; b is 3; c is 6; m is an integer between 0 and 100, inclusive; n is an integer between 0 and 100, inclusive In certain embodiments, the structure of Z is

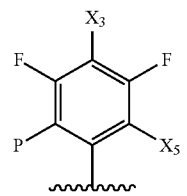

of a polymer of Formula (II), wherein: P is

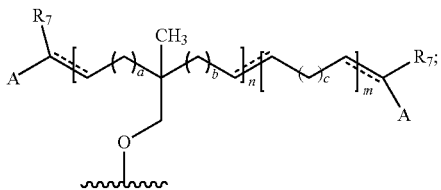

$X_3$ is fluorine; —$OR_6$; or —$N(R_6)_2$; $X_5$ is fluorine; —$OR_6$; or —$N(R_6)_2$; each $R_6$ independently is optionally substituted alkyl; optionally substituted heteroalkyl; optionally substituted aryl; optionally substituted heteroaryl; or two $R_6$ bonded to the same atom are taken together to form an optionally substituted cyclic heteroalkyl; a is 2; b is 3; c is 6; m is an integer between 0 and 100, inclusive; n is an integer between 0 and 100, inclusive.

In certain embodiments, the structure of Z is

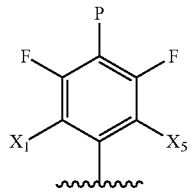

of a polymer of Formula (II), wherein: P is

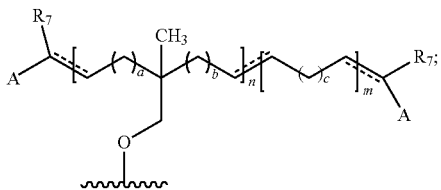

$X_1$ is fluorine; —$OR_6$; or —$N(R_6)_2$; $X_5$ is fluorine; —$OR_6$; or —$N(R_6)_2$; each $R_6$ independently is optionally substituted alkyl; optionally substituted heteroalkyl; optionally substituted aryl; optionally substituted heteroaryl; or two $R_6$ bonded to the same atom are taken together to form an optionally substituted cyclic heteroalkyl; a is 2; b is 3; c is 6; m is an integer between 0 and 100, inclusive; n is an integer between 0 and 100, inclusive.

In certain embodiments, the structure of Z is

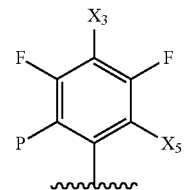

of a polymer of Formula (II), wherein: P is

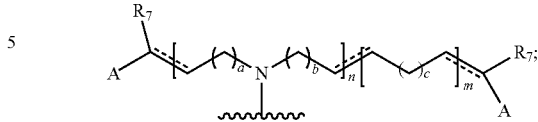

$X_3$ is fluorine; —$OR_6$; or —$N(R_6)_2$; $X_5$ is fluorine; —$OR_6$; or —$N(R_6)_2$; each $R_6$ independently is optionally substituted alkyl; optionally substituted heteroalkyl; optionally substituted aryl; optionally substituted heteroaryl; or two $R_6$ bonded to the same atom are taken together to form an optionally substituted cyclic heteroalkyl; a is 2; b is 4; c is an integer between 5 and 10, inclusive; m is an integer between 0 and 100, inclusive; n is an integer between 0 and 100, inclusive.

In certain embodiments, the structure of Z is

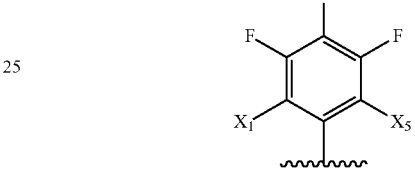

of a polymer of Formula (II), wherein: P is

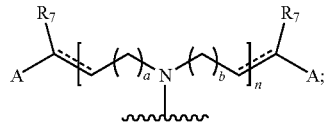

$X_1$ is fluorine; —$OR_6$; or —$N(R_6)_2$; $X_5$ is fluorine; —$OR_6$; or —$N(R_6)_2$; each $R_6$ independently is optionally substituted alkyl; optionally substituted heteroalkyl; optionally substituted aryl; optionally substituted heteroaryl; or two $R_6$ bonded to the same atom are taken together to form an optionally substituted cyclic heteroalkyl; a is 2; b is 4; c is an integer between 5 and 10, inclusive; m is an integer between 0 and 100, inclusive; n is an integer between 0 and 100, inclusive.

Exemplary polymers may be described by a number of properties, including, $M_n$=average molecular weight (kDa), $D_H$=average hydrodynamic diameter (nm), and PDI=polydispersity.

In certain embodiments, the $M_n$ is determined with gel permeation chromatography, viscometry via the (Mark-Houwink equation), colligative methods (such as vapor pressure osmometry), end-group determination, or proton NMR. In certain embodiments, the $M_w$ is determined with static light scattering, small angle neutron scattering, X-ray scattering, and sedimentation velocity. In some embodiments, the average molecular weight of the polymer is between about 1 kDa and about 100 kDa, e.g., between about 1 kDa and about 50 kDa, about 15 kDa and about 85 kDa, about 20 kDa and about 60 kDa, or about 30 kDa and about 50 kDa. In one embodiment, the average molecular weight of the polymer is between about 20 kDa and about 60 kDa. In one embodiment, the average molecular weight of the polymer is between about 30 kDa and about 50 kDa.

In some embodiments, the average molecular weight of the polymer is less than about 50 kDa (e.g., less than about 45 kDa, less than about 40 kDa, less than about 35 kDa, less than about 30 kDa, less than about 25 kDa, less than about 20 kDa, less than about 15 kDa, less than about 10 kDa, less than about 5 kDa, or less than about 1 kDa).

In some embodiments, the average molecular weight of the polymer is less than about 100 kDa (e.g., less than about 95 kDa, less than about 90 kDa, less than about 85 kDa, less than about 80 kDa, less than about 75 kDa, less than about 70 kDa, less than about 65 kDa, less than about 60 kDa, less than about 55 kDa, or less than about 50 kDa), e.g., as determined by gel permeation chromatography.

In certain embodiments, n is an integer between 2 and 70, between 2 and 50, between 2 and 30, between 2 and 10, between 10 and 100, between 10 and 70, between 10 and 50, between 10 and 30, between 30 and 100, between 30 and 50, between 50 and 100, inclusive.

In certain embodiments, m is an integer between 2 and 70, between 2 and 50, between 2 and 30, between 2 and 10, between 10 and 100, between 10 and 70, between 10 and 50, between 10 and 30, between 30 and 100, between 30 and 50, between 50 and 100, inclusive.

In some embodiments, the polydispersity of the polymer is between 0 and 1, inclusive. In some embodiments, the average polydispersity of the polymer is less than about 0.5 (e.g., less than about 0.4, about 0.35, about 0.3, about 0.25, about 0.2, about 0.15, or less). In some embodiments, the average polydispersity of the polymer is less than about 0.3. In some embodiments, the average polydispersity of the polymer is less than about 0.2. In some embodiments, the polymer is monodisperse. In some embodiments, the polymer is about 50% monodisperse (e.g., about 55%, about 60%, about 65%, about 70%, about 75%, about 80%, about 85%, about 90%, about 95%, about 99%, or about 99.9% monodisperse).

Methods of Preparation of Compounds and Polymers

The present disclosure describes methods of preparing compounds of Formula (I) and polymers of Formula (II) as described herein.

In one aspect, a method of preparing a compound of Formula (I) is described, which comprises reacting a compound of Formula (I-b):

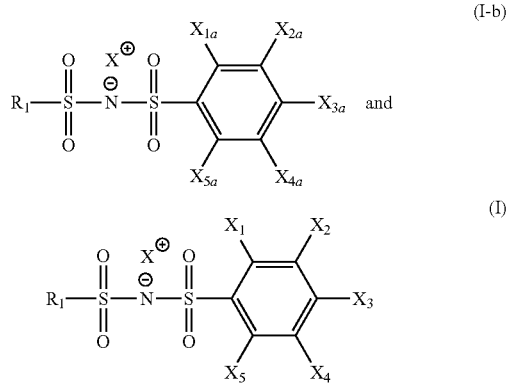

with one or more nucleophiles selected from $HOR_2$, $HN(R_3)_2$, $HSR_2$, and $HC(R_3)_3$ to obtain a compound of Formula (I); wherein: $X_{1a}$, $X_{2a}$, $X_{3a}$, $X_{4a}$, and $X_{5a}$ independently is halogen or optionally substituted haloalkyl; each $R_2$ independently is hydrogen; optionally substituted, cyclic or acyclic haloalkyl; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; optionally substituted heteroaryl; an oxygen protecting group; or sulfur protecting group; each $R_3$ independently is hydrogen; optionally substituted, cyclic or acyclic haloalkyl; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; optionally substituted heteroaryl; a nitrogen protecting group; or two $R_3$ are taken together to form an optionally substituted cyclic alkyl, or optionally substituted cyclic alkenyl, or an optionally substituted cyclic alkynyl; provided that at least one of $X_1$, $X_2$, $X_3$, $X_4$, and $X_5$ is optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; and at least one of $X_1$, $X_2$, $X_3$, $X_4$, and $X_5$ is halogen; optionally substituted cyclic or acyclic haloalkyl.

In certain embodiments, $HOR_2$ is selected from the group consisting of methanol, ethanol, n-propanol, iso-propanol, n-butanol, iso-butanol, tert-butanol, n-pentanol, neo-pentanol, methoxyethanol, phenol, methoxyphenol,

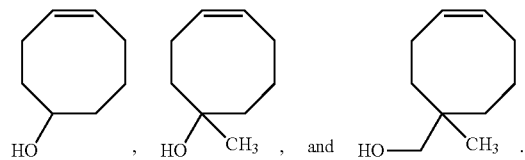

In certain embodiments, $HN(R_3)_2$ is selected from the group consisting of piperdine, 2-aminopyridine, 4-aminopyridine, aniline, methanamine, ethanamine, n-propamine, iso-propanamine, n-butanamine, iso-butanamine, tert-butanamine, n-pentanamine, neo-pentanamine, methoxyethanamine, methoxyaniline,

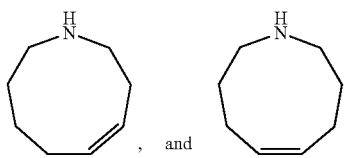

The nucleophile undergoes a nucleophilic aromatic substitution reaction with a compound of Formula (I-b). In certain embodiments, the compound of Formula (I-b) undergoes nucleophilic aromatic substitution with one nucleophile. In certain embodiments, the compound of Formula (I-b) undergoes nucleophilic aromatic substitution with two nucleophiles. In certain embodiments, the compound of Formula (I-b) undergoes nucleophilic aromatic substitution with three nucleophiles. In certain embodiments, the compound of Formula (I-b) undergoes nucleophilic aromatic substitution with four or more nucleophiles. The nucleophiles used in the nucleophilic aromatic substitution reactions can be the same, different, or any combination thereof.

In certain embodiments, a method of preparing a polymer of Formula (II) is described, which comprises polymerizing a compound of Formula (I) to produce a polymer of a compound of Formula (II). The step of polymerizing is not limited by those mentioned in this disclosure. The step of polymerizing is a polymerization selected from the group consisting of metathesis polymerization, living radical polymerization, reversible-deactivation radical polymerization, atom transfer radical polymerization (ATRP), nitroxide mediated radical polymerization (NMP), and reversible addition-fragmentation chain transfer (RAFT) polymerization.

In certain embodiments, the methods for preparing the polymers described herein may involve a metathesis reaction. In certain embodiments, the metathesis reaction is a ring-opening metathesis polymerization (ROMP) (Liu et al. *J. Am. Chem. Soc.* 2012, 134, 16337; Liu, J.; Gao, A. X.; Johnson, J. A. *J Vis Exp* 2013, e50874; each of which is incorporated herein by reference). In certain embodiments, the polymers described herein are prepared by polymerization of one or more monomers of Formula (I) in the presence of a metathesis catalyst. The preparation methods described herein are versatile and have little limitations.

In certain embodiments, the metathesis catalyst (e.g., ROMP catalyst) is a tungsten (W), molybdenum (Mo), or ruthenium (Ru) catalyst. In certain embodiments, the ROMP catalyst is a ruthenuim catalyst. ROMP catalysts useful in the synthetic methods described herein include catalysts as depicted below, and as described in Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-2580; Furstner et al., *J. Am. Chem. Soc.* (1999) 121:9453; and *Chem. Eur. J.* (2001) 7:5299; the entire contents of each of which are incorporated herein by reference.

In certain embodiments, the ROMP catalyst is a Grubbs catalyst. In certain embodiments, the Grubbs catalyst is selected from the group consisting of:

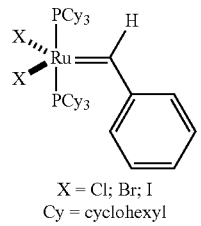

X = Cl; Br; I
Cy = cyclohexyl

Benzylidenebis-(tricyclohexylphosphine)-dichlororuthenium (X=Cl); Benzylidenebis-(tricyclohexylphosphine)-dibromoruthenium (X=Br); Benzylidenebis-(tricyclohexylphosphine)-diiodoruthenium (X=I);

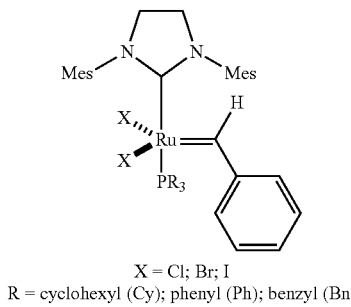

X = Cl; Br; I
R = cyclohexyl (Cy); phenyl (Ph); benzyl (Bn)

1,3-(Bis(mesityl)-2-imidazolidinylidene)dichloro-(phenylmethylene) (tricyclohexyl-phosphine)ruthenium (X=Cl; R=cyclohexyl); 1,3-(Bis(mesityl)-2-imidazolidinylidene)dibromo-(phenylmethylene) (tricyclohexyl-phosphine)ruthenium (X=Br; R=cyclohexyl); 1,3-(Bis(mesityl)-2-imidazolidinylidene)diiodo-(phenylmethylene) (tricyclohexyl-phosphine)ruthenium (X=I; R=cyclohexyl); 1,3-(Bis(mesityl)-2-imidazolidinylidene)dichloro-(phenylmethylene) (triphenylphosphine)ruthenium (X=Cl; R=phenyl); 1,3-(Bis(mesityl)-2-imidazolidinylidene)dichloro-(phenylmethylene) (tribenzylphosphine)ruthenium (X=Cl; R=benzyl);

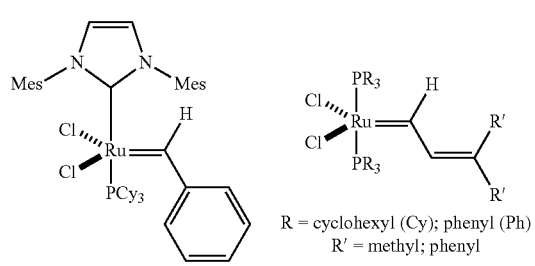

R = cyclohexyl (Cy); phenyl (Ph)
R' = methyl; phenyl

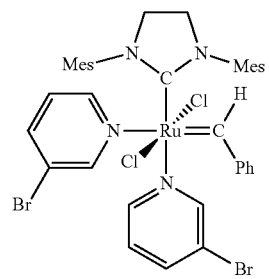

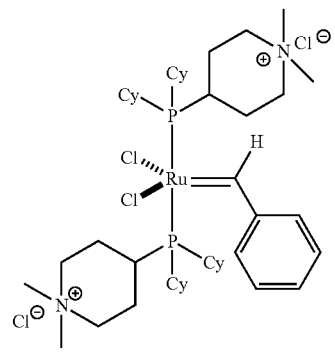

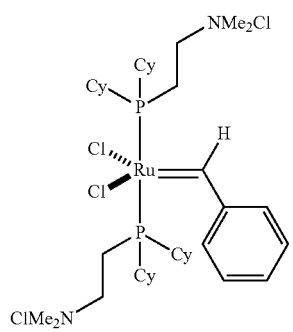

-continued

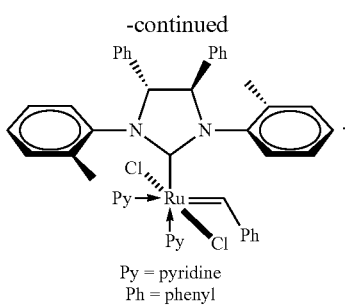

Py = pyridine
Ph = phenyl

In certain embodiments, the ROMP catalyst is a Grubbs-Hoveyda catalyst. In certain embodiments, the Grubbs-Hoveyda catalyst is selected from the group consisting of:

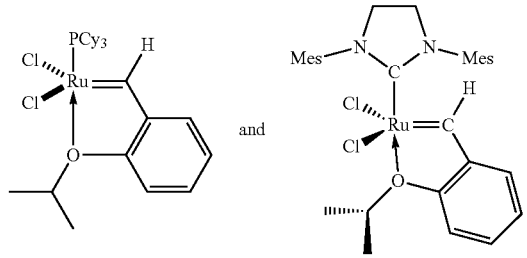

and

In certain embodiments, the ROMP catalyst is selected from the group consisting of:

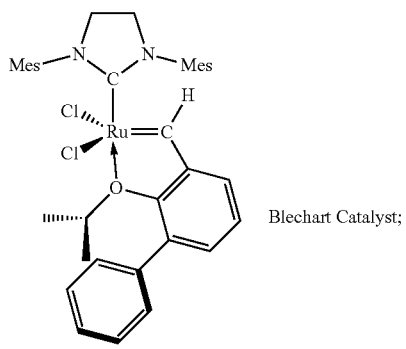

Blechart Catalyst;

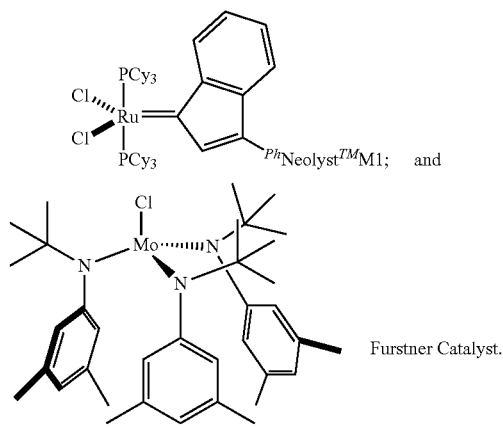

$^{Ph}$Neolyst$^{TM}$M1; and

Furstner Catalyst.

In certain embodiments, the ROMP catalyst is of the formula:

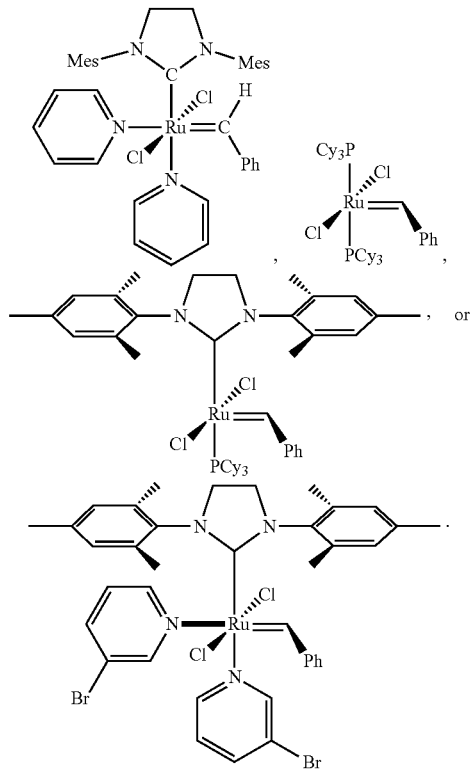

The ROMP can be conducted in one or more aprotic solvents. The term "aprotic solvent" means a non-nucleophilic solvent having a boiling point range above ambient temperature, preferably from about 25° C. to about 190° C. at atmospheric pressure. In certain embodiments, the aprotic solvent has a boiling point from about 80° C. to about 160° C. at atmospheric pressure. In certain embodiments, the aprotic solvent has a boiling point from about 80° C. to about 150° C. at atmospheric pressure. Examples of such solvents are methylene chloride, acetonitrile, toluene, DMF, diglyme, THF, and DMSO.

The ROMP can be quenched with a vinyl ether of the formula

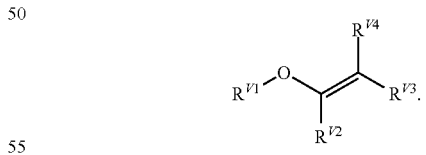

Each of $R^{V1}$, $R^{V2}$, $R^{V3}$, and $R^{V4}$ is independently optionally substituted alkyl, optionally substituted alkenyl, optionally substituted alkynyl, optionally substituted carbocyclyl, optionally substituted phenyl, optionally substituted heterocyclyl, or optionally substituted heteroaryl. In certain embodiments, $R^{V1}$ is optionally substituted alkyl, and $R^{V2}$, $R^{V3}$, and $R^{V4}$ are hydrogen. In certain embodiments, $R^{V1}$ is unsubstituted alkyl, and $R^{V2}$, $R^{V3}$, and $R^{V4}$ are hydrogen. In certain embodiments, $R^{V1}$ is substituted alkyl, and $R^{V2}$, $R^{V3}$, and $R^{V4}$ are hydrogen. In certain embodiments, $R^{V1}$ is methyl, and $R^{V2}$, $R^{V3}$, and $R^{V4}$ are hydrogen. In certain embodiments, $R^{V1}$ is ethyl, and $R^{V2}$, $R^{V3}$, and $R^{V4}$ are hydrogen. In certain embodiments, $R^{V1}$ is propyl, and $R^{V2}$, $R^{V3}$ and $R^{V4}$ are hydrogen. In certain embodiments, $R^{V1}$ is optionally substituted alkenyl, and $R^{V2}$, $R^{V3}$, and $R^{V4}$ are hydrogen. In certain embodiments, $R^{V1}$ is unsubstituted alkenyl, and $R^{V2}$, $R^{V3}$ and $R^{V4}$ are hydrogen. In certain embodiments, $R^{V1}$ is vinyl, and $R^{V2}$, $R^{V3}$, and $R^{V4}$ are hydrogen. In certain embodiments, the ROMP is quenched by ethyl vinyl ether.

In certain embodiments, the methods for preparing the polymers described herein may involve a polymerization reaction selected from the group consisting of: living radical polymerization, reversible-deactivation radical polymerization, atom transfer radical polymerization (ATRP), nitroxide mediated radical polymerization (NMP), and reversible addition-fragmentation chain transfer (RAFT) polymerization. In certain embodiments, the polymerization uses an iniferter, initiator, or chain transfer agent as described herein.

The step of polymerizing can optionally be followed by a step of hydrogenating the polymer of Formula (II). In certain embodiments, the step of hydrogenating utilizes a hydrogen source selected from the group consisting of hydrogen gas, hydrazine, hydrazide, formic acid, isopropanol, and dihydroanthracene.

A purification step can be performed after the step of hydrogenating. In certain embodiments, the purification step is dialysis purification. Dialysis is a simple process in which small solutes diffuse from a high concentration solution to a low concentration solution across a semipermeable membrane until equilibrium is reached. Since the porous membrane selectively allows smaller solutes to pass while retaining larger species, dialysis can be controlled or manipulated to produce desired results for a variety of dialysis applications.

The cation of a polymer of Formula (II) can also undergo an ion exchange reaction. In certain embodiments, a method of preparing a lithium salt of a polymer of Formula (II) from the sodium salt of a polymer of Formula (II), comprises an ion exchange reaction of the sodium salt of a polymer of Formula (II) with a inorganic lithium salt. Any inorganic lithium salt may be used for the ion exchange reaction. In certain embodiments, the inorganic lithium salt is LiCl.

Compositions

The present disclosure provides compositions comprising a polymer described herein to form a polymer electrolyte or polyelectrolyte. In certain embodiments, the polymer electrolyte is a component of an energy storage device. In certain embodiments, the polymer electrolyte is a component of a conductive material. In certain embodiments, the polymer electrolyte is a component of an electrochemical cell. In certain embodiments, the polymer electrolyte is a component of a gel. In certain embodiments, the polymer electrolyte is a component of an adhesive. In certain embodiments, the polymer electrolyte is a component of a coating. In certain embodiments, the polymer electrolyte is a component of a drug delivery vehicle.

Compositions consisting of polymer electrolytes described herein can be prepared by any method known in the art.

In certain embodiments, a polymer electrolyte composition is a component of an energy storage device. Electrolytic devices, fuel cells, metal-ion batteries (e.g., lithium-ion batteries) and metal-air batteries (e.g., lithium-air batteries) are non-limiting examples of energy storage devices. Energy can be supplied to electrolytic devices by photovoltaic cells, wind power generators, or other energy sources.

An energy storage device may be combined with additional energy storage device to form a larger device or system. This may take the form of a stack of devices or subsystems (e.g., fuel cell and/or electrolytic device and/or metal-air battery) to form a larger device or system.

Various components of a device, such as the electrodes, power source, electrolyte, separator, container, circuitry, insulating material, gate electrode, etc. can be fabricated by those of ordinary skill in the art from any of a variety of components, as well as those described in any of those patent applications described herein. Components may be molded, machined, extruded, pressed, isopressed, infiltrated, coated, in green or fired states, or formed by any other suitable technique. Those of ordinary skill in the art are readily aware of techniques for forming components of devices herein.

Generally speaking, an energy storage device includes two electrodes (i.e., an anode and a cathode) in contact with an electrolyte. The electrodes are electrically connected to one another; the electrical connection can, depending on the intended use of the system, include a power source (when the desired electrochemical reactions require electrical energy) or an electrical load (when the desired electrochemical reactions produce electrical energy). An energy storage device can be used for producing, storing, or converting chemical and/or electrical energy.

Where a system is described as involving a first electrode and/or a second electrode (one or both of which can include a catalytic material), with production of oxygen gas via water electrolysis at the first electrode and/or production of hydrogen gas at the second electrode, it is to be understood that the first electrode can facilitate oxidation of water or another species to produce oxygen gas or another oxidized product. Examples of reactants that can be oxidized in this context can include methanol, formic acid, ammonia, etc. Examples of oxidized products can include $CO_2$, $N_2$, etc. At the second electrode, a reaction can be facilitated in which water (or hydrogen ions) is reduced to make hydrogen gas, but it is to be understood that a variety of reactants not limited to water (e.g., metal oxides or ions, acetic acid, phosphoric acid, etc.) can be reduced to form hydrogen gas and/or metals and/or other products of the reduction reaction (e.g., metal hydroxides, acetate, phosphate, etc.). This reaction at the second electrode can be run in reverse, in "fuel cell" operation, such that hydrogen gas (and/or other exemplary products noted above) is oxidized to form water (and/or other exemplary reactants noted above). In some cases, the compositions, electrodes, methods, and/or systems may be used for reducing hydrogen gas. In some cases, the compositions, electrodes, methods, and/or systems may be used in connection with a photoelectrochemical cell.

In certain embodiments, a polymer electrolyte composition is a component of an electrochemical cell. An electrochemical cell includes an electrolyte in addition to the electrodes and other components present within the cell. The electrolytes used in electrochemical cells can function as a medium for the storage and transport of ions, and in the special case of solid electrolytes and gel electrolytes, these materials may additionally function as a separator between the anode and the cathode. Any suitable liquid, solid, or gel material capable of storing and transporting ions between the anode and the cathode may be used. The electrolyte may be electronically non-conductive to prevent short circuiting between the anode and the cathode. In one set of embodiments a non-aqueous-based electrolyte is used; in another set of embodiments, an aqueous-based electrolyte is used.

In some embodiments, an electrolyte may be present as a polymer layer such as a gel or solid polymer layer. In some cases, in addition to being able to function as a medium for the storage and transport of ions, a polymer layer positioned between an anode and cathode can function to screen the anode (e.g., a base electrode layer of the anode) from any cathode roughness under an applied force or pressure, keeping the anode surface smooth under force or pressure, and stabilizing any multi-layered structures of the anode (e.g., ceramic polymer multi-layer) by keeping the multi-layer pressed between the base electrode layer and the smooth polymer layer. In some such embodiments, the polymer layer may be chosen to be compliant and have a smooth surface.

The electrolyte can comprise one or more ionic electrolyte salts to provide ionic conductivity and one or more liquid electrolyte solvents, gel polymer materials, or polymer materials. Suitable non-aqueous electrolytes may include organic electrolytes comprising one or more materials selected from the group consisting of liquid electrolytes, gel polymer electrolytes, and solid polymer electrolytes. Examples of non-aqueous electrolytes for lithium batteries are described by Dorniney in *Lithium Batteries, New Materials, Developments and Perspectives*, Chapter 4, pp. 137-165, Elsevier, Amsterdam (1994). Examples of gel polymer electrolytes and solid polymer electrolytes are described by Alamgir et al. in *Lithium Batteries, New Materials, Developments and Perspectives*, Chapter 3, pp. 93-136, Elsevier, Amsterdam (1994).

In certain embodiments, a polymer electrolyte composition is a component of an drug delivery vehicle. In certain embodiments, the drug delivery vehicle further comprises an agent. In certain embodiments, the drug delivery vehicle further comprises a carrier. In certain embodiments, the drug delivery vehicle further comprises an excipient.

In general, such preparatory methods include bringing the polymer described herein into association with one or more carriers or excipients, and may include one or more agents or accessory ingredients, and then, if necessary and/or desirable, shaping, and/or packaging the product into a desired single- or multi-dose unit. In certain embodiments, the agent and the polymer of the composition are not covalently attached.

Relative amounts of the polymer, excipient, agent, and/or any additional ingredients in a composition described herein will vary, depending upon the identity, size, and/or condition of the subject treated and further depending upon the route by which the composition is to be administered. The composition may comprise between 0.1% and 100% (w/w) agent.

Excipients and accessory ingredients used in the manufacture of provided drug delivery vehicles include inert diluents, dispersing and/or granulating agents, surface active agents and/or emulsifiers, disintegrating agents, binding agents, preservatives, buffering agents, lubricating agents, and/or oils. Excipients and accessory ingredients, such as cocoa butter, PEGylated lipids, phospholipids, suppository waxes, coloring agents, coating agents, sweetening, flavoring, and perfuming agents, may also be present.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan monostearate (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *Litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

In certain embodiments, the agent is a polynucleotide. In certain embodiments, the polynucleotide carries out RNA interference. In certain embodiments, the polynucleotide is DNA. In certain embodiments, the polynucleotide is RNA. The RNA is selected from the group consisting of double-stranded RNA (dsRNA), small interfering RNA (siRNA), short hairpin (shRNA), microRNA (miRNA), messenger RNA (mRNA), antisense RNA, transfer RNA (tRNA), small nuclear RNA (snRNA), and ribosomal RNA (rRNA). In certain embodiments, the RNA is dsRNA. In certain embodiments, the RNA is siRNA. In certain embodiments, the RNA is shRNA. In certain embodiments, the RNA is miRNA. In certain embodiments, the RNA is mRNA. In certain embodiments, the RNA is antisense RNA.

In certain embodiments, the agent described herein is provided in an effective amount in the drug delivery vehicle. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof. In certain embodiments, the effective amount is an amount effective for treating a hematological disease in a subject in need thereof. In certain embodiments, the effective amount is an amount effective for preventing a hematological disease in a subject in need thereof. In certain embodiments, the effective amount is an amount effective for treating a neurological disease in a subject in need thereof. In certain embodiments, the effective amount is an amount effective for preventing a neurological disease in a subject in need thereof. In certain embodiments, the effective amount is an amount effective for treating a in a painful condition subject in need thereof. In certain embodiments, the effective amount is an amount effective for preventing a painful condition in a subject in need thereof. In certain embodiments, the effective amount is an amount effective for treating a psychiatric disorder in a subject in need thereof. In certain embodiments, the effective amount is an amount effective for preventing a psychiatric disorder in a subject in need thereof. In certain embodiments, the effective amount is an amount effective for treating a metabolic disorder in a subject in need thereof. In certain embodiments, the effective amount is an amount effective for preventing a metabolic disorder in a subject in need thereof. In certain embodiments, the effective amount is an amount effective for reducing the risk of developing a disease (e.g., proliferative disease, hematological disease, neurological disease, painful condition, psychiatric disorder, or metabolic disorder) in a subject in need thereof. In certain embodiments, the effective amount is an amount effective for inhibiting the activity (e.g., aberrant activity, such as increased activity) of a protein kinase in a subject or cell.

In certain embodiments, the cell is in vitro. In certain embodiments, the cell is in vivo.

The exact amount of an agent required to achieve an effective amount will vary from subject to subject, depending, for example, on species, age, and general condition of a subject, severity of the side effects or disorder, identity of the particular agent, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a polymer described herein. In certain embodiments, a dose described herein includes independently between 1 mg and 3 mg, inclusive, of a polymer described herein. In certain embodiments, a dose described herein includes independently between 3 mg and 10 mg, inclusive, of a polymer described herein. In certain embodiments, a dose described herein includes independently between 10 mg and 30 mg, inclusive, of a polymer described herein. In certain embodiments, a dose described herein includes independently between 30 mg and 100 mg, inclusive, of a polymer described herein.

Dose ranges as described herein provide guidance for the administration of provided compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the polymer or composition described herein in a single dose or administered separately in different doses. The particular combination to employ in a regimen will take into account compatibility of the polymer described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include anti-proliferative agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is a binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and *vinca* alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the polymers described herein or pharmaceutical compositions can be administered in combination with an anti-cancer therapy including surgery, radiation therapy, transplantation (e.g., stem cell transplantation, bone marrow transplantation), immunotherapy, and chemotherapy.

In certain embodiments, the agents described herein are effective therapeutics for a disease or condition that is a genetic disease, proliferative disease, hematological disease, neurological disease, painful condition, psychiatric disorder, metabolic disorder, long-term medical condition, cancer (e.g. lung cancer, large bowel cancer, pancreas cancer, biliary tract cancer, or endometrial cancer), neoplasm, angiogenesis, inflammatory disease, autoinflammatory disease, liver disease, lung disease, spleen disease, familial amyloid neuropathy, cardiovascular disease, viral infection, fibrotic condition, or autoimmune disease.

In some embodiments, the drug delivery vehicle is substantially soluble in water (e.g., hydrophilic). In some embodiments, the drug delivery vehicle is substantially insoluble in water (e.g., hydrophobic).

EXAMPLES

Example 1. Preparation of the Compounds of Formula (I)

Exemplary compounds of Formula (I) were prepared according to the method shown in the figures.

Example 2. Preparation of the Polymers of Formula (II)

Exemplary polymers of Formula (II) were prepared according to the method shown in the figures.

Example 3. Electrochemical Stability Test

Figure 10A:
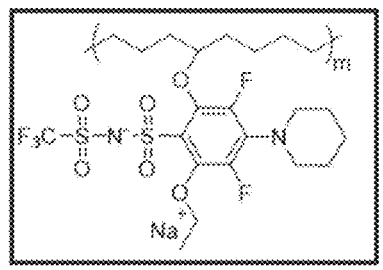
FIG. 10A shows the current observed in the potentiastatic test against Li metal (electrochemical stability test).
Figure 10A:
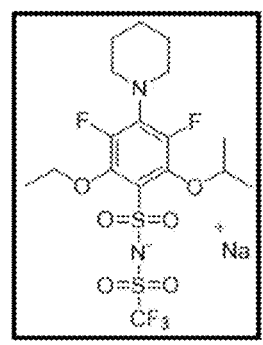
Figure 10A:
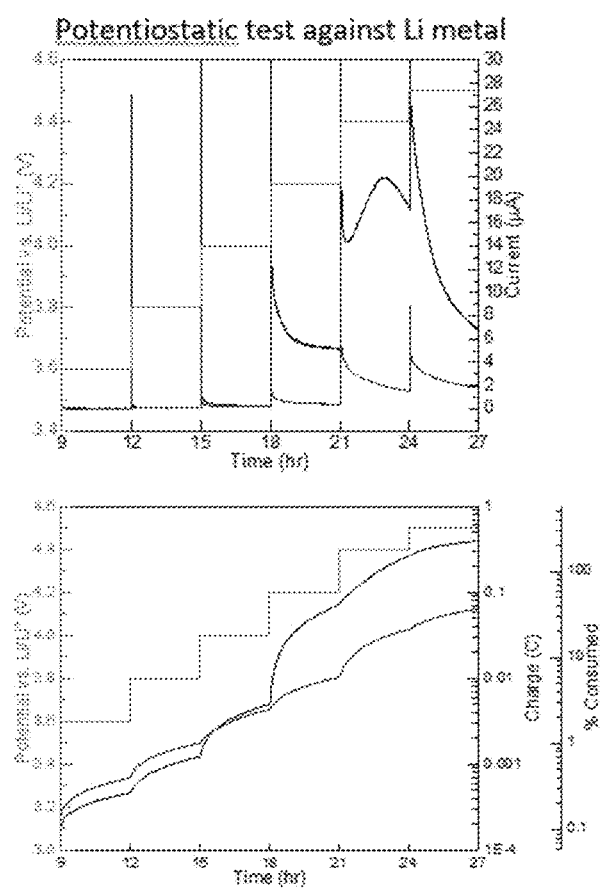
Figure 12:
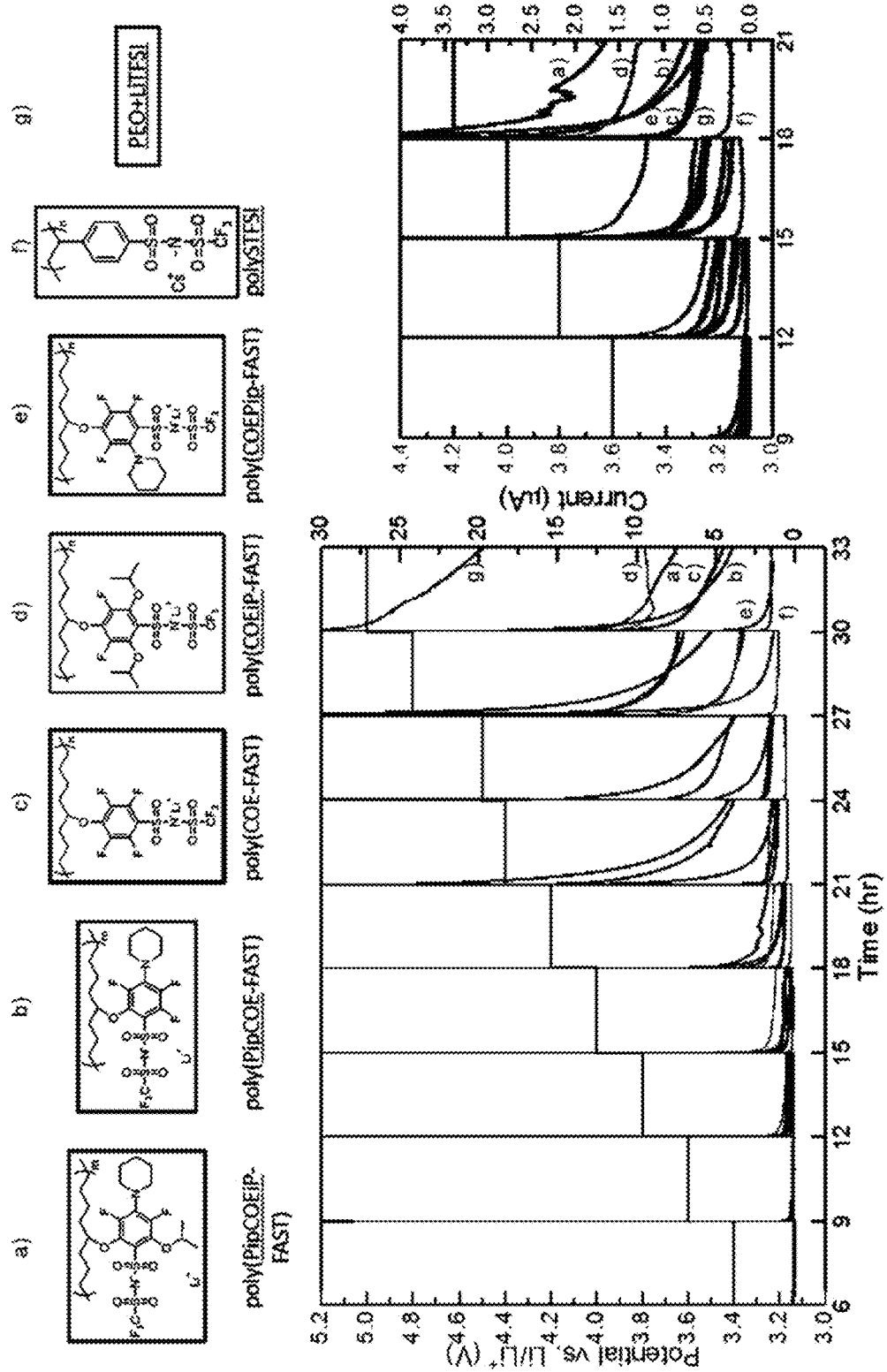
FIG. 12 shows the comparison of electrochemical stabilities between a variety of lithium and cesium sulfonamide polymer electrolytes (0.02 M in PC, Argon, vs. Li). LiTFSI bidentate: 0.511 eV.
Figure 15:
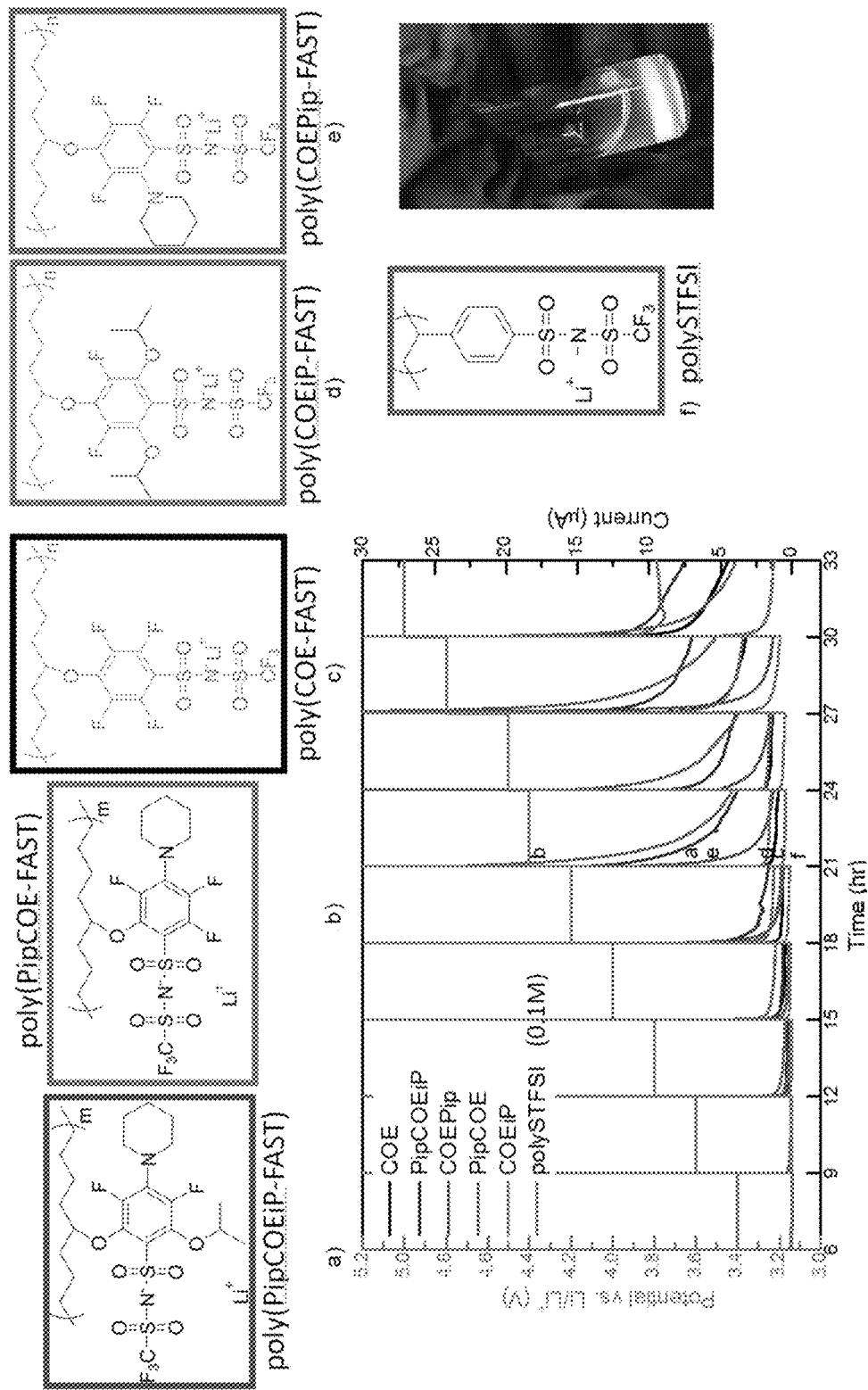
FIG. 15 shows the electrochemical stability of exemplary polymers (0.02 M in PC, Argon, vs. Li). LiTFSI bidentate: 0.511 eV.

Electrochemical stability tests were performed. Exemplary results are shown in FIGS. 10A, 12, and 15. The tested polymer showed good electrochemical stability.

Example 4. Chemical Stability Test

Figure 10B:
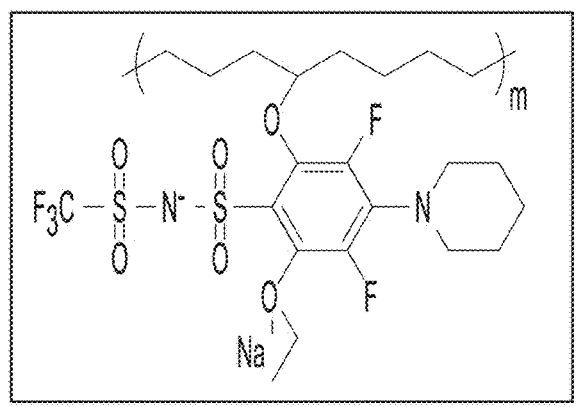
FIG. 10B shows the $^{19}$F NMR spectra observed in a chemical stability test.
Figure 10B:
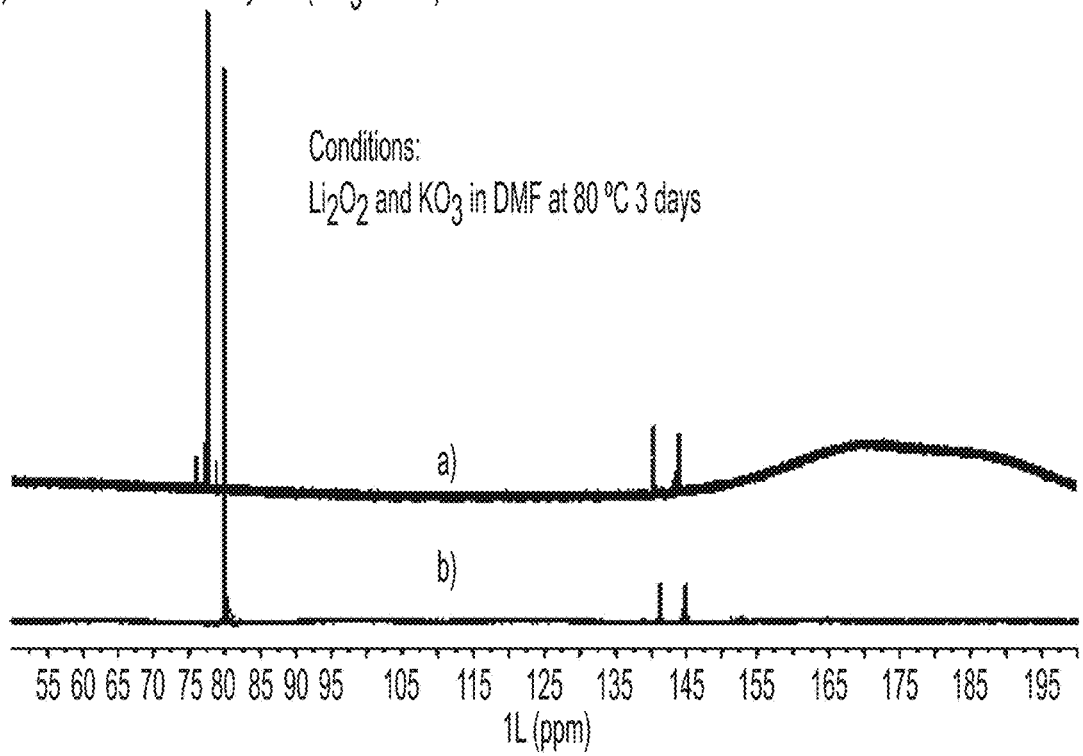
Figure 11:
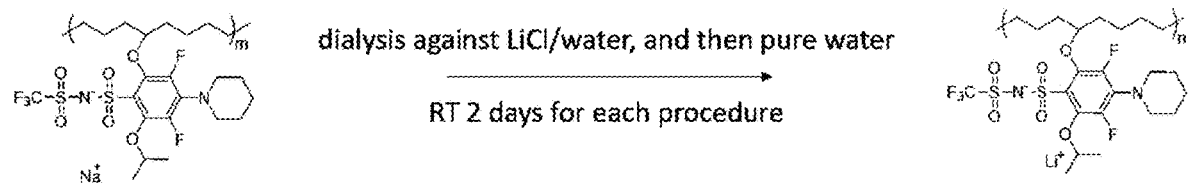
FIG. 11 shows the ion exchange reaction for the conversion of sodium sulfonamide polymer electrolytes to lithium sulfonamide polymer electrolytes.

A chemical stability test was performed. Exemplary results are shown in FIG. 10B. The tested polymer showed good chemical stability.

Example 5. Conductivity Test

Figure 13:
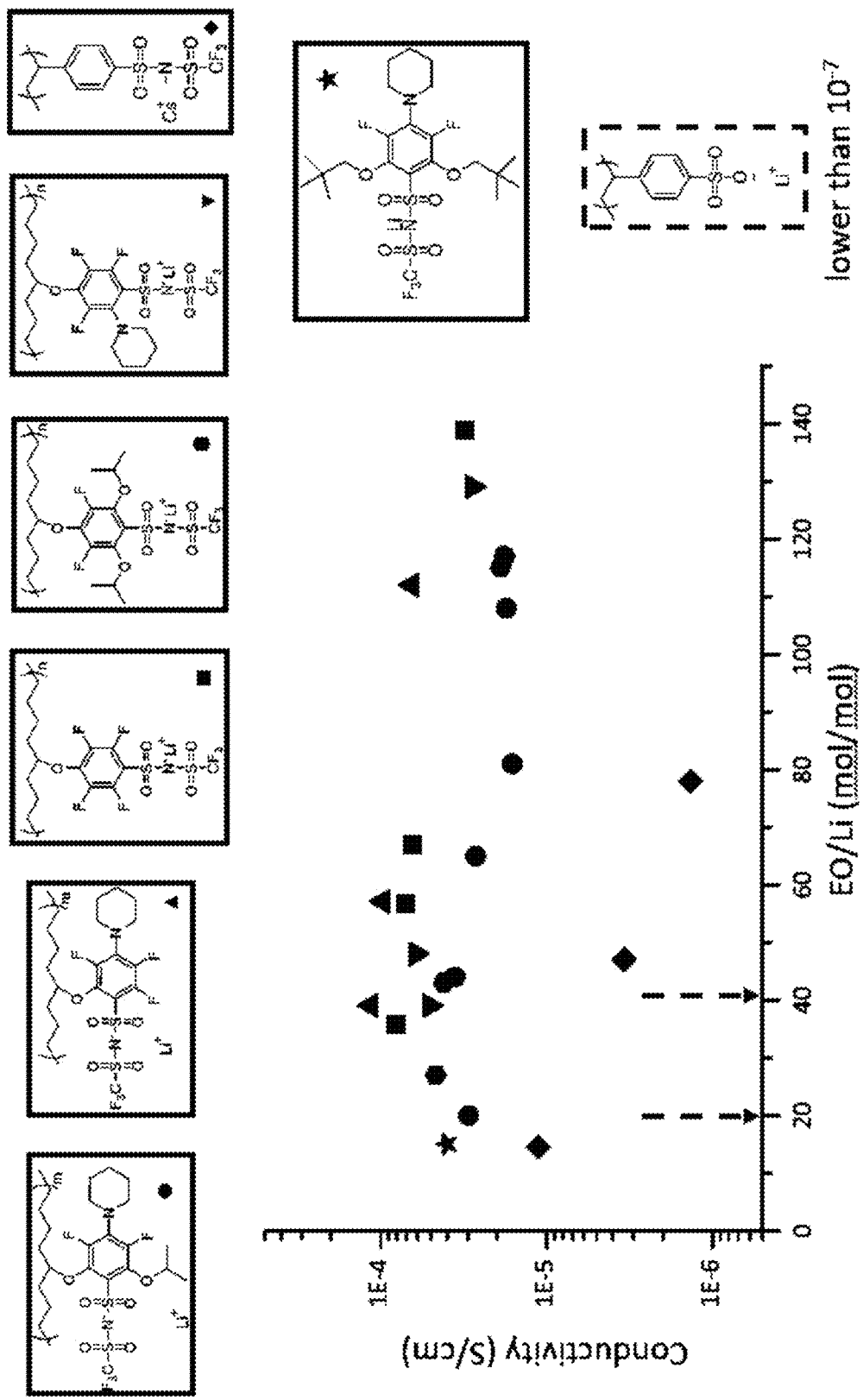
FIG. 13 shows the comparison of conductivities between a variety of lithium sulfonamide polymer electrolytes with PEO as a polymer blend.
Figure 14:
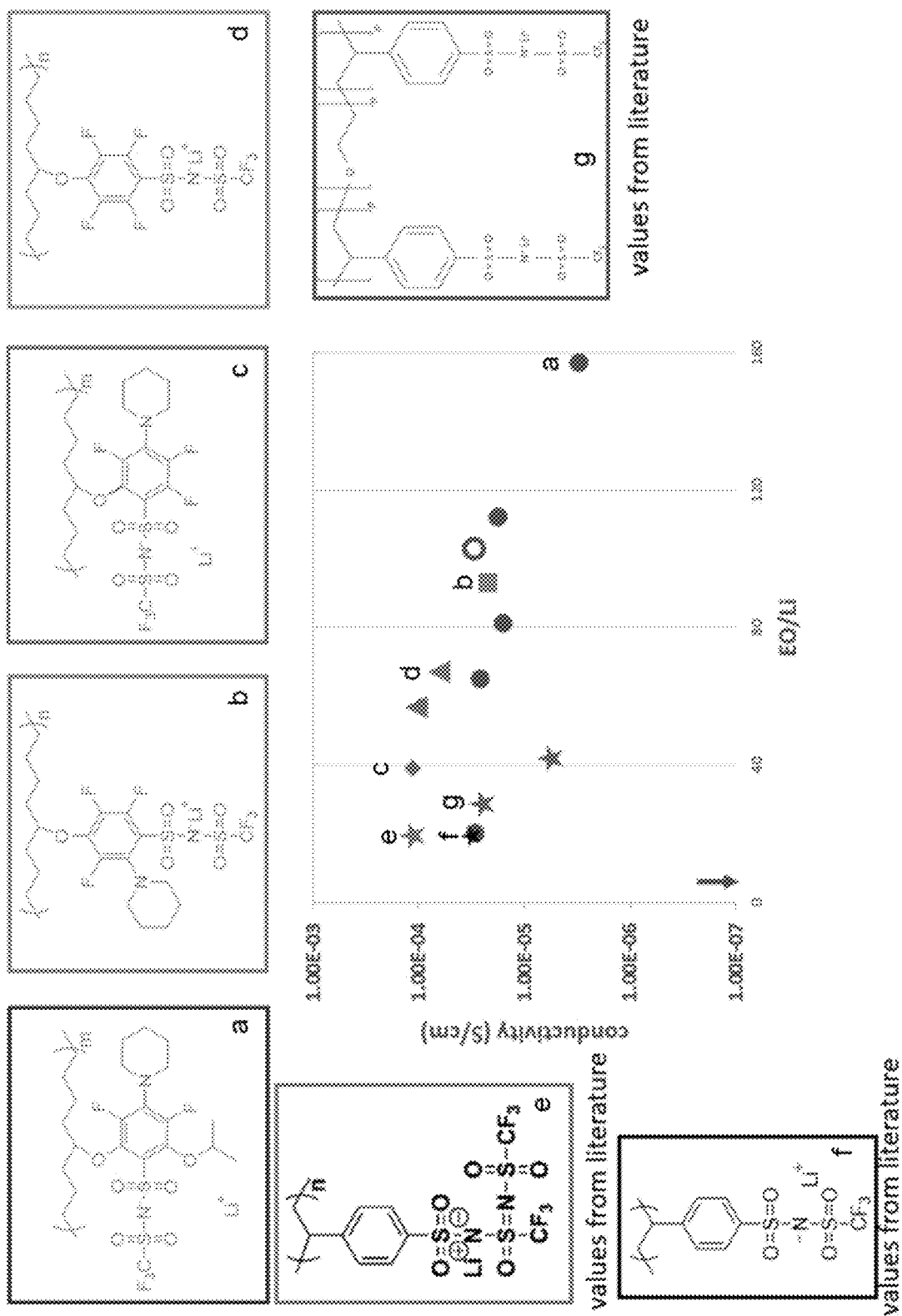
FIG. 14 shows the comparison of conductivities between a variety of lithium sulfonamide polymer electrolytes with PEO as a polymer blend with results from literature. See Z. Zhou et al, Angew. Chem. Int. Ed. 2016, 55, 2521; Armand et al, Nature Materials 2013, 12, 452.
Figure 16:
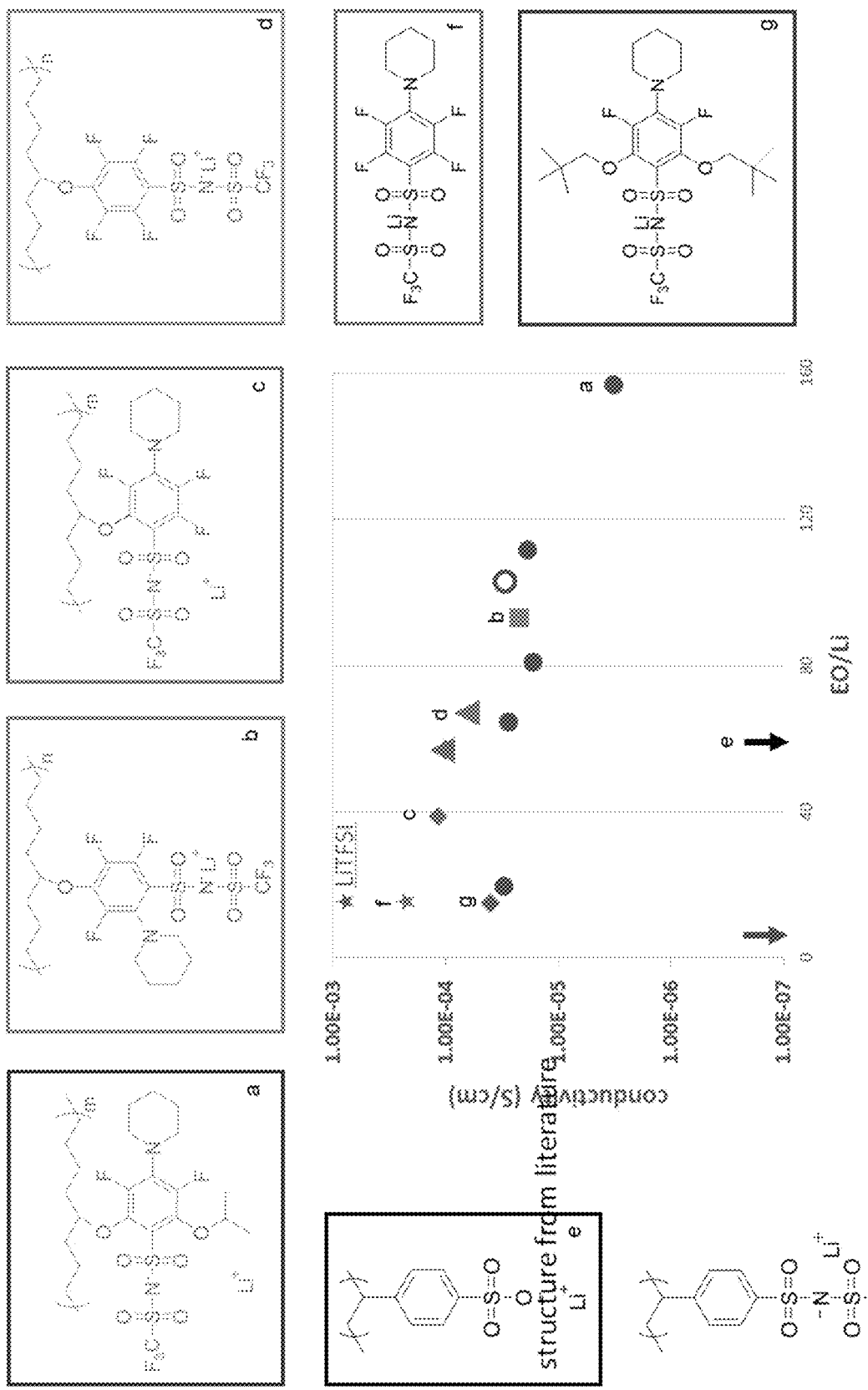
FIG. 16 shows conductivities of select PEO blends.
Figure 17:
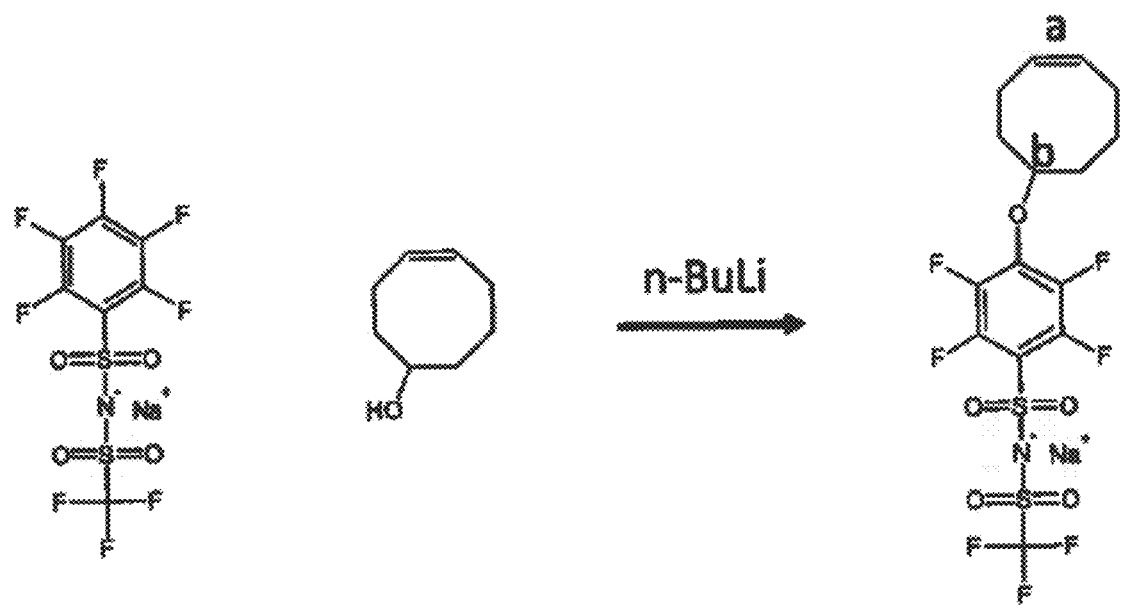
FIGS. 17 to 39 are as described herein.
Figure 18:
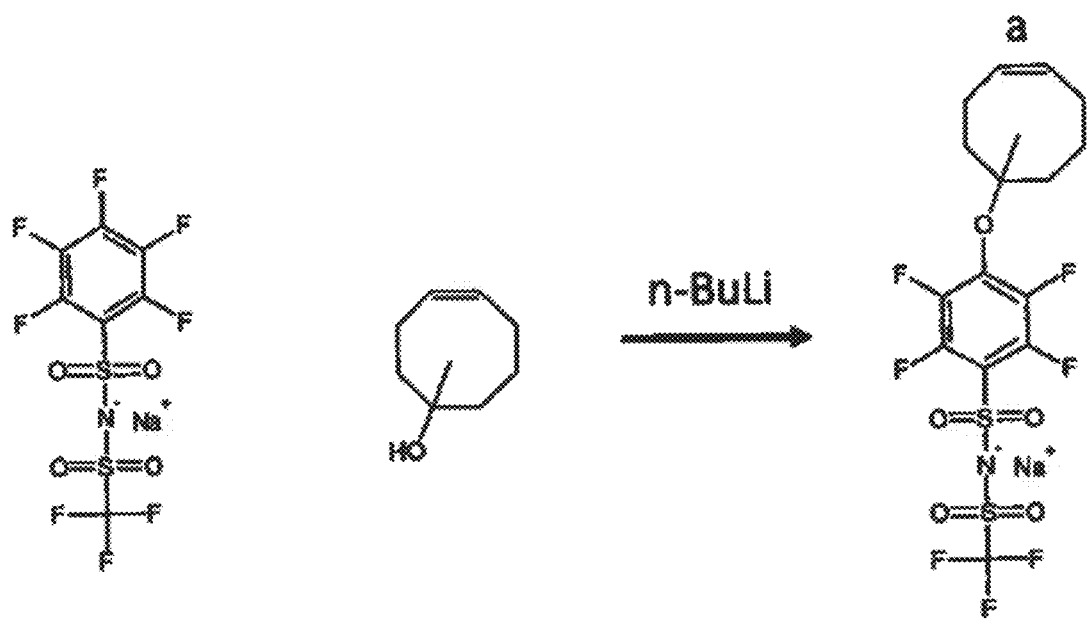
Figure 19:
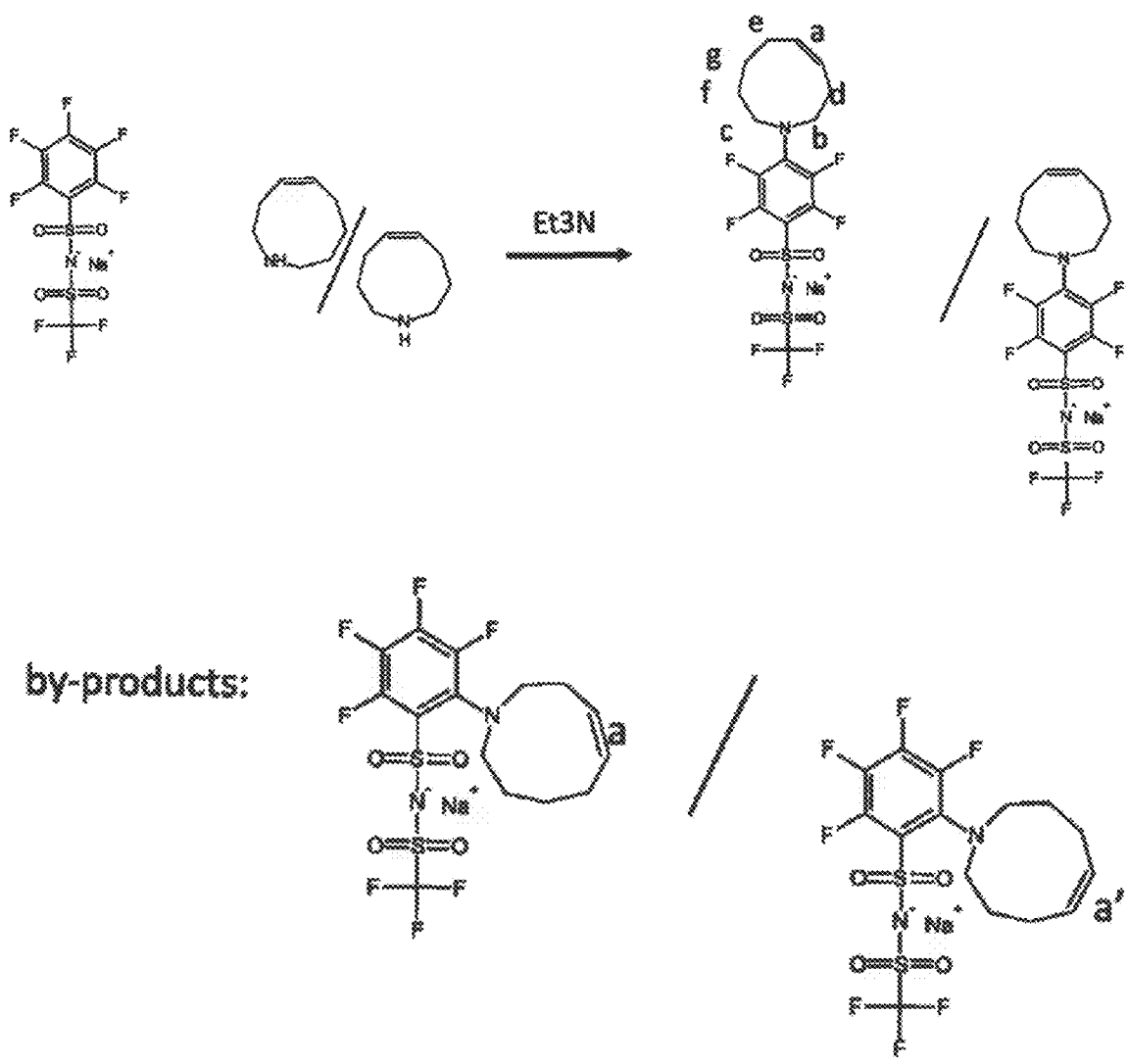
Figure 20:
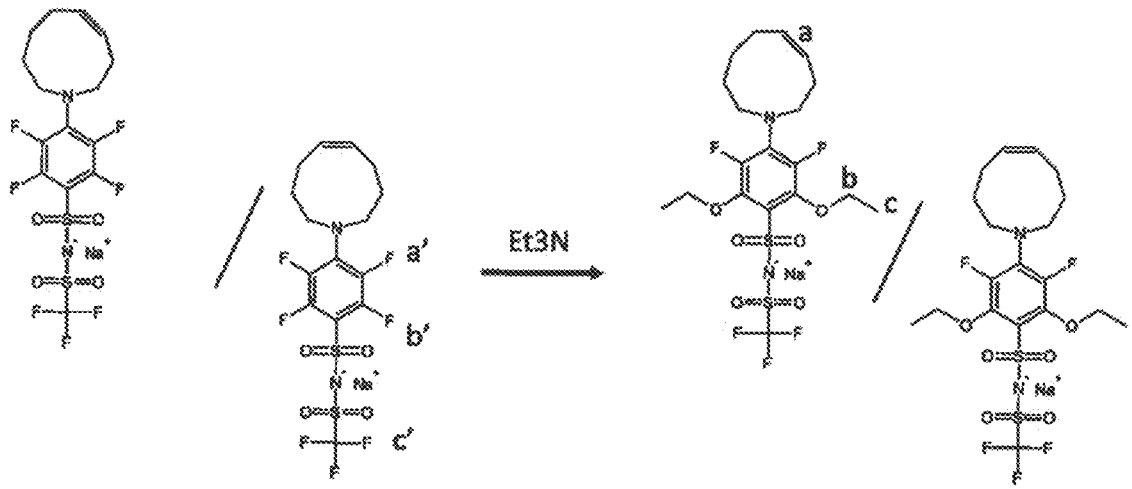
Figure 21:
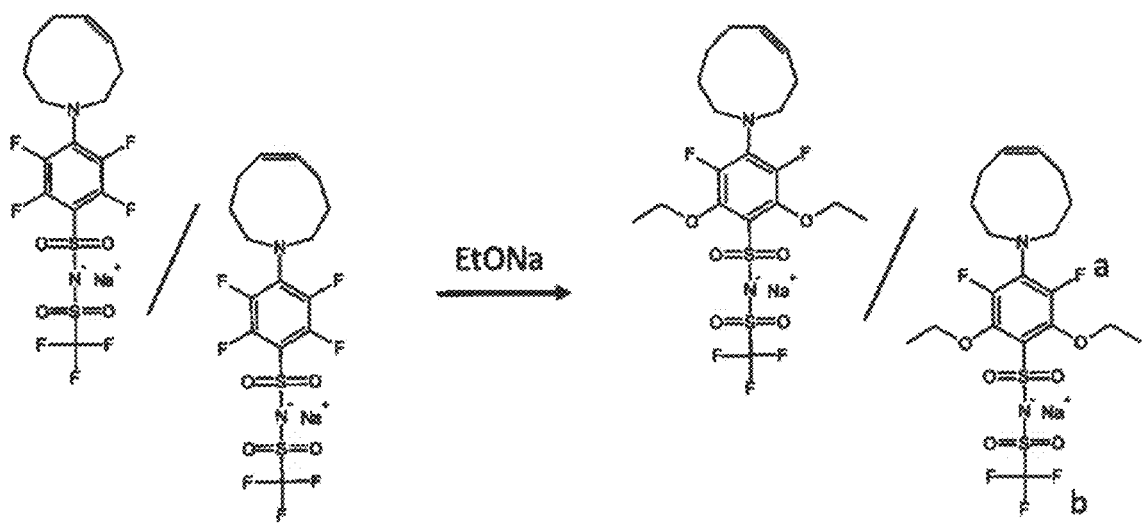
Figure 22:
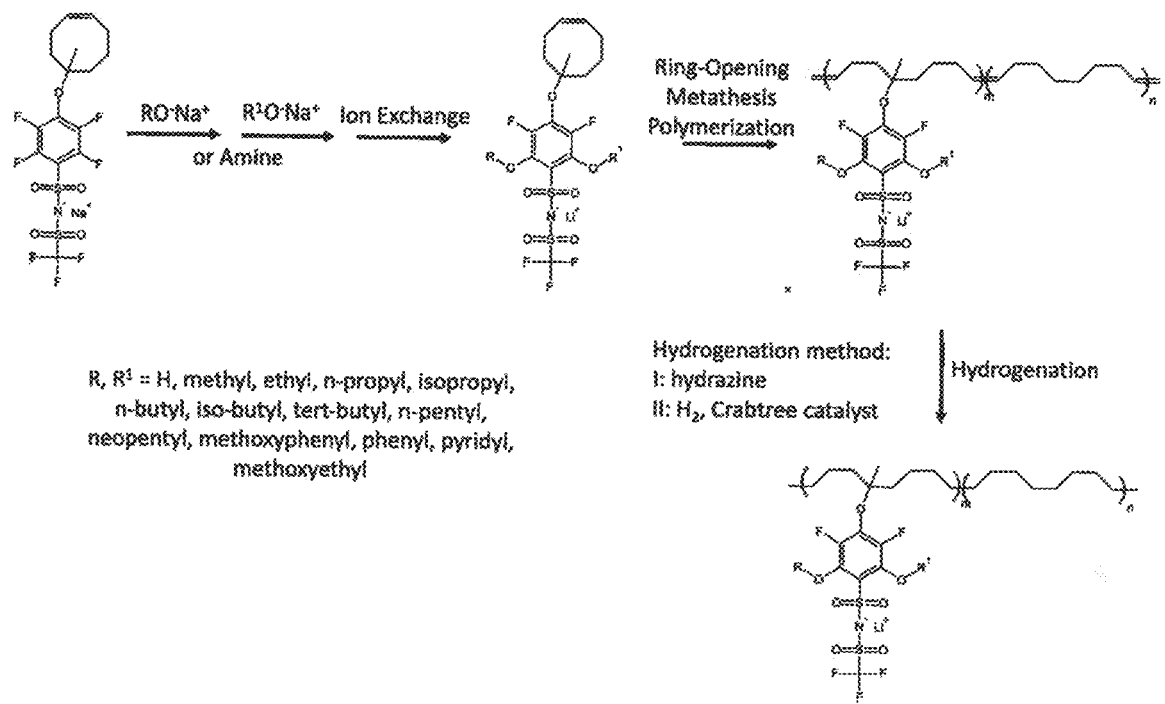
Figure 23:
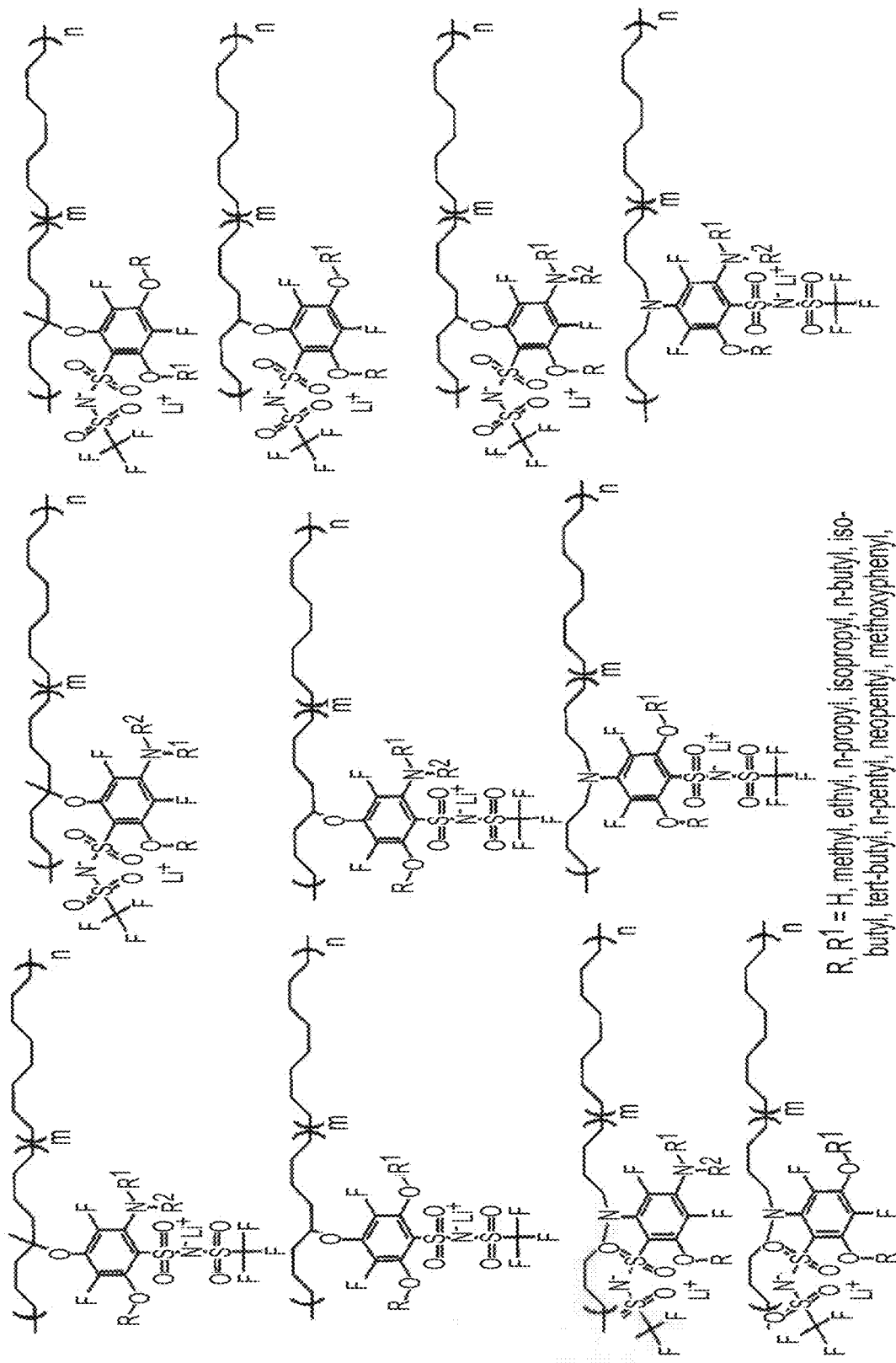
Figure 24:
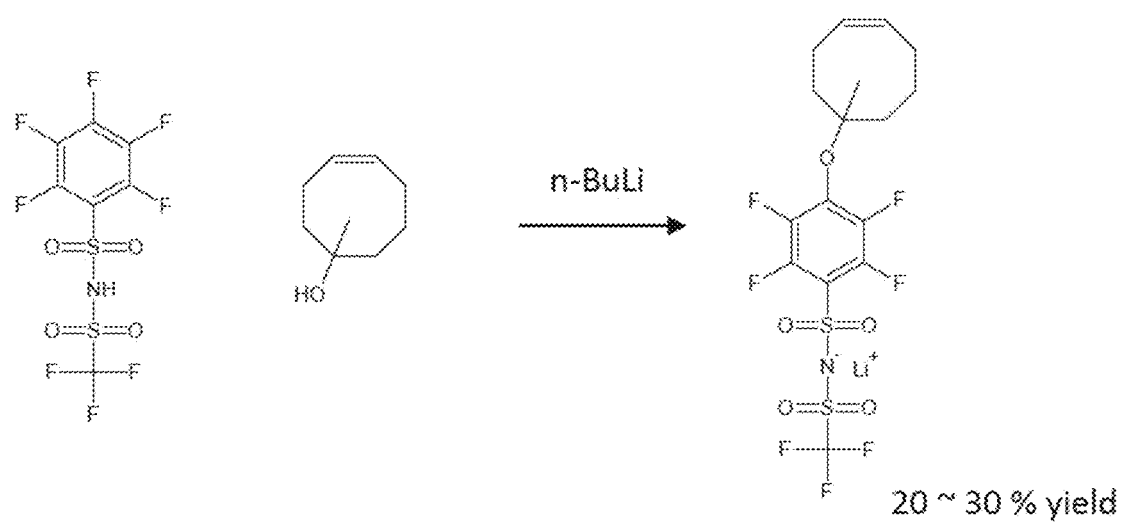
Figure 25:
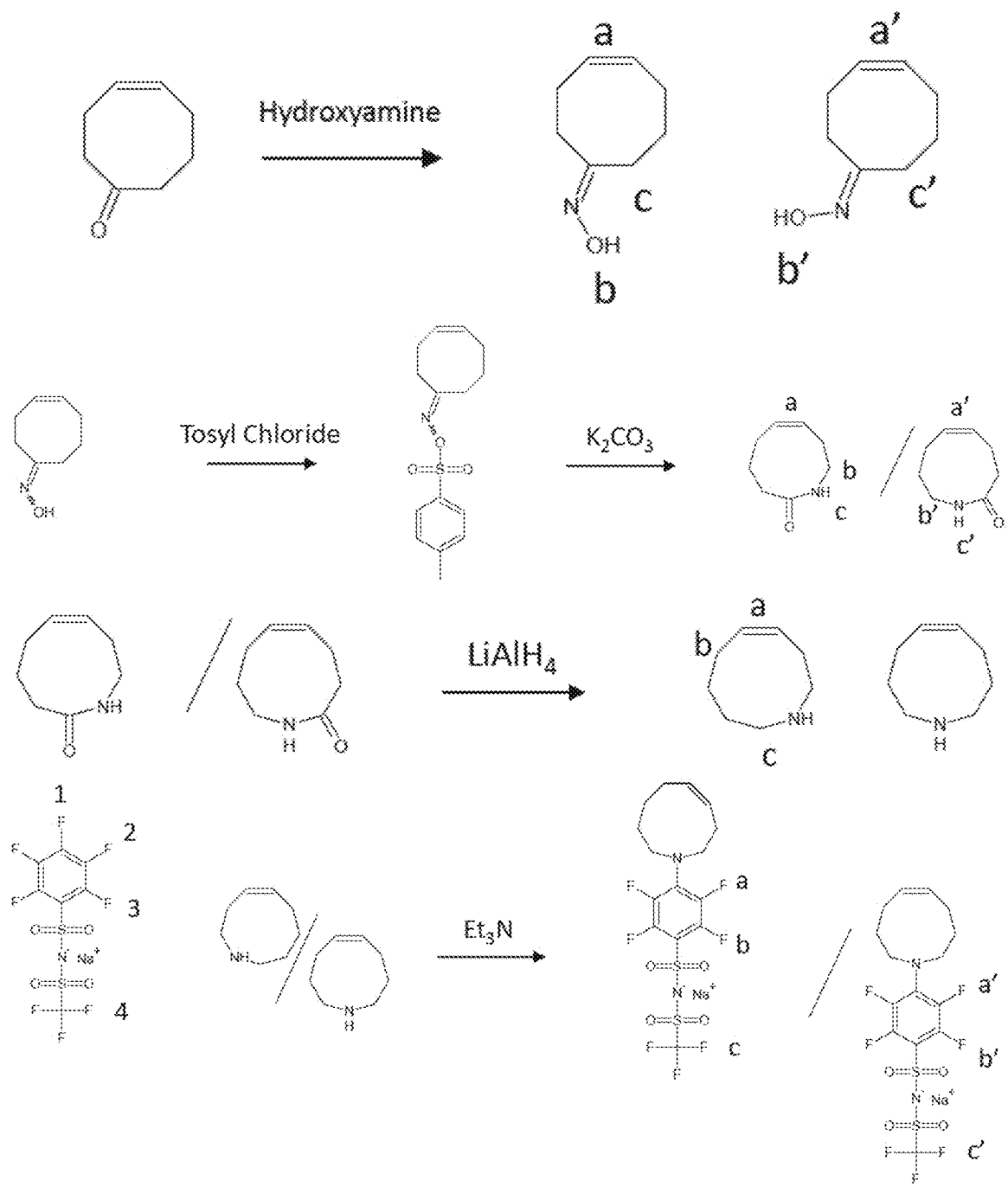
Figure 25:
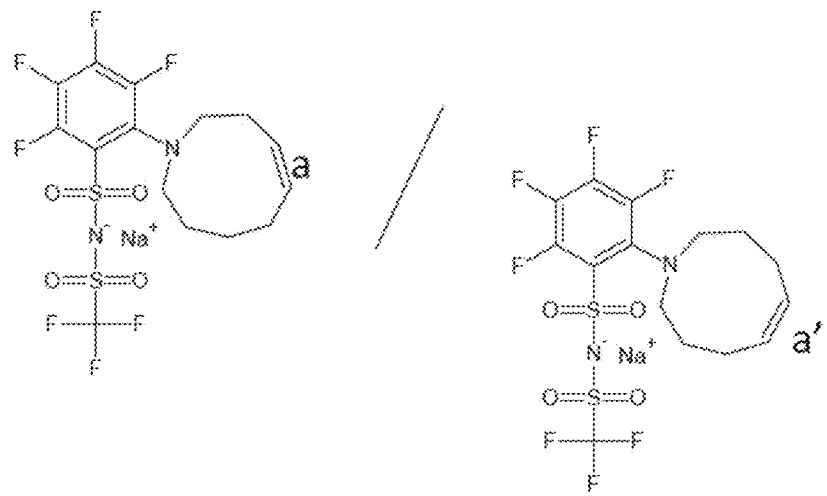
Figure 26:
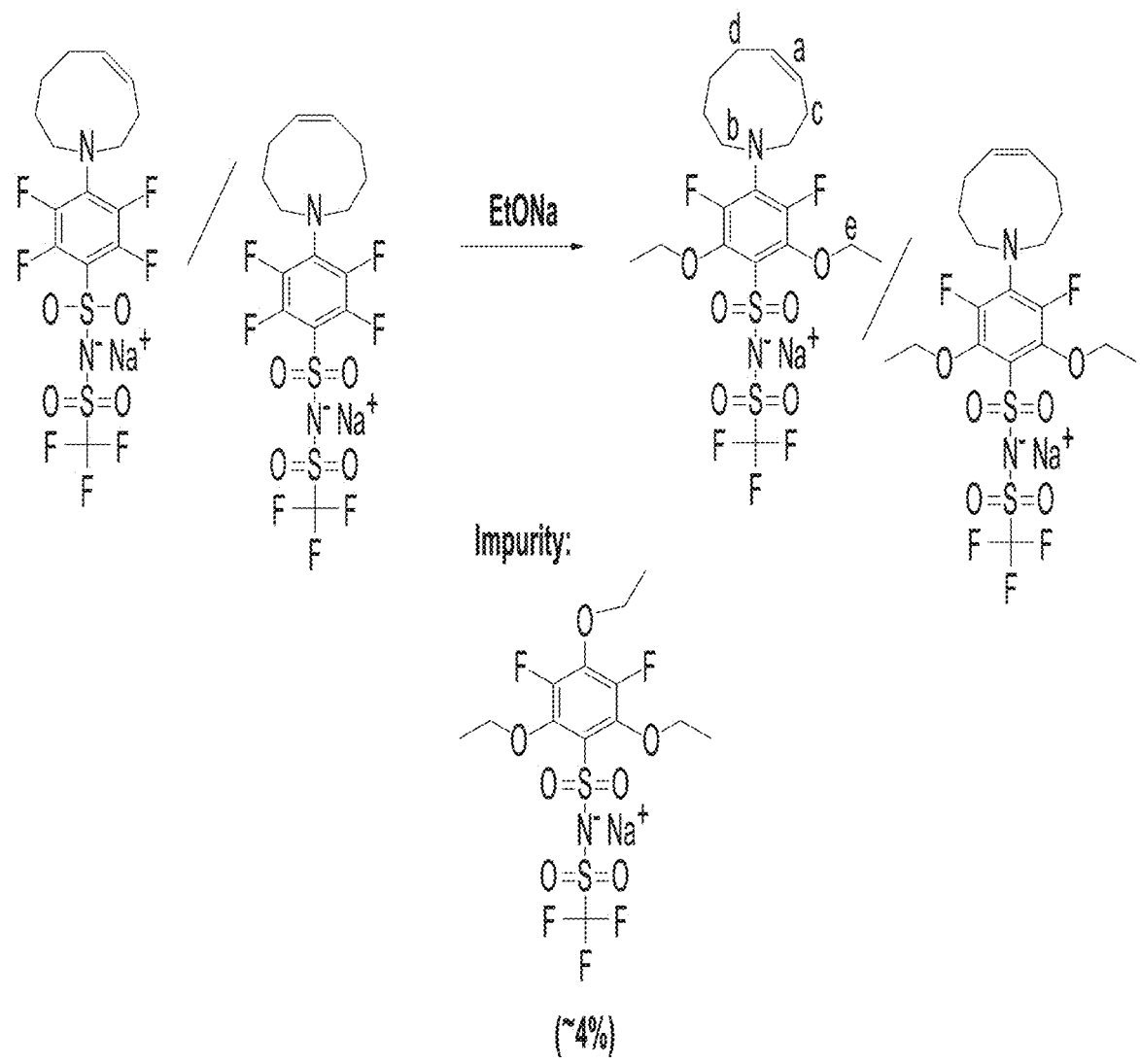
Figure 27:
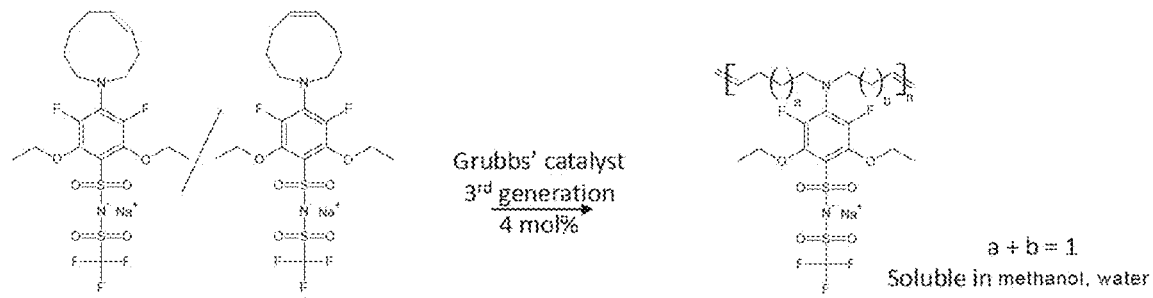
Figure 28:
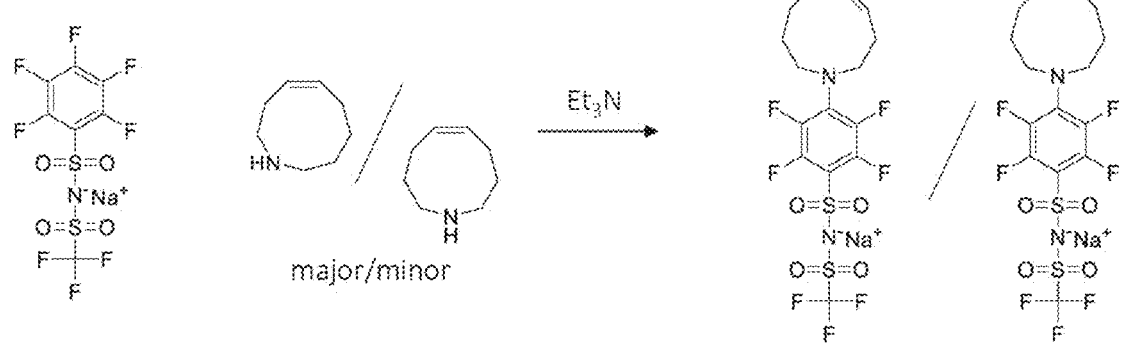
Figure 29:
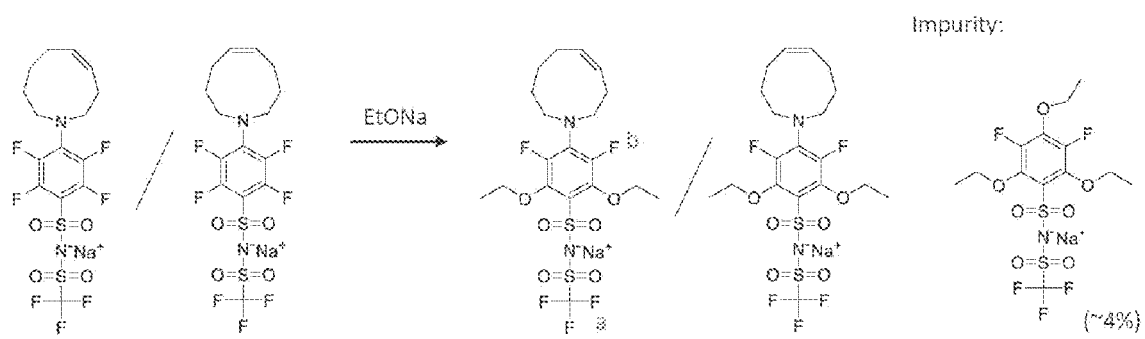
Figure 30:
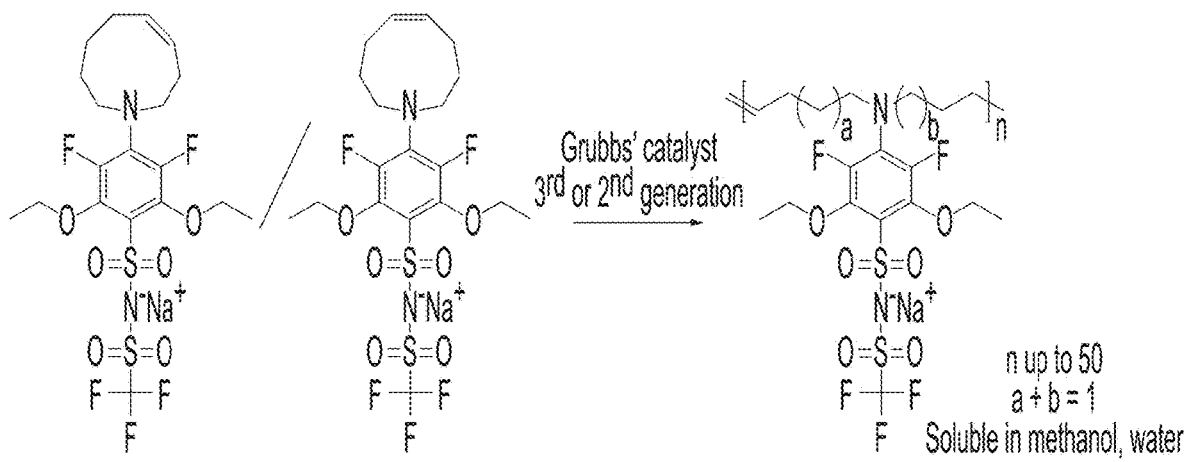
Figure 31:
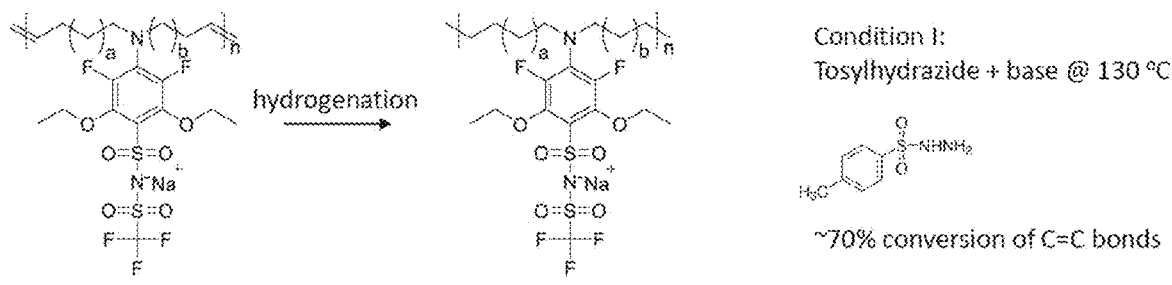
Figure 32:
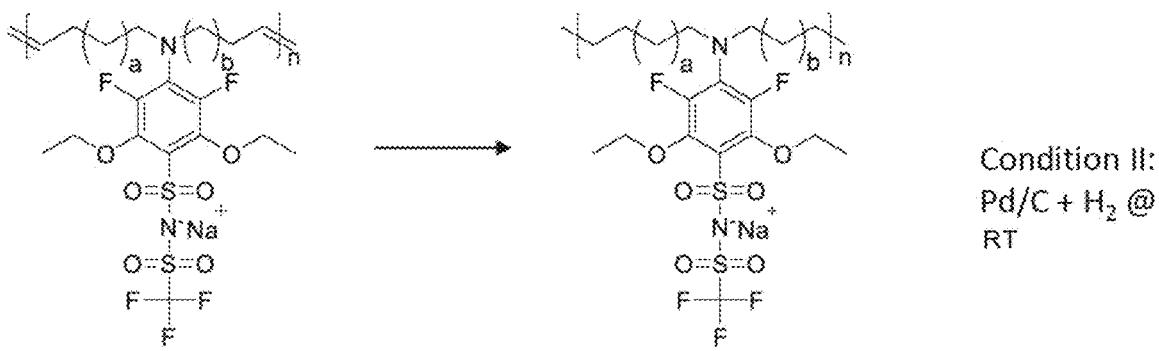
Figure 33:
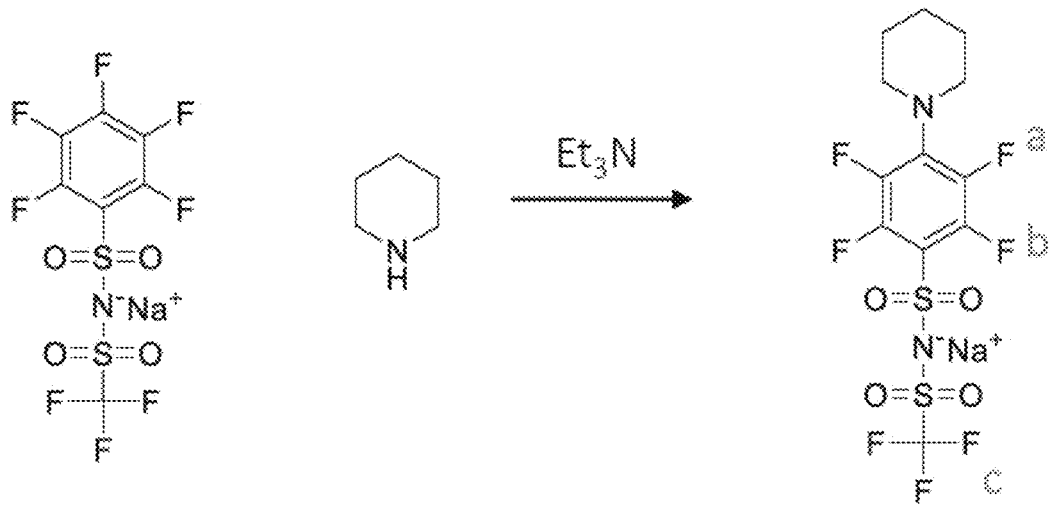
Figure 34:
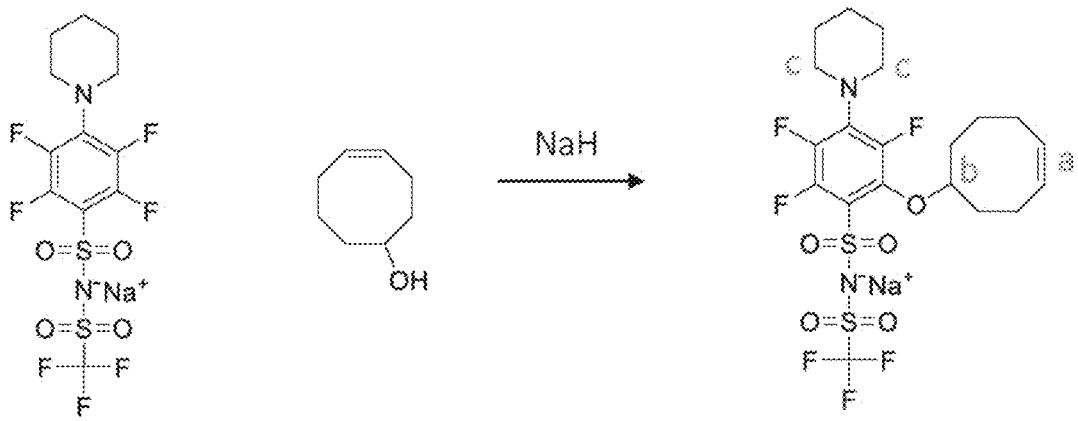
Figure 35:
Figure 36:
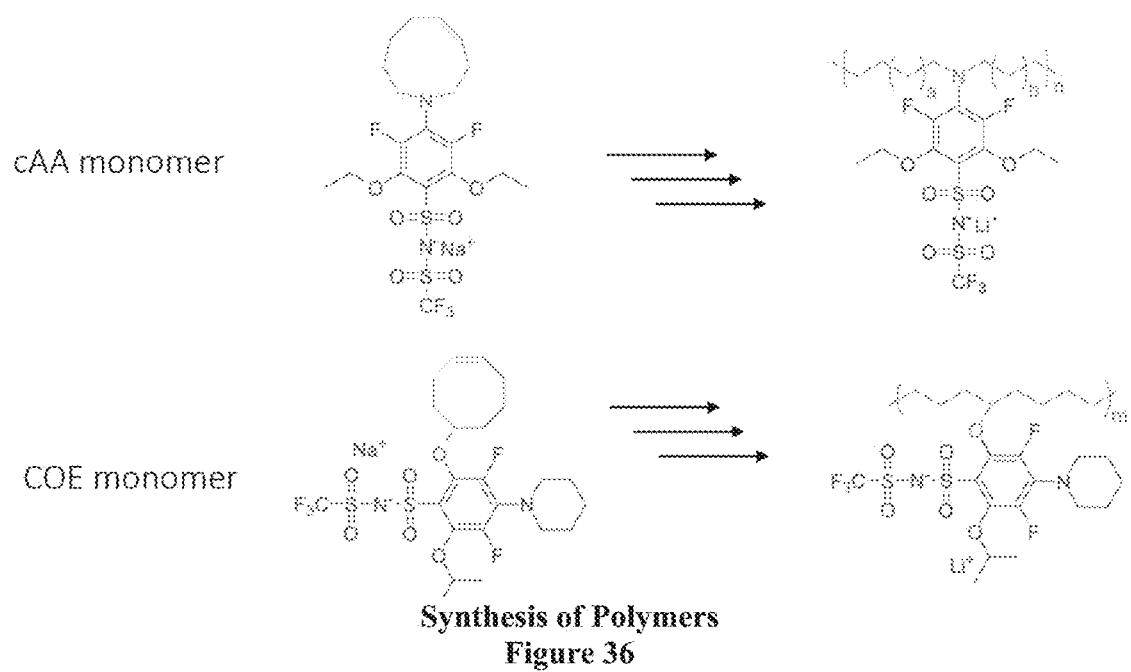
Figure 37:
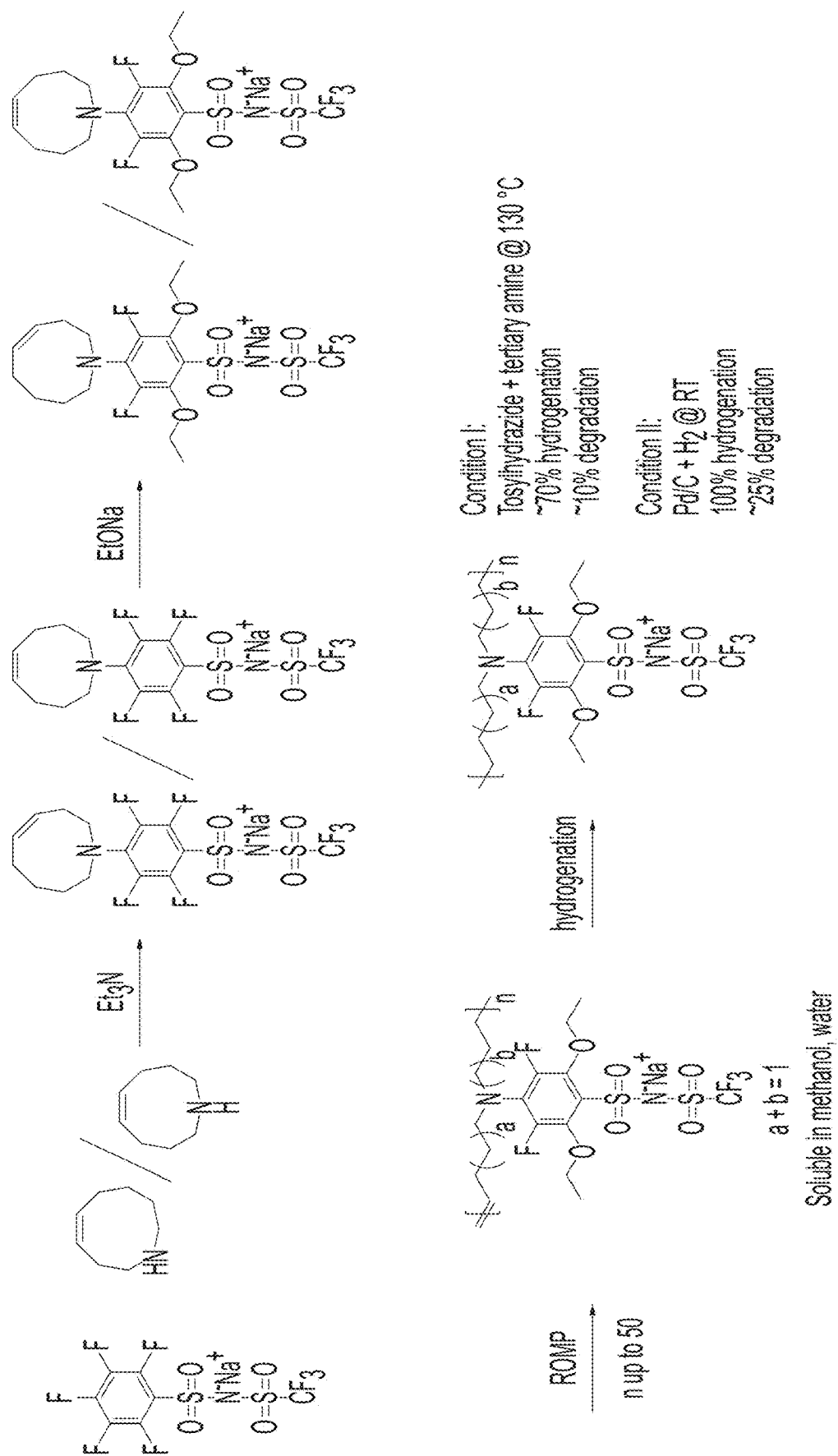
Figure 38:
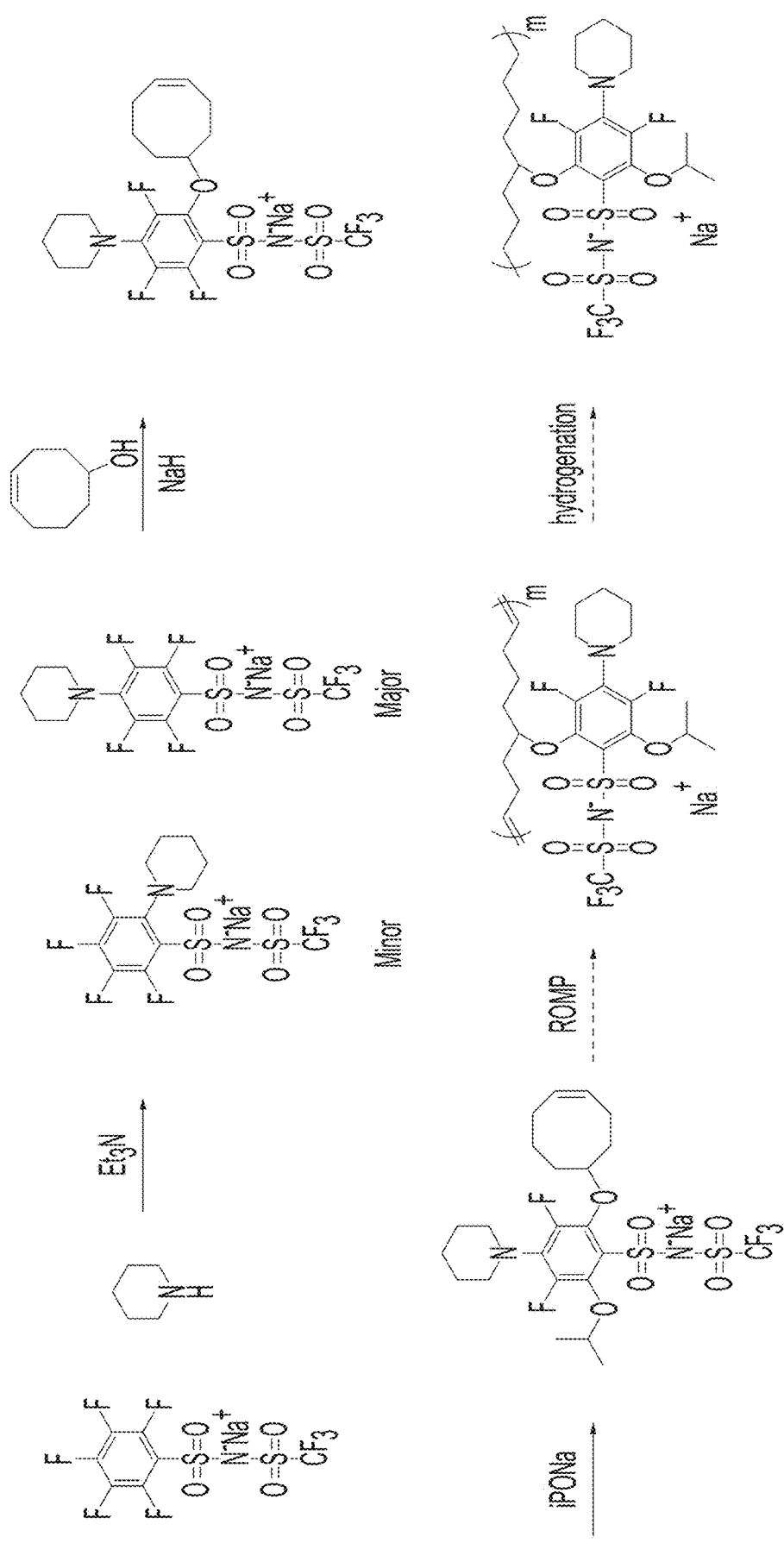
Figure 39:
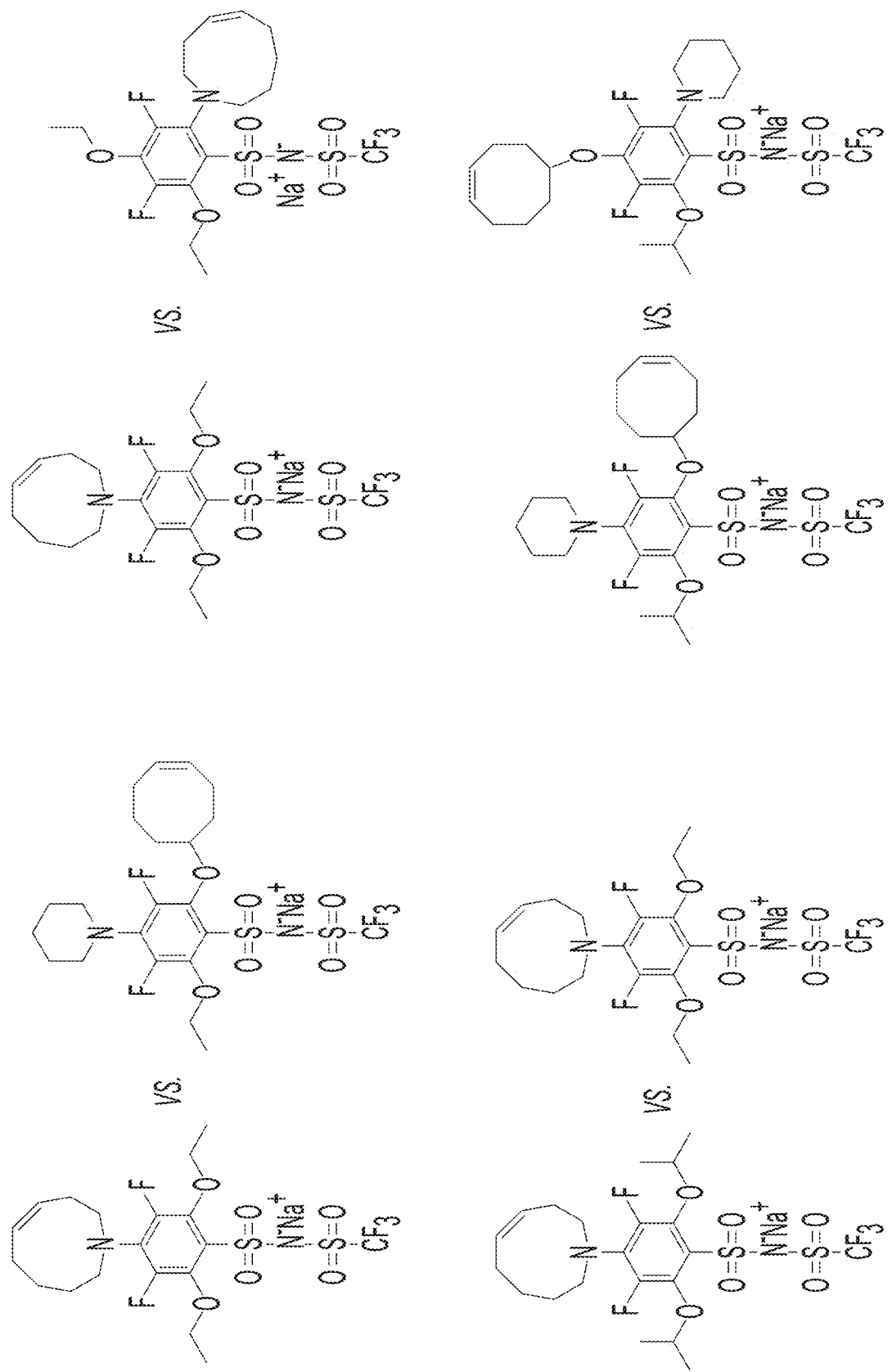

Conductivities of exemplary polymers were determined. Exemplary results are shown in FIGS. 13, 14, and 16. The tested polymer showed good chemical stability.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

REFERENCES

1. Wright, P. V. *British Polymer Journal,* 7 (1975), p. 319.
2. Armand, M. B.; Chabagno, J. M.; Duclot, M. in *Second International Meeting on Solid Electrolytes*, St Andrews, Scotland, 20-22 Sep. 1978, Extended Abstract; M. B. Armand, J. M. Chabagno and M. Duclot, "Poly-ethers as solid electrolytes", in P. Vashitshta, J. N. Mundy, G. K. Shenoy, *Fast ion Transport in Solids. Electrodes and Electrolytes*, North Holland Publishers, Amsterdam, 1979.
3. A) Berthier, C.; Gorecki, W.; Minier, M.; Armand, M. B.; Chabagno, J. M.; Rigaud, P. *Solid State Ionics,* 11 (1983) p. 91; B) Minier, M.; Berthier, C.; Gorecki, W. *Journal de Physique* 45 (1984) p. 739.
4. A) Suo, L.; Borodin, O.; Gao, T.; Olguin, Ma.; Ho, J.; Fan, X.; Luo, C.; Wang, C.; Xu, K. *Science* 350 (2015) p. 938; B) Smith, L.; Dunn, B. *Science* 350 (2015) p. 918.

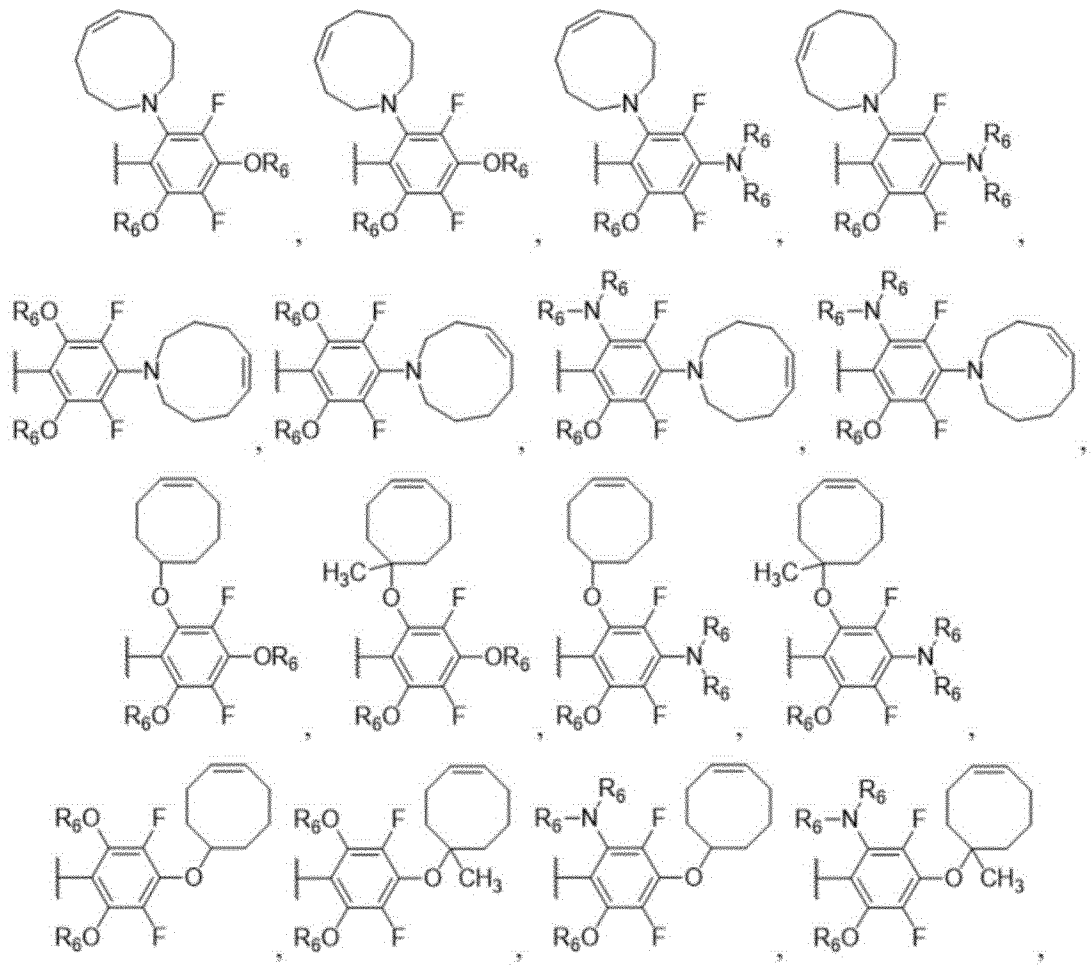

What is claimed is:

1. A compound of Formula (I):

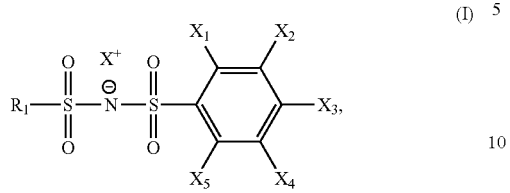

wherein:
- $R_1$ is optionally substituted alkyl or optionally substituted phenyl;
- $X^+$ is a counterion;
- $X_1$, $X_2$, $X_3$, $X_4$ and $X_5$ are independently hydrogen; halogen; optionally substituted, cyclic or acyclic alkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; —$OR_2$; —$N(R_3)_2$; or —$SR_2$;
- each $R_2$ independently is hydrogen; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; optionally substituted heteroaryl; an oxygen protecting group; or a sulfur protecting group; and
- each $R_3$ is independently hydrogen; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; or optionally substituted heteroaryl; a nitrogen protecting group; or two $R_3$ are taken together to form an optionally substituted heterocyclic moiety;
- provided that at least one of $X_1$, $X_2$, $X_3$, $X_4$ and $X_5$ comprises optionally substituted, cyclic or acyclic alkenyl; optionally substituted, cyclic or acyclic heteroalkenyl; optionally substituted, cyclic or acyclic alkynyl; or optionally substituted, cyclic or acyclic heteroalkynyl; and at least two of $X_1$, $X_2$, $X_3$, $X_4$ and $X_5$ are fluorine.

2. The compound of claim 1, wherein $R_1$ is optionally substituted haloalkyl or fluorinated phenyl.

3. The compound of claim 1, wherein $X^+$ is an inorganic cation selected from the group consisting of $Li^+$, $Na^+$, $K^+$, $Rb^+$, $Cs^+$, and $Fr^+$.

4. The compound of claim 1, wherein at least three of $X_1$, $X_2$, $X_3$, $X_4$, and $X_5$ are fluorine.

5. The compound of claim 1, wherein at least one of $X_1$, $X_3$, and $X_5$ is optionally substituted, cyclic or acyclic alkenyl; optionally substituted, cyclic or acyclic heteroalkenyl; optionally substituted, cyclic or acyclic alkynyl; or optionally substituted, cyclic or acyclic heteroalkynyl.

6. The compound of claim 1, wherein at least one of $X_1$, $X_3$, and $X_5$ independently is —$OR_2$, —$N(R_3)_2$ or —$SR_2$.

7. The compound of claim 1, wherein the compound of Formula (I) is of the formula:

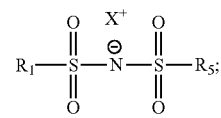

and $R_5$ is selected from the group consisting of:

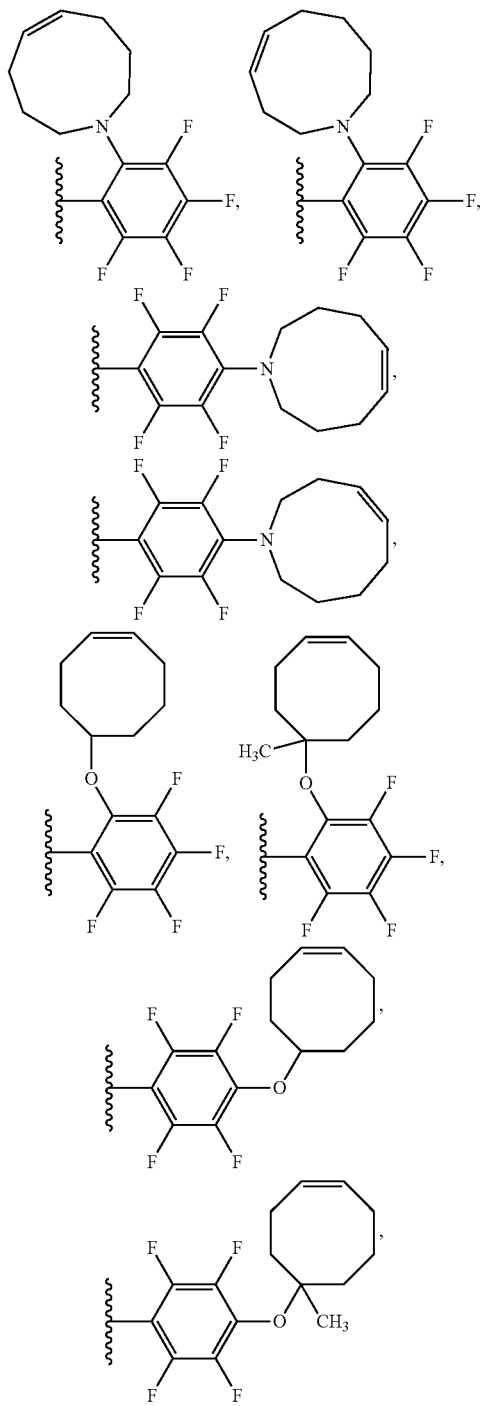

-continued

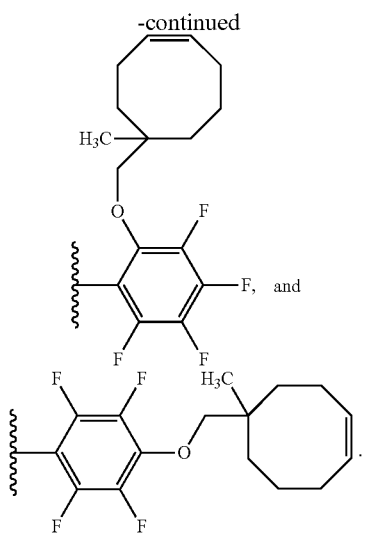

8. A method of preparing a compound of claim 1 comprising reacting a compound of Formula (I-b):

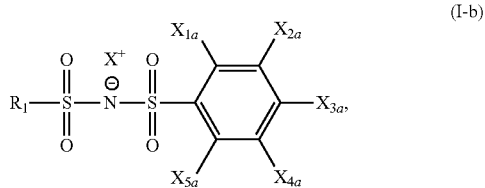

with one or more nucleophiles selected from, or generated from compounds selected from, $HOR_2$, $HN(R_3)_2$, $HSR_2$, and $HC(R_3)_3$, to obtain a compound of Formula (I):

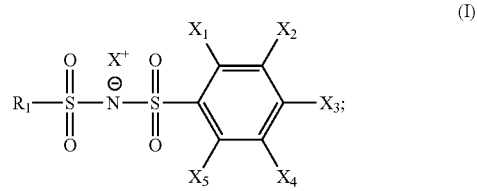

wherein:
$X_{1a}$, $X_{2a}$, $X_{3a}$, $X_{4a}$, and $X_{5a}$ are independently hydrogen; halogen; optionally substituted, cyclic or acyclic alkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted carbonyl; —$OR_2$; —$N(R_3)_2$; or —$SR_2$;

each $R_2$ independently is hydrogen; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; optionally substituted heteroaryl; an oxygen protecting group; or sulfur protecting group; and each $R_3$ independently is hydrogen; optionally substituted, cyclic or acyclic alkyl; optionally substituted, cyclic or acyclic heteroalkyl; optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; optionally substituted aryl; optionally substituted heteroaryl; or a nitrogen protecting group; or two $R_3$ are taken together to form an optionally substituted cyclic alkenyl or an optionally substituted cyclic alkynyl;

provided that at least one of $X_1$, $X_2$, $X_3$, $X_4$ and $X_5$ is optionally substituted, cyclic or acyclic alkenyl; optionally substituted, cyclic or acyclic heteroalkenyl; optionally substituted, cyclic or acyclic alkynyl; optionally substituted, cyclic or acyclic heteroalkynyl; and at least two of $X_1$, $X_2$, $X_3$, $X_4$ and $X_5$ are fluorine; and provided that at least three of $X_{1a}$, $X_{2a}$, $X_{3a}$, $X_{4a}$, and $X_{5a}$ are fluorine.

9. The compound of claim 1, wherein $R^1$ is —$CF_3$.

10. The compound of claim 1, wherein four of $X_1$, $X_2$, $X_3$, $X_4$ and $X_5$ are fluorine.

11. The compound of claim 1, wherein at least one of $X_1$, $X_2$, $X_3$, $X_4$ and $X_5$ comprises optionally substituted, cyclic alkenyl; or optionally substituted, cyclic heteroalkenyl.

12. The compound of claim 1, wherein at least one of $X_1$, $X_3$, and $X_5$ comprises optionally substituted, cyclic alkenyl; or optionally substituted, cyclic heteroalkenyl.

13. The compound of claim 1, wherein the compound of Formula (I) is of one of the following formulae:

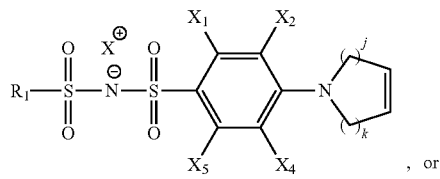, or

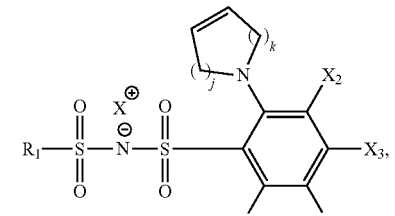

wherein:
j is 0 or an integer between 1 and 4, inclusive; and
k is 0 or an integer between 1 and 3, inclusive.

14. The compound of claim 13, wherein the compound is of one of the following formulae:

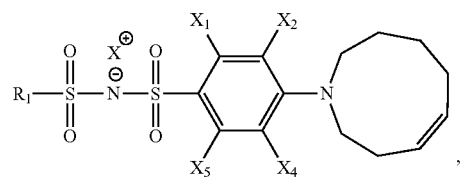

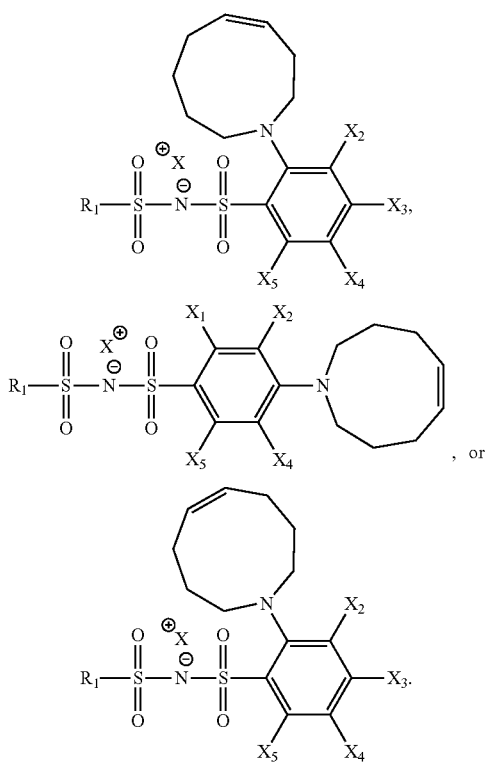
15. The compound of claim 1, wherein the compound of Formula (I) is of one of the following formulae:
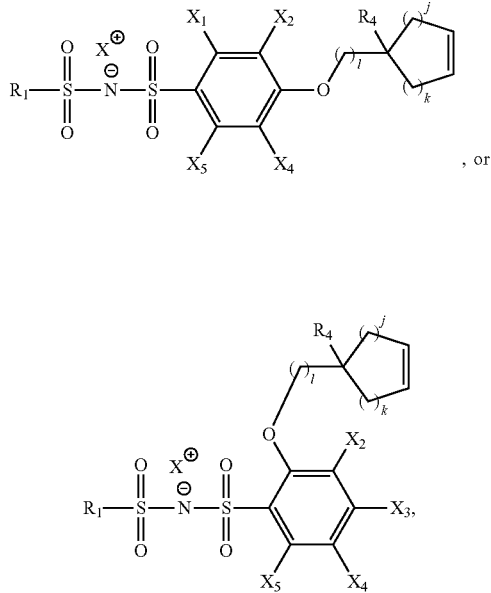
wherein:
  j is 0 or an integer between 1 and 3, inclusive;
  k is 0 or an integer between 1 and 3, inclusive;
  l is 0 or an integer between 1 and 10, inclusive; and
  $R_4$ is hydrogen or optionally substituted acyclic alkyl.
16. The compound of claim 15, wherein the compound is of one of the following formulae:
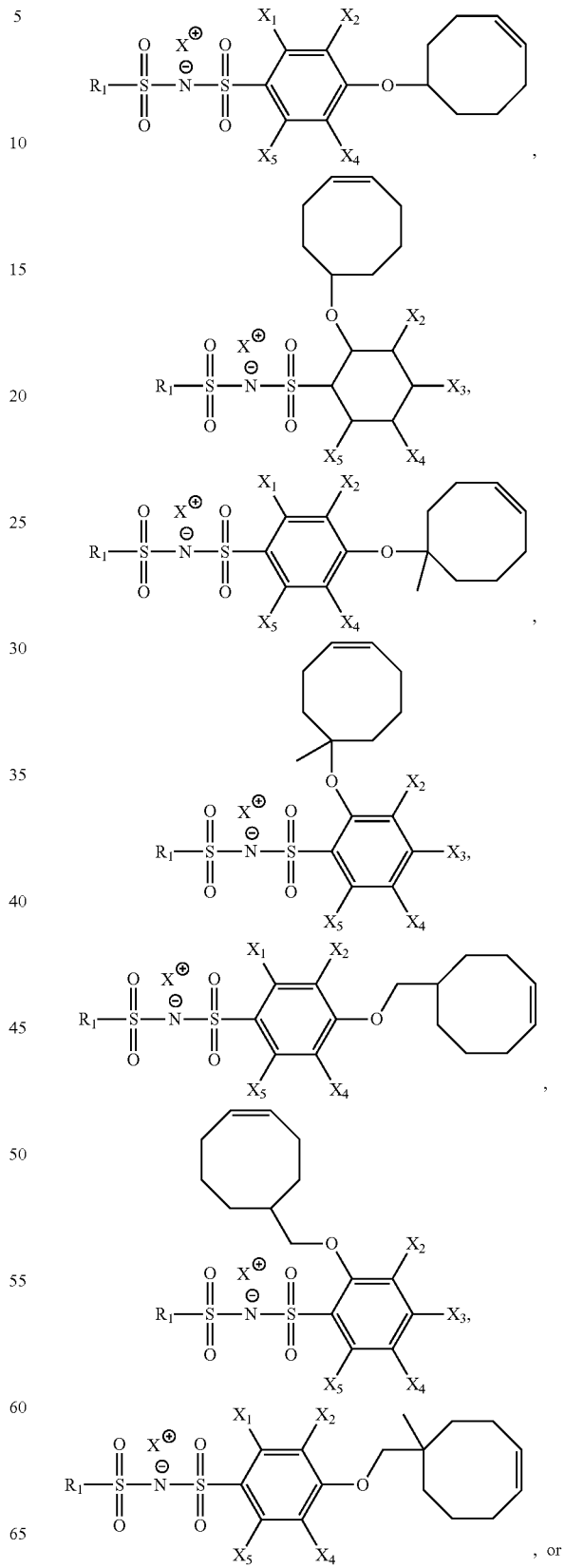

-continued

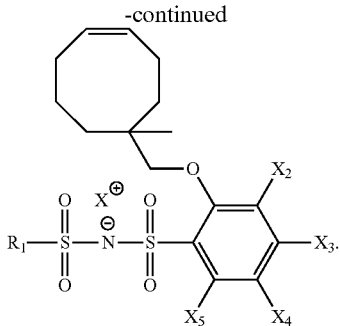

17. The compound of claim 1, wherein the compound of Formula (I) is of one of the following formulae:

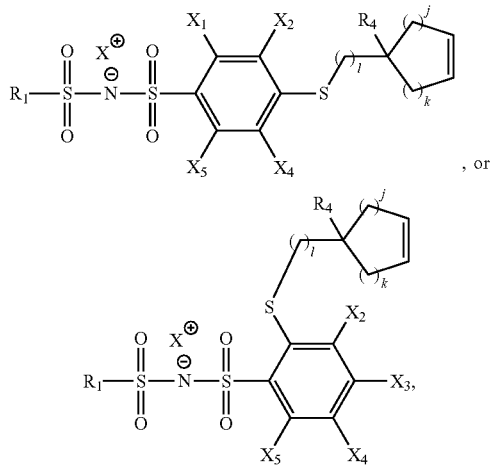

wherein:
j is 0 or an integer between 1 and 3, inclusive;
k is 0 or an integer between 1 and 3, inclusive;
l 0 or an integer between 1 and 10, inclusive; and
$R_4$ is hydrogen or optionally substituted acyclic alkyl.

18. The compound of claim 1, wherein the compound of Formula (I) is of one of the following formulae:

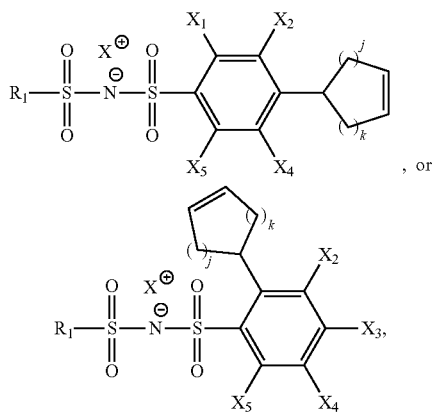

wherein:
j is 0 or an integer between 1 and 3, inclusive; and
k is 0 or an integer between 1 and 3, inclusive.

19. The compound of claim 1, wherein the compound of Formula (I) is of one of the following formulae:

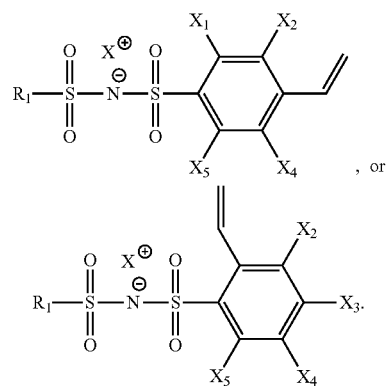

20. The compound of claim 1, wherein the compound of Formula (I) is of formula:

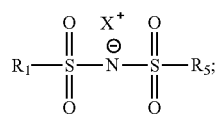

and $R_5$ is selected from the group consisting of:

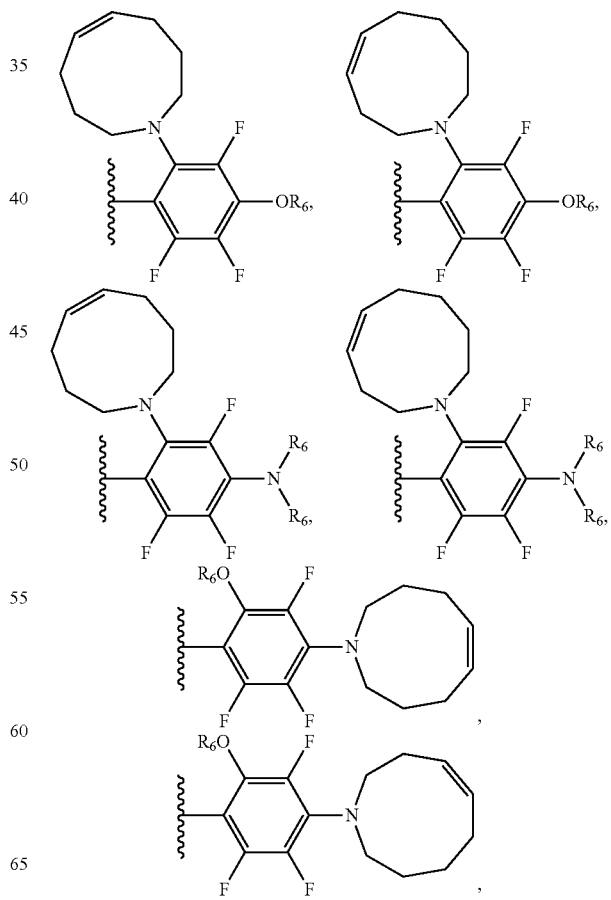

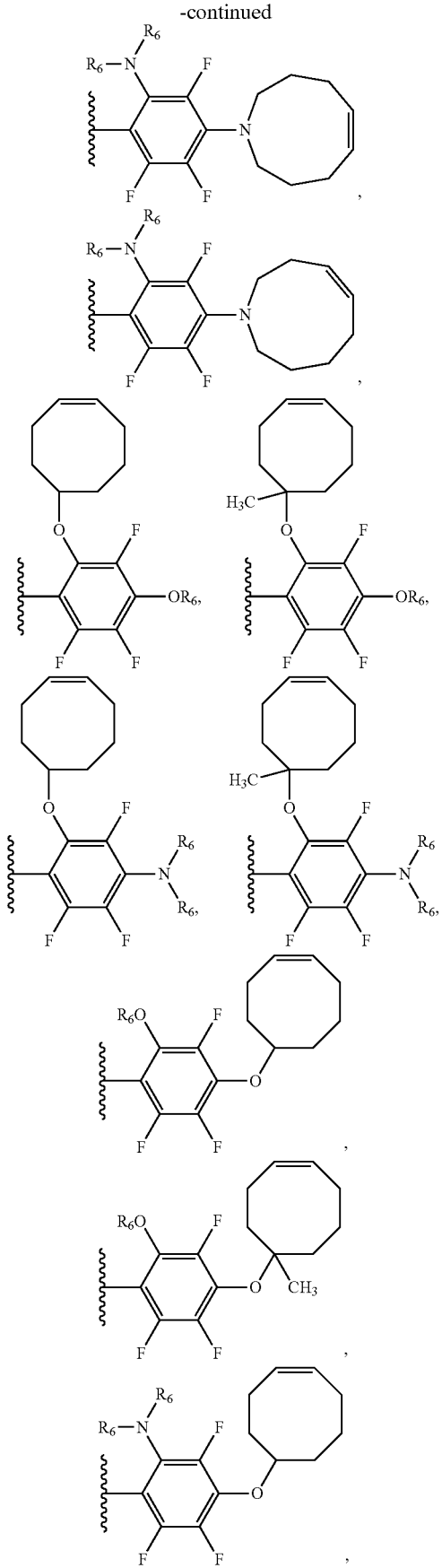
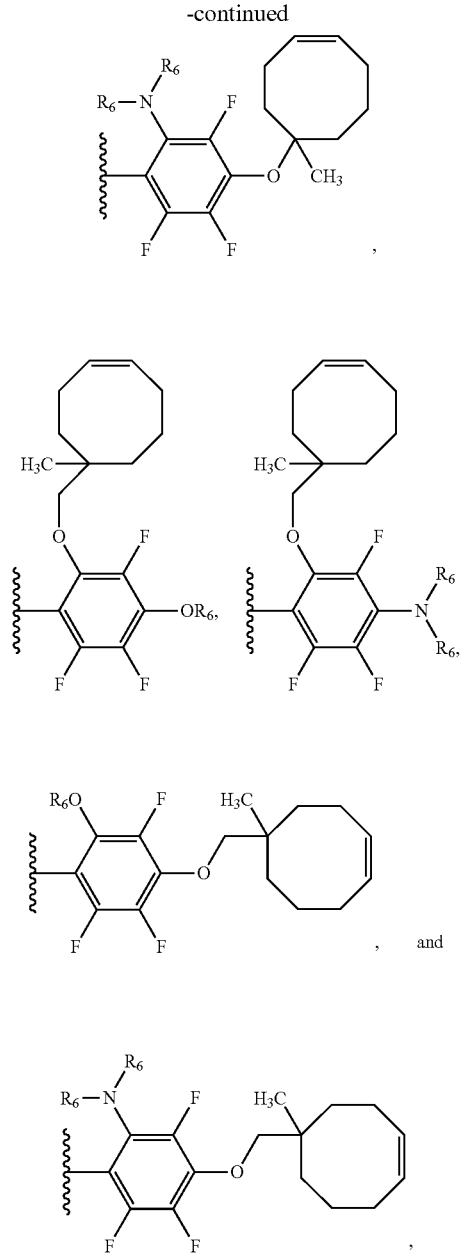
wherein:
each $R_6$ independently is hydrogen; optionally substituted alkyl; optionally substituted heteroalkyl; optionally substituted aryl; or optionally substituted heteroaryl; or two $R_6$ bonded to the same atom are taken together to form an optionally substituted cyclic heteroalkyl.
21. The compound of claim 1, wherein the compound of Formula (I) is of formula:
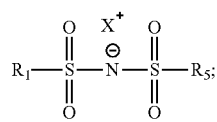

and R$_5$ is selected from the group consisting of:
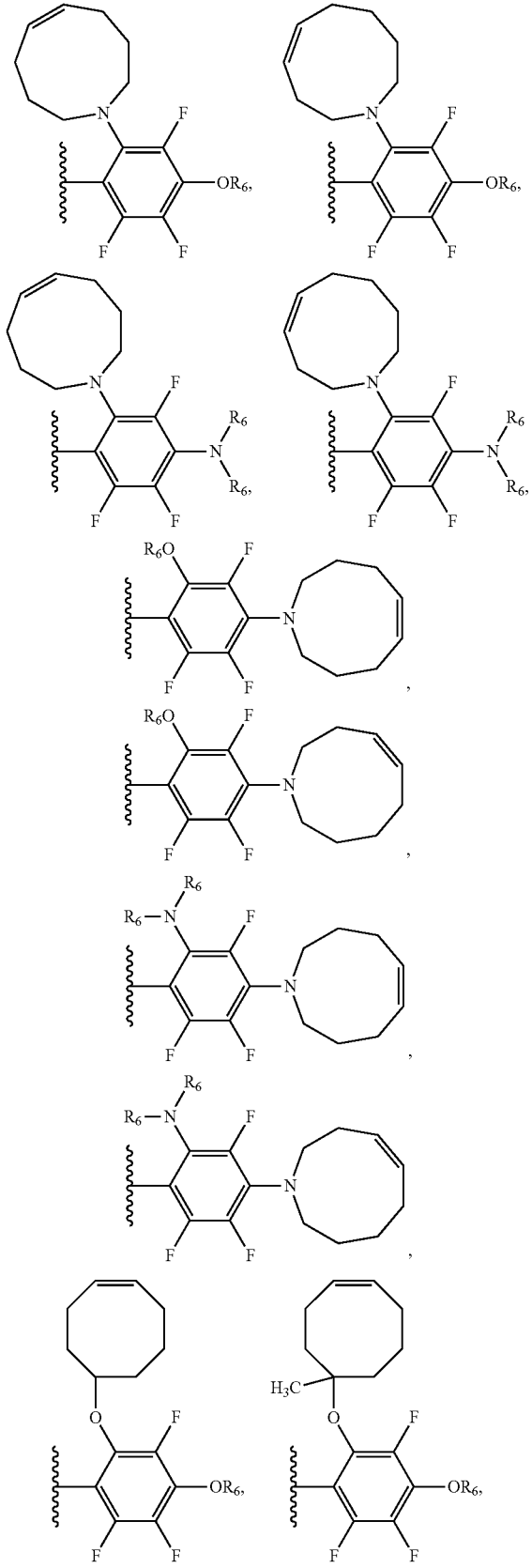
-continued
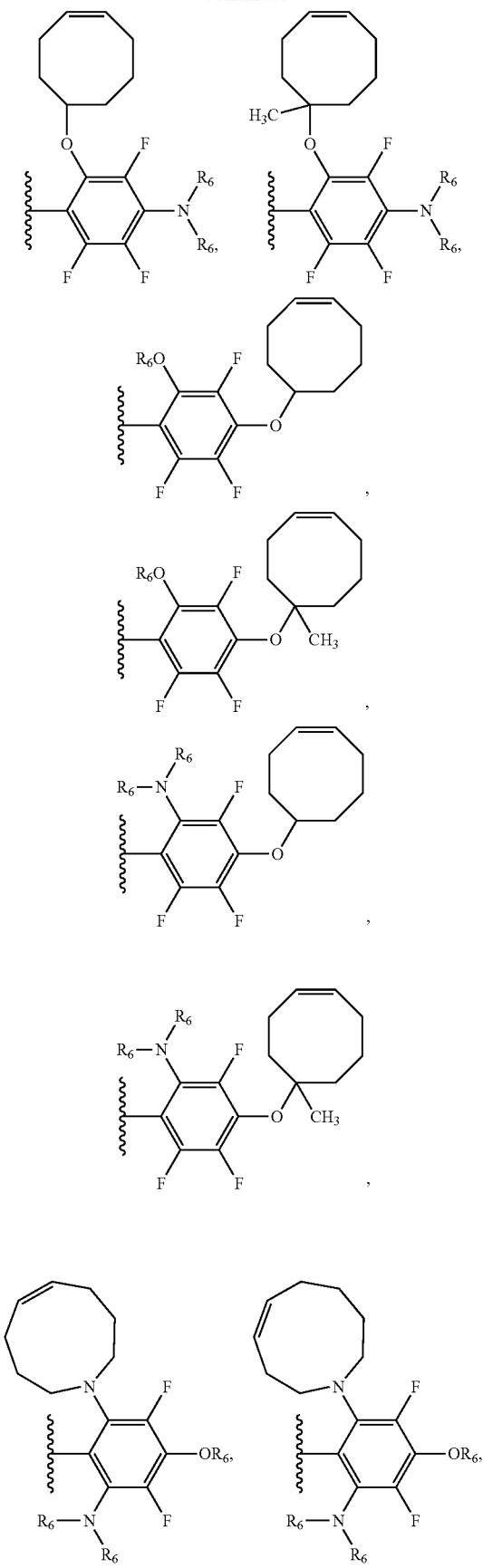

91
-continued
92
-continued
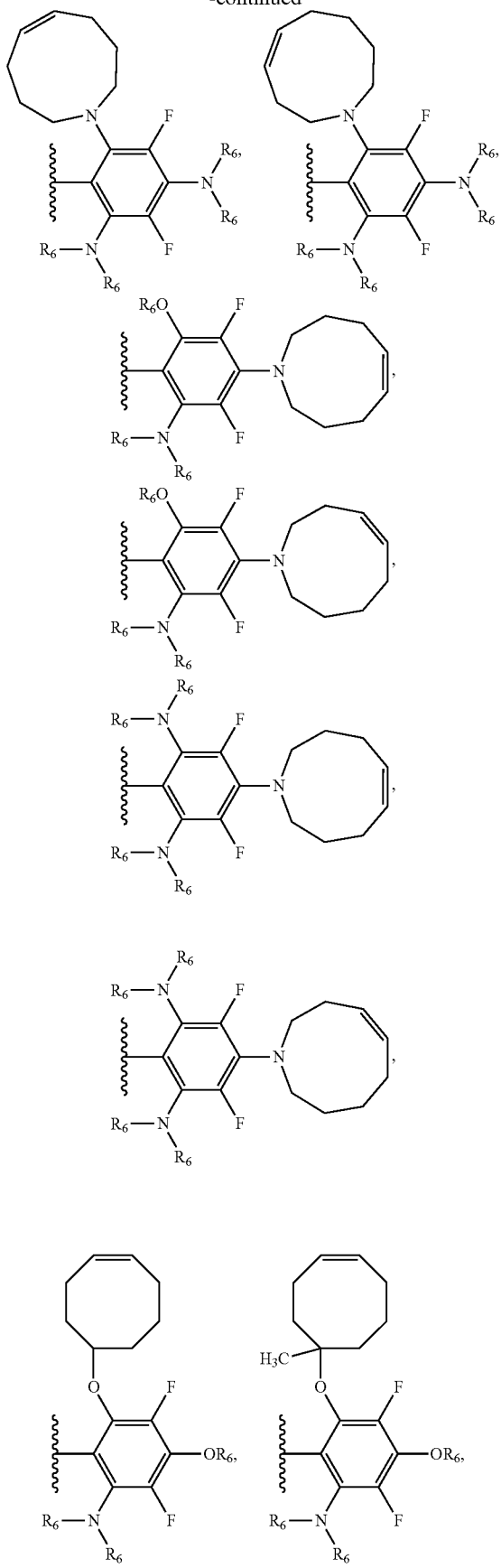
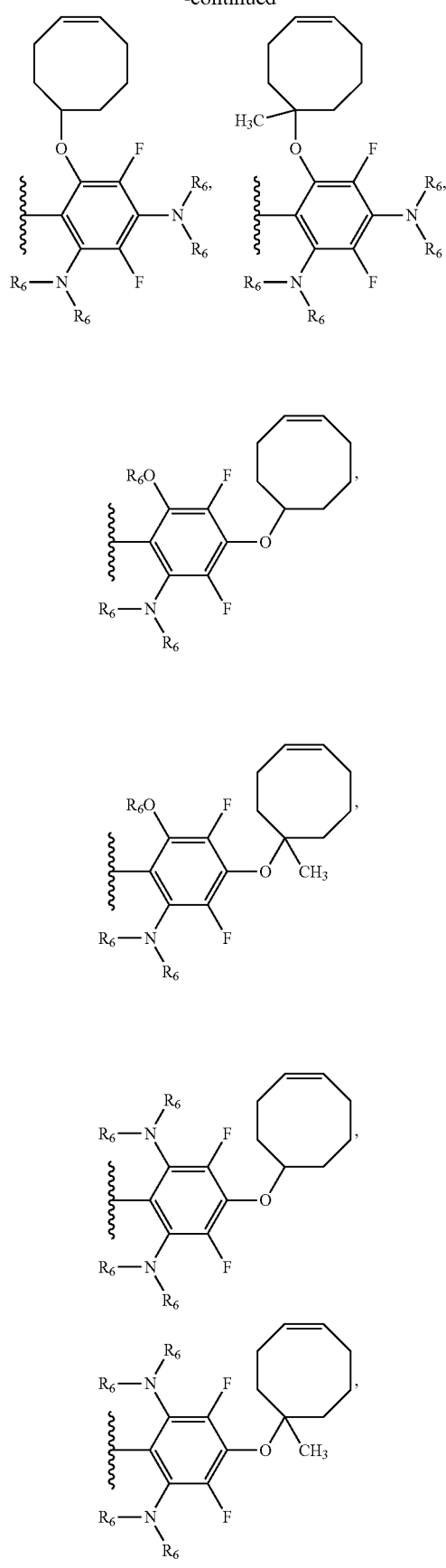

-continued

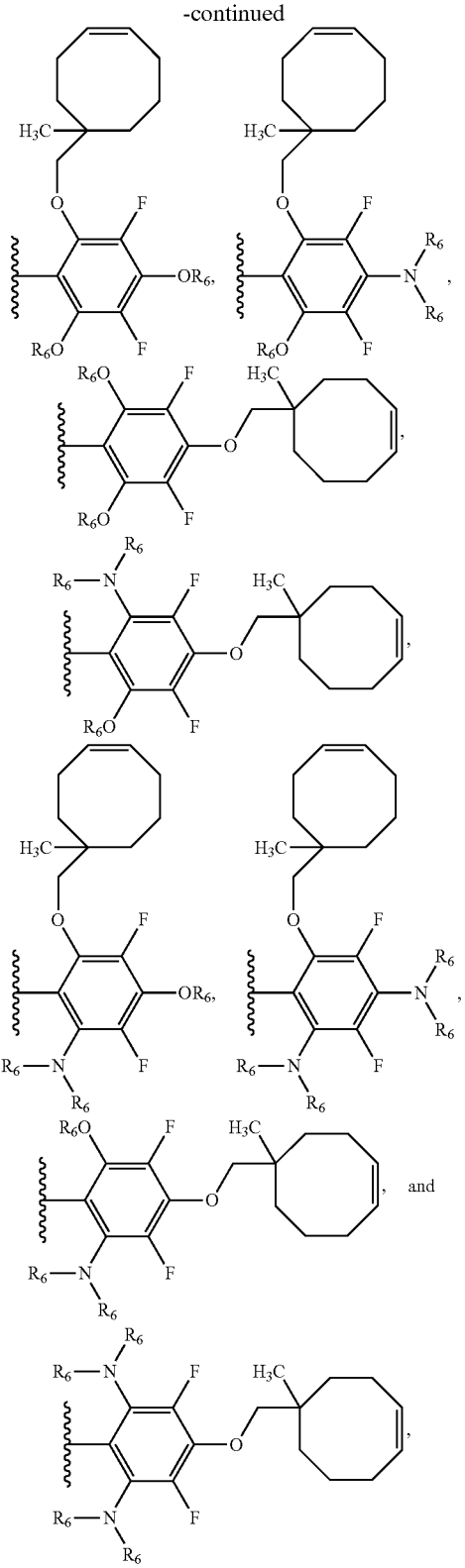

wherein:
each $R_6$ independently is hydrogen; optionally substituted alkyl; optionally substituted heteroalkyl; optionally substituted aryl; or optionally substituted heteroaryl; or two $R_6$ bonded to the same atom are taken together to form an optionally substituted cyclic heteroalkyl.

22. The compound of claim 1, wherein the compound is selected from the group consisting of:

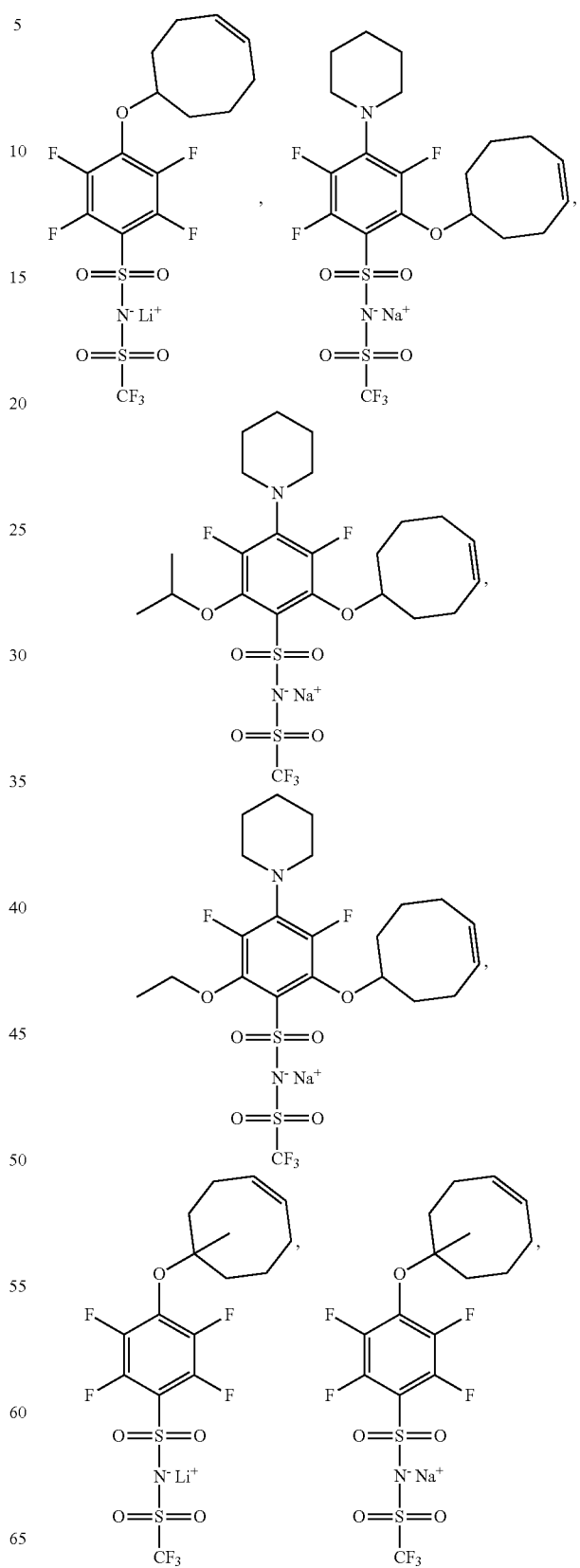

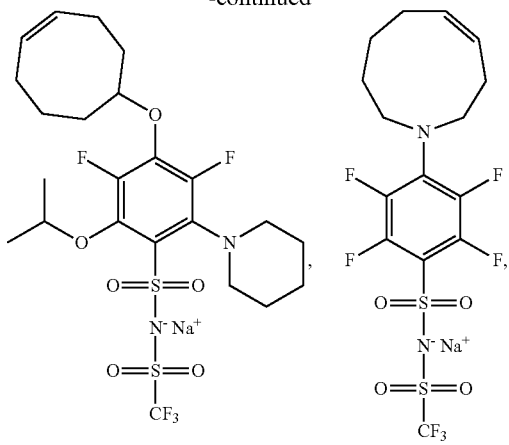
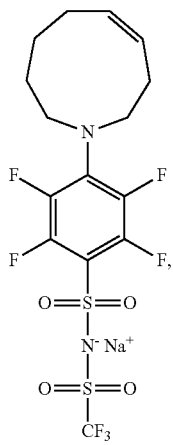
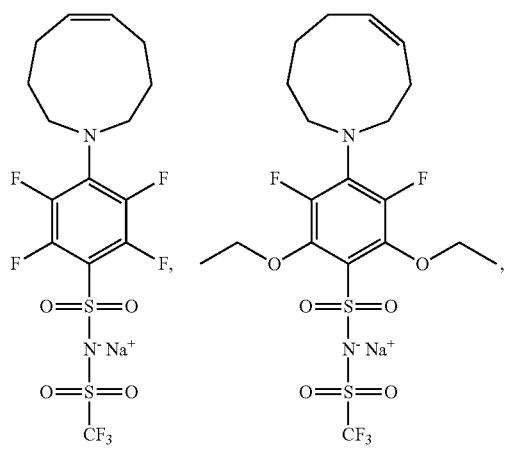
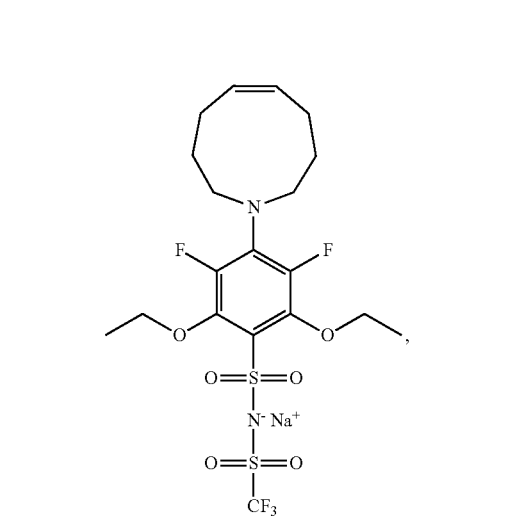
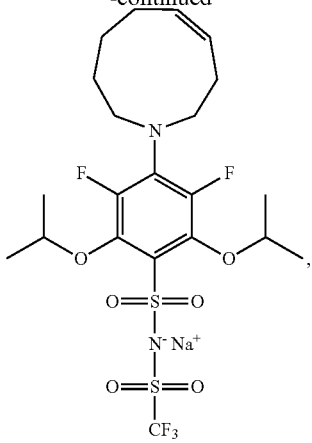
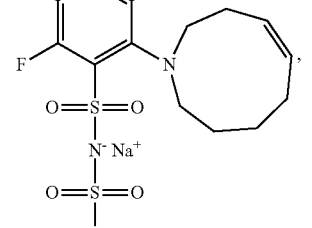
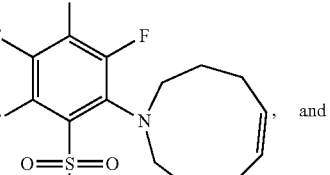
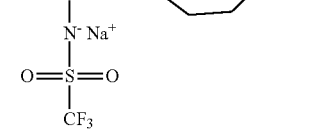
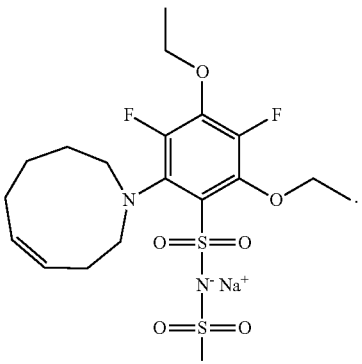
* * * * *

UNITED STATES PATENT AND TRADEMARK OFFICE
CERTIFICATE OF CORRECTION

PATENT NO. : 11,155,674 B2
APPLICATION NO. : 15/876106
DATED : October 26, 2021
INVENTOR(S) : Jeremiah A. Johnson et al.

Page 1 of 4

It is certified that error appears in the above-identified patent and that said Letters Patent is hereby corrected as shown below:

In the Claims

In Claim 16, at Column 84, Lines 11-23, the formula:

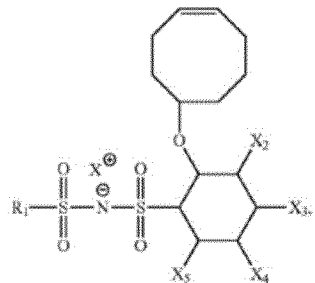

Should be replaced with the formula:

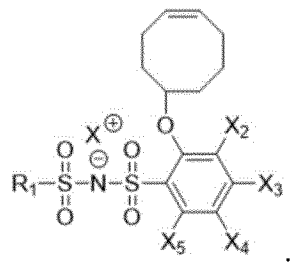

Signed and Sealed this
Tenth Day of May, 2022

Katherine Kelly Vidal
*Director of the United States Patent and Trademark Office*

CERTIFICATE OF CORRECTION (continued)
U.S. Pat. No. 11,155,674 B2

In Claim 21, at Column 89, Lines 3-66; and Column 90, Lines 1-51, the formulae:

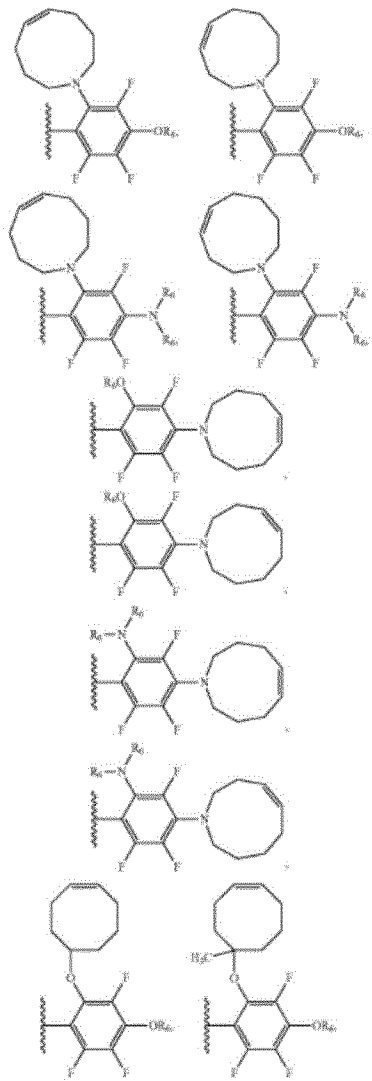

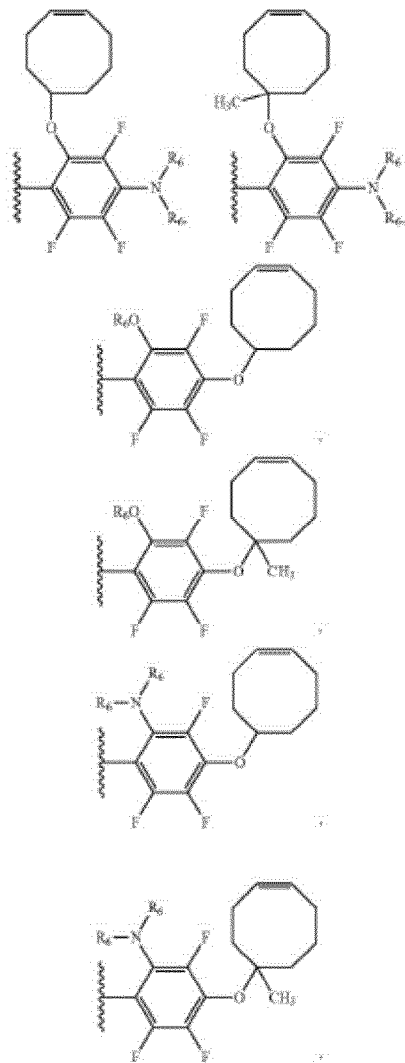

CERTIFICATE OF CORRECTION (continued)
U.S. Pat. No. 11,155,674 B2

Should be replaced with the formulae: